(12) United States Patent
Yoshida et al.

(10) Patent No.: US 11,903,308 B2
(45) Date of Patent: Feb. 13, 2024

(54) COMPOUND, MATERIAL FOR ORGANIC ELECTROLUMINESCENT ELEMENT, ORGANIC ELECTROLUMINESCENT ELEMENT, AND ELECTRONIC DEVICE

(71) Applicant: IDEMITSU KOSAN CO.,LTD., Chiyoda-ku (JP)

(72) Inventors: Kei Yoshida, Chiba (JP); Masatoshi Saito, Ichihara (JP); Ryoji Maeda, Chiba (JP); Masato Nakamura, Sumida-ku (JP); Tetsuya Masuda, Chiba (JP)

(73) Assignee: IDEMITSU KOSAN CO., LTD., Chiyoda-ku (JP)

( * ) Notice: Subject to any disclaimer, the term of this patent is extended or adjusted under 35 U.S.C. 154(b) by 333 days.

(21) Appl. No.: 17/273,563

(22) PCT Filed: Sep. 2, 2019

(86) PCT No.: PCT/JP2019/034437
§ 371 (c)(1),
(2) Date: Apr. 29, 2021

(87) PCT Pub. No.: WO2020/050217
PCT Pub. Date: Mar. 12, 2020

(65) Prior Publication Data
US 2021/0359217 A1 Nov. 18, 2021

(30) Foreign Application Priority Data

Sep. 7, 2018 (JP) .................................. 2018-168361
Mar. 27, 2019 (JP) .................................. 2019-061161

(51) Int. Cl.
*C07D 209/82* (2006.01)
*C07D 403/14* (2006.01)
(Continued)

(52) U.S. Cl.
CPC ......... *H10K 85/654* (2023.02); *C07D 401/14* (2013.01); *C07D 403/14* (2013.01);
(Continued)

(58) Field of Classification Search
CPC ........................... C07D 209/82; C07D 403/14
See application file for complete search history.

(56) References Cited

U.S. PATENT DOCUMENTS 9,577,199 B2 * 2/2017 Lecloux ............... C07D 209/86
2012/0126221 A1 5/2012 Kitamura et al.
(Continued)

FOREIGN PATENT DOCUMENTS

JP 2003-80760 A 3/2003
JP 2011-49511 A 3/2011
(Continued)

OTHER PUBLICATIONS

International Search Report dated Nov. 19, 2019 in PCT/JP2019/034437 filed on Sep. 2, 2019, 2 pages.

*Primary Examiner* — Vu A Nguyen
(74) *Attorney, Agent, or Firm* — Oblon, McClelland, Maier & Neustadt, L.L.P.

(57) ABSTRACT

A compound of the following formula (1) and others. $R^1$ to $R^{24}$, $R^{31}$ to $R^{35}$, $A^1$ and $A^2$ are as defined in the specification, n is an integer of 0 to 3, when $A^1$ is an (n+1)-valent residue of benzene, n is an integer of 1 or more, and when n is 0, $(A^2)_0$ is a hydrogen atom.

(Continued)

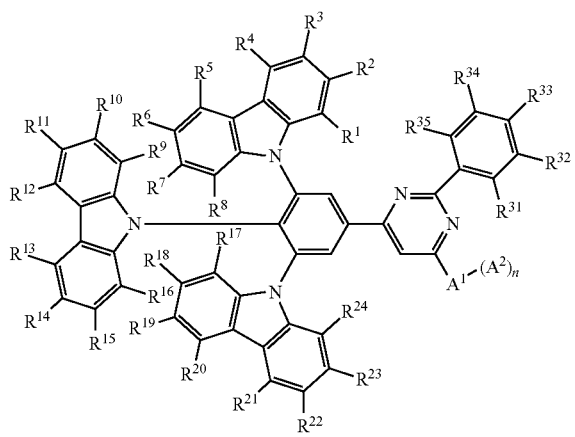

33 Claims, 1 Drawing Sheet

(51) Int. Cl.
- C07D 239/26 (2006.01)
- H01L 51/00 (2006.01)
- H01L 51/50 (2006.01)
- H10K 85/60 (2023.01)
- C07D 401/14 (2006.01)
- C07D 409/14 (2006.01)
- H10K 50/16 (2023.01)

(52) U.S. Cl.
CPC ....... C07D 409/14 (2013.01); H10K 85/6572 (2023.02); H10K 85/6576 (2023.02); *H10K 50/16* (2023.02)

(56) References Cited

U.S. PATENT DOCUMENTS

| | | | |
|---|---|---|---|
| 2012/0126691 | A1 | 5/2012 | Ise et al. |
| 2018/0170914 | A1* | 6/2018 | Miyata ................ C07D 265/38 |

FOREIGN PATENT DOCUMENTS

| | | |
|---|---|---|
| JP | 2011-71474 A | 4/2011 |
| JP | 2012-19172 A | 1/2012 |
| JP | 2014-216576 A | 11/2014 |
| JP | 2018-35129 A | 3/2018 |
| WO | WO 2016/181846 A1 | 11/2016 |

* cited by examiner

[Fig. 1]
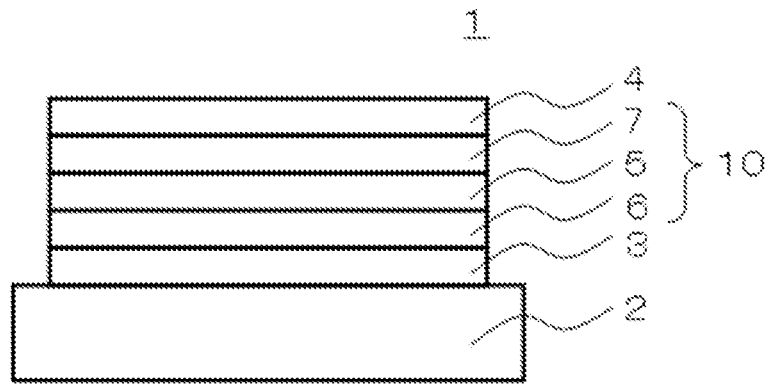
[Fig. 2]
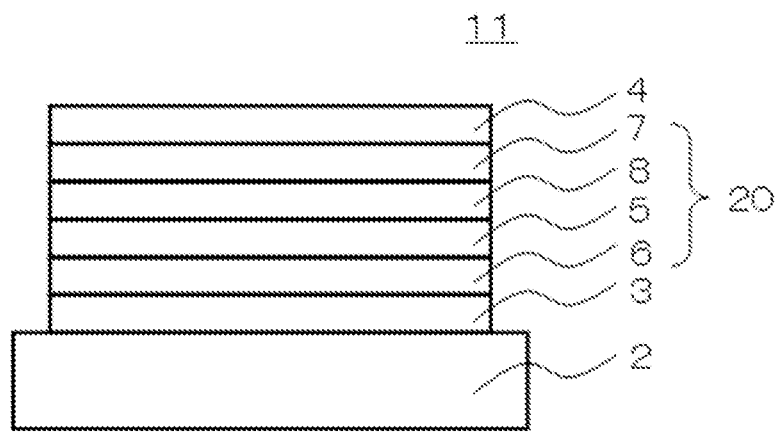
[Fig. 3]
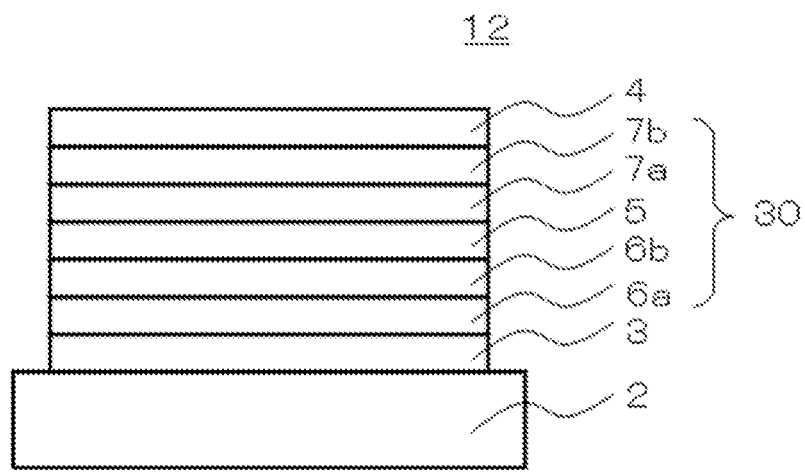

COMPOUND, MATERIAL FOR ORGANIC ELECTROLUMINESCENT ELEMENT, ORGANIC ELECTROLUMINESCENT ELEMENT, AND ELECTRONIC DEVICE

TECHNICAL FIELD

The present invention relates to a compound, a material for organic electroluminescent devices using the same, an organic electroluminescent device, and an electronic device.

BACKGROUND ART

In general, an organic electroluminescent device (hereinafter this may be referred to as "an organic EL device") includes an anode, a cathode, and an organic layer sandwiched between the anode and the cathode. When a voltage is applied between both electrodes, electrons from the cathode side, and holes from the anode side are injected into a light emitting region. The injected electrons and holes are recombined in the light emitting region to generate an excited state. When the excited state returns to a ground state, light is emitted. Thus, development of a compound which efficiently transports electrons or holes to a light emitting region, and promotes recombination of the electrons with the holes is important in obtaining a high-performance organic EL device.

As literature describing compounds for use for organic EL devices, there are mentioned PTL 1 and PTL 2.

CITATION LIST

Patent Literature

PTL 1: WO2003/080760
PTL 2: WO2016/181846

SUMMARY OF INVENTION

Technical Problem

Many compounds have conventionally been reported as a material for producing organic EL devices, but there is still a demand for a compound that further improves characteristics of organic EL devices.

The present invention has been made in order to solve the above problems, and an object thereof is to provide a compound capable of securing high-performance organic EL devices, more specifically, a compound capable of realizing prolongation of lifetime thereof, and to provide a high-performance organic EL device, more specifically a lifetime-prolonged organic EL device, and an electronic device containing such an organic EL device.

Solution to Problem

The present inventors have conducted repetitive intensive studies in order to solve the above problem, and as a result, have found that compounds represented by the following formula (1) and formula (1A) can realize a high-performance organic EL device, more specifically an organic EL device capable of realizing prolonged lifetime, and have completed the present invention.

In one aspect, the present invention provides an organic electroluminescent device including a cathode, an anode, and organic layers disposed between the cathode and the anode, wherein:
the organic layers include a light emitting layer, and a first layer disposed between the light emitting layer and the cathode, and
the first layer contains a compound represented by the following formula (1A) (hereinafter this may be referred to as a compound (1A)).

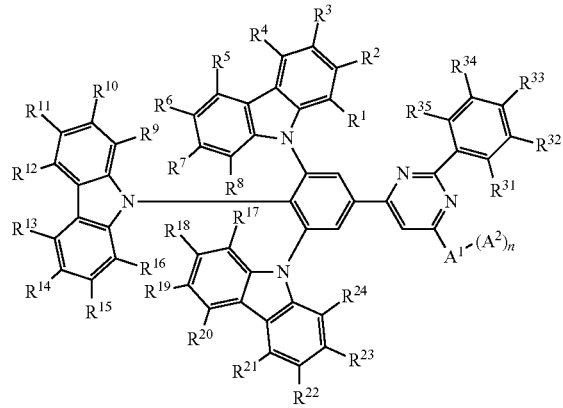

(1A)

In the formula,
$R^1$ to $R^{24}$ each independently represent a hydrogen atom, or a substituent, and the substituent is a substituted or unsubstituted aryl group having 6 to 30 ring carbon atoms, a substituted or unsubstituted heteroaryl group having 5 to 30 ring atoms, a substituted or unsubstituted alkyl group having 1 to 50 carbon atoms, a substituted or unsubstituted cycloalkyl group having 5 to 50 ring carbon atoms, or a cyano group,
at least one pair of $R^{31}$ and $R^{32}$, $R^{32}$ and $R^{33}$, $R^{33}$ and $R^{34}$, and $R^{34}$ and $R^{35}$ each independently bond to each other to form a substituted or unsubstituted aromatic hydrocarbon ring having 6 to 30 ring carbon atoms, a substituted or unsubstituted hetero ring having 5 to 30 ring atoms, or a substituted or unsubstituted aliphatic hydrocarbon ring having 5 to 50 ring carbon atoms, or $R^{31}$ and $R^{32}$, $R^{32}$ and $R^{33}$, $R^{33}$ and $R^{34}$, and $R^{34}$ and $R^{35}$ do not bond to form a ring, and in the case where they do not bond to form a ring, $R^{31}$ to $R^{35}$ each independently represent a hydrogen atom or a substituent, and the substituent is a substituted or unsubstituted aryl group having 6 to 30 ring carbon atoms, a substituted or unsubstituted heteroaryl group having 5 to 30 ring atoms, a substituted or unsubstituted alkyl group having 1 to 50 carbon atoms, a substituted or unsubstituted cycloalkyl group having 5 to 50 ring carbon atoms, or a cyano group,
$A^1$ represents a substituted or unsubstituted, (n+1)-valent residue of an aromatic hydrocarbon having 6 to 30 ring carbon atoms, or a substituted or unsubstituted, (n+1)-valent residue of an aromatic heterocyclic compound having 5 to 30 ring atoms, $A^2$ each independently represents a substituted or unsubstituted aryl group having 6 to 30 ring carbon atoms, a substituted or unsubstituted heteroaryl group having 5 to 30 ring atoms, or a cyano group, n represents an integer of 0 to 3, and when n is 0, $(A^2)_0$ is a hydrogen atom.

In another aspect, the present invention provides a compound represented by the following formula (1) (hereinafter this may be referred to as a compound (1)).

(1)

In the formula, $R^1$ to $R^{24}$ each independently represent a hydrogen atom, or a substituent, and the substituent is a substituted or unsubstituted aryl group having 6 to 30 ring carbon atoms, a substituted or unsubstituted heteroaryl group having 5 to 30 ring atoms, a substituted or unsubstituted alkyl group having 1 to 50 carbon atoms, a substituted or unsubstituted cycloalkyl group having 5 to 50 ring carbon atoms, or a cyano group, at least one pair of $R^{31}$ and $R^{32}$, $R^{32}$ and $R^{33}$, $R^{33}$ and $R^{34}$, and $R^{34}$ and $R^{35}$ each independently bond to each other to form a substituted or unsubstituted aromatic hydrocarbon ring having 6 to 30 ring carbon atoms, a substituted or unsubstituted hetero ring having 5 to 30 ring atoms, or a substituted or unsubstituted aliphatic hydrocarbon ring having 5 to 50 ring carbon atoms, or $R^{31}$ and $R^{32}$, $R^{32}$ and $R^{33}$, $R^{33}$ and $R^{34}$, and $R^{34}$ and $R^{35}$ do not bond to form a ring, and in the case where they do not bond to form a ring, $R^{31}$ to $R^{35}$ each independently represent a hydrogen atom or a substituent, and the substituent is a substituted or unsubstituted aryl group having 6 to 30 ring carbon atoms, a substituted or unsubstituted heteroaryl group having 5 to 30 ring atoms, a substituted or unsubstituted alkyl group having 1 to 50 carbon atoms, a substituted or unsubstituted cycloalkyl group having 5 to 50 ring carbon atoms, or a cyano group, $A^1$ represents a substituted or unsubstituted, (n+1)-valent residue of an aromatic hydrocarbon having 6 to 30 ring carbon atoms, or a substituted or unsubstituted, (n+1)-valent residue of an aromatic heterocyclic compound having 5 to 30 ring atoms, $A^2$ each independently represents a substituted or unsubstituted aryl group having 6 to 30 ring carbon atoms, a substituted or unsubstituted heteroaryl group having 5 to 30 ring atoms, or a cyano group, n represents an integer of 0 to 3, when $A^1$ is an (n+1)-valent residue of benzene, n is an integer of 1 or more, and when n is 0, $(A^2)_0$ is a hydrogen atom.

In a further aspect, the present invention provides a material for organic electroluminescent devices containing the compound (1), and an organic electroluminescent device.

In a still further aspect, the present invention provides an electronic device including the organic electroluminescent device.

Advantageous Effects of Invention

The compound (1) or the compound (1A) realizes a high-efficiency organic EL device. More specifically, the compound realizes a lifetime-prolonged organic EL device.

BRIEF DESCRIPTION OF DRAWINGS

FIG. 1 is a schematic view illustrating an example of a layer configuration of an organic electroluminescent device of an embodiment of the present invention.

FIG. 2 is a schematic view illustrating another example of a layer configuration of an organic electroluminescent device of an embodiment of the present invention.

FIG. 3 is a schematic view illustrating still another example of a layer configuration of an organic electroluminescent device of an embodiment of the present invention.

DESCRIPTION OF EMBODIMENTS

In the present specification, the term of "XX to YY carbon atoms" referred to by "a substituted or unsubstituted group ZZ having XX to YY carbon atoms" indicates the number of carbon atoms of the unsubstituted group ZZ, and does not include any carbon atom in the substituent of the substituted group ZZ.

In the present specification, the term of "XX to YY atoms" referred to by "a substituted or unsubstituted group ZZ having XX to YY atoms" indicates the number of atoms of the unsubstituted group ZZ, and does not include any atom in the substituent of the substituted group ZZ.

In the present specification, the "unsubstituted group ZZ" in the case of the "substituted or unsubstituted group ZZ" indicates that a hydrogen atom in the group ZZ is not substituted with a substituent.

In the present specification, the "hydrogen atom" includes isotopes having different numbers of neutrons, that is, protium, deuterium, and tritium.

The number of "ring carbon atoms" referred to in the present specification indicates the number of carbon atoms among the atoms forming the ring itself of a compound with a structure in which the atoms are cyclically bonded (for example, a monocyclic compound, a fused ring compound, a cross-linked compound, a carbocyclic compound, and a heterocyclic compound). If the ring is substituted with a substituent, the carbon atom included in the substituent is not included in the ring carbon atom. The same applies to the number of "ring carbon atoms" described below unless otherwise noted. For example, a benzene ring has 6 ring carbon atoms, a naphthalene ring has 10 ring carbon atoms, a pyridine ring has 5 ring carbon atoms, and a furan ring has 4 ring carbon atoms. Also, when the benzene ring or the naphthalene ring is substituted with, for example, an alkyl group as a substituent, the carbon atom in the alkyl group is not counted as the number of ring carbon atoms. Also, in a case of a fluorene ring to which, for example, a fluorene ring as a substituent is bonded (inclusive of a spirofluorene ring), the carbon atom in the fluorene ring as the substituent is not counted as the number of ring carbon atoms.

The number of "ring atoms" referred to in the present specification indicates the number of atoms forming the ring itself of a compound (for example, a monocyclic compound, a fused ring compound, a cross-linked compound, a carbocyclic compound, and a heterocyclic compound) with a structure in which the atoms are cyclically bonded (for example, a monocyclic ring, a fused ring, a ring assembly). The atom not forming the ring (for example, a hydrogen atom that terminates a bond of atoms forming the ring), and the atom included in a substituent if the ring is substituted with the substituent, are not counted as the number of ring atoms. The same applies to the number of "ring atoms" described below unless otherwise noted. For example, a pyridine ring has 6 ring atoms, a quinazoline ring has 10 ring atoms, and a furan ring has 5 ring atoms. The hydrogen atom bonded to each ring carbon atom in the pyridine ring or the quinazoline ring, and the atom constituting a substituent, are not counted as the number of ring atoms. Also, in a case of a fluorene ring to which, for example, a fluorene ring as a substituent is bonded (inclusive of a spirobifluorene ring), the atom in the fluorene ring as the substituent is not counted as the number of ring atoms.

In the present specification, it can be said that a preferred embodiment (for example, compounds, various groups, and numerical ranges) may be arbitrarily combined with any other embodiment (for example, compounds, various groups, and numerical ranges), and also, a combination of preferred embodiments (including a more preferable embodiment, a further preferable embodiment, and a particularly preferable embodiment) is more preferred.

1. Compound

In one embodiment of the present invention, the compound (1) is represented by the formula (1).

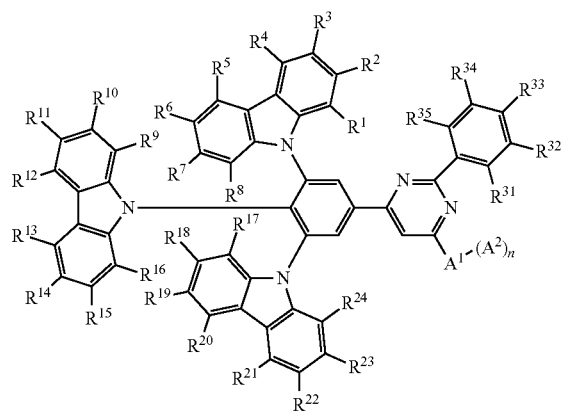

(1)

The compound (1) of this embodiment is preferably a compound represented by any of the following formulae (2) to (4), more preferably by any of the formulae (2) to (3).

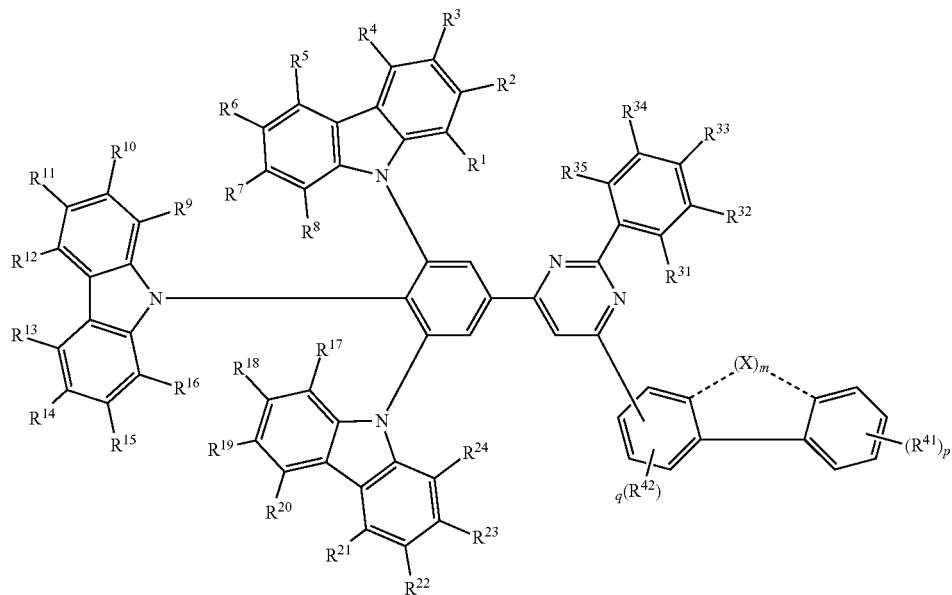

(2)

-continued
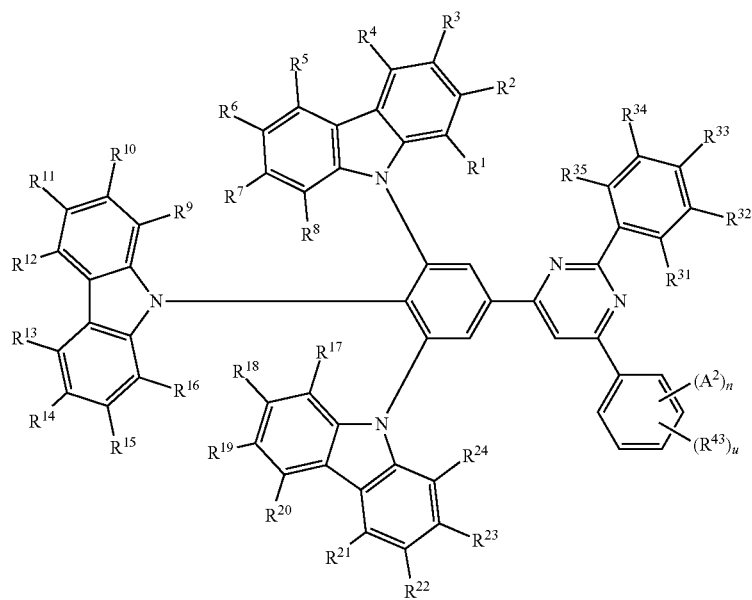
(3)
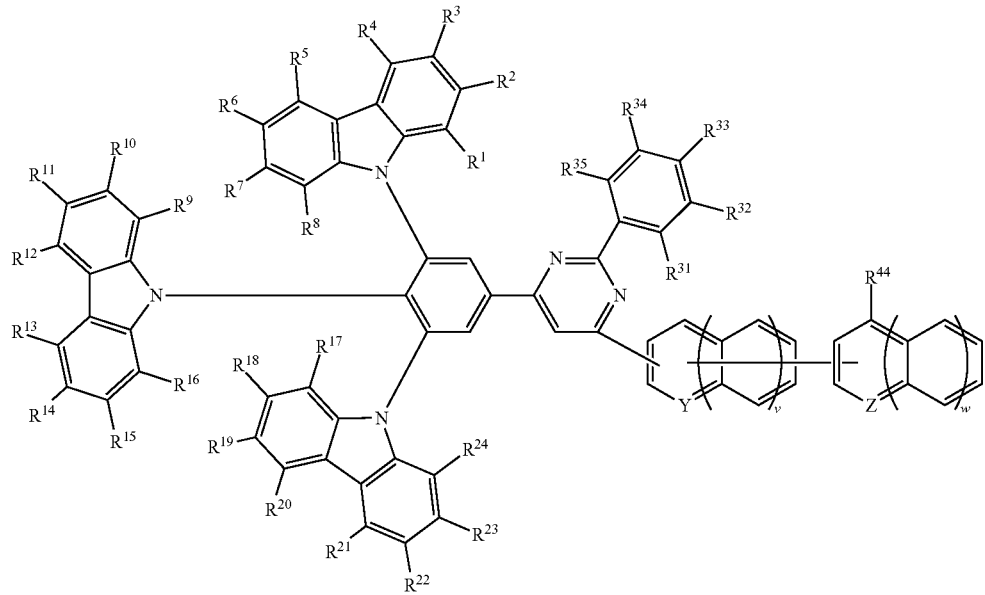
(4)

The compound (1) of this embodiment is preferably a compound represented by any of the following formulae (5) to (17), more preferably by any of the following formulae (5) to (10), even more preferably by any of the following formulae (6) to (8), further more preferably by any of the following formulae (6) to (7).
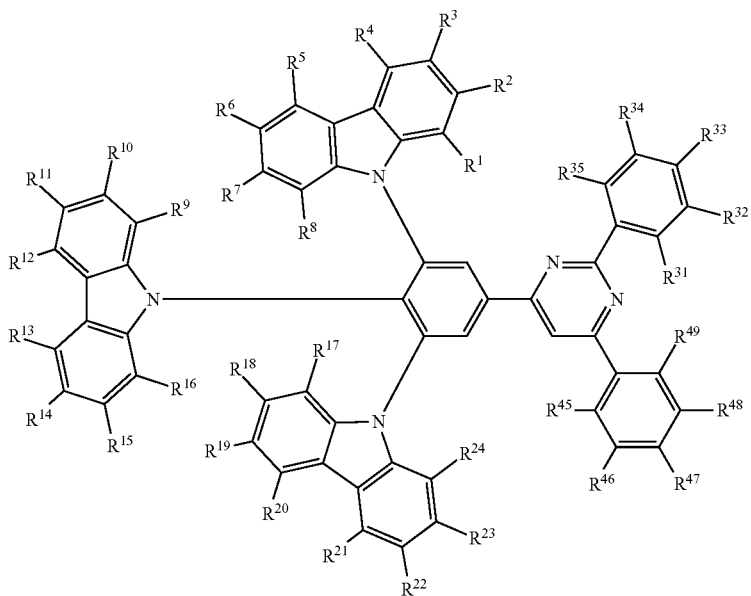
(5)
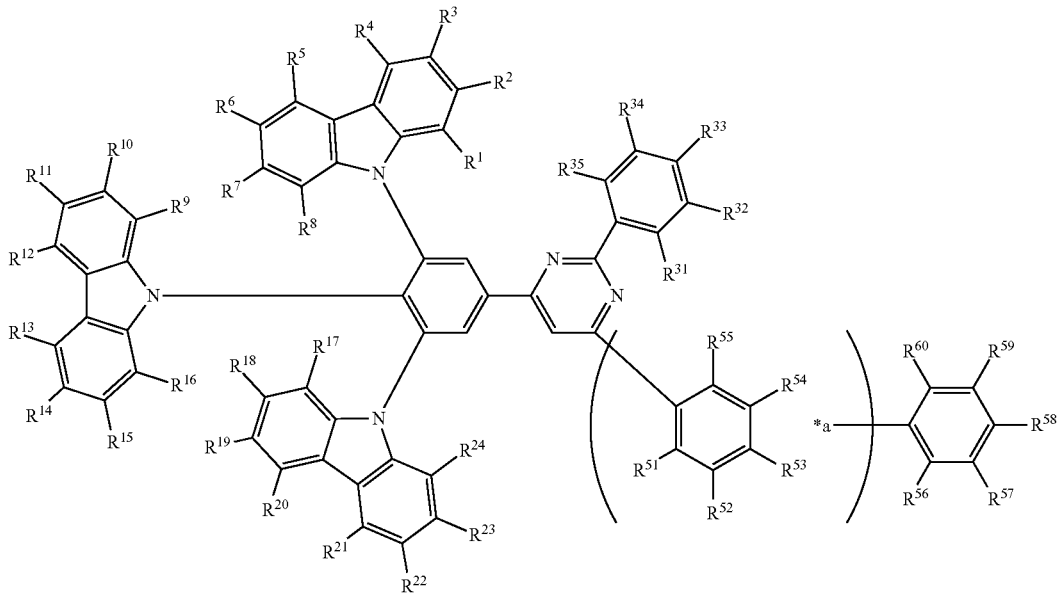
(6)

(7)
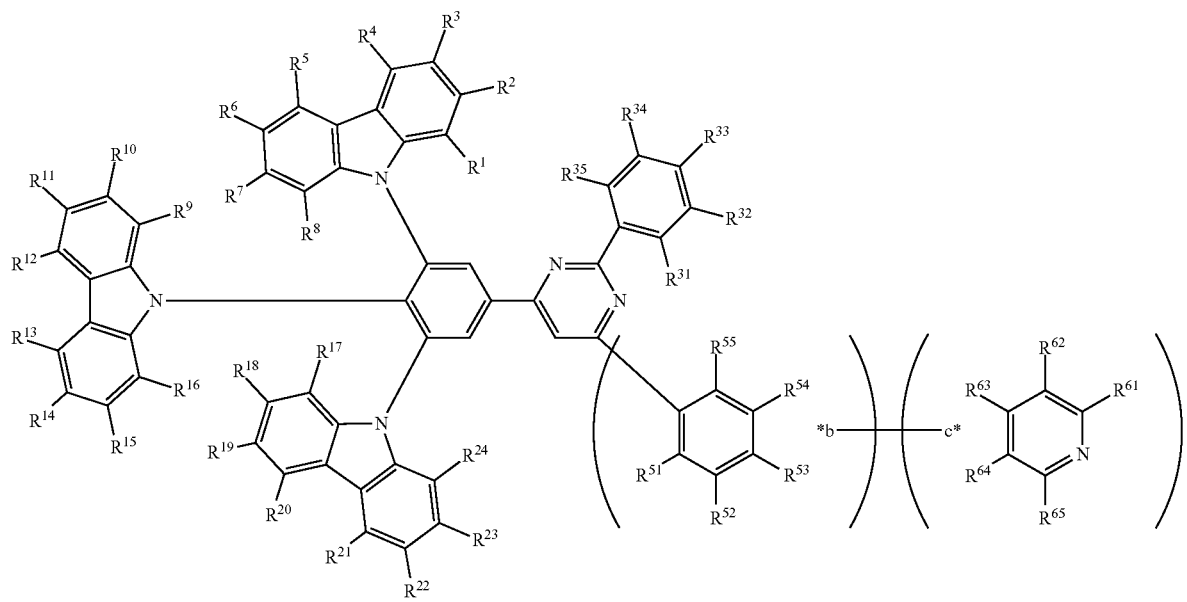
(8)
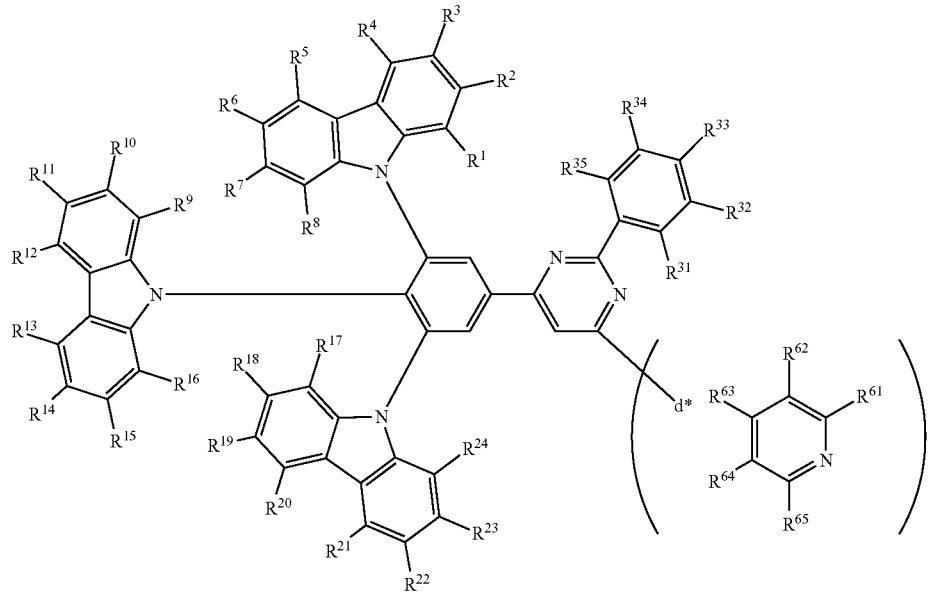

-continued
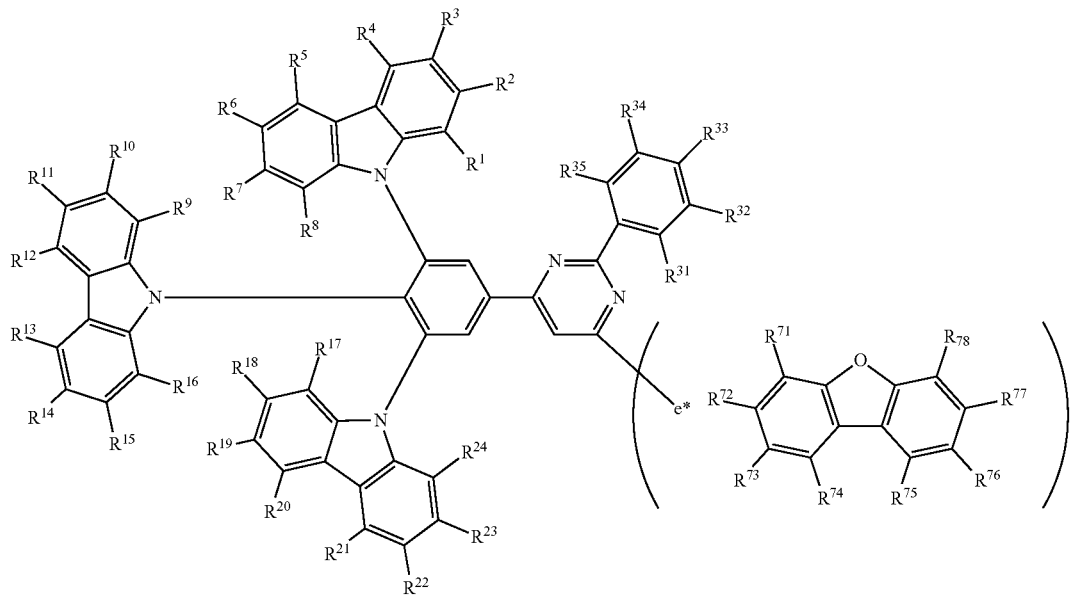
(9)
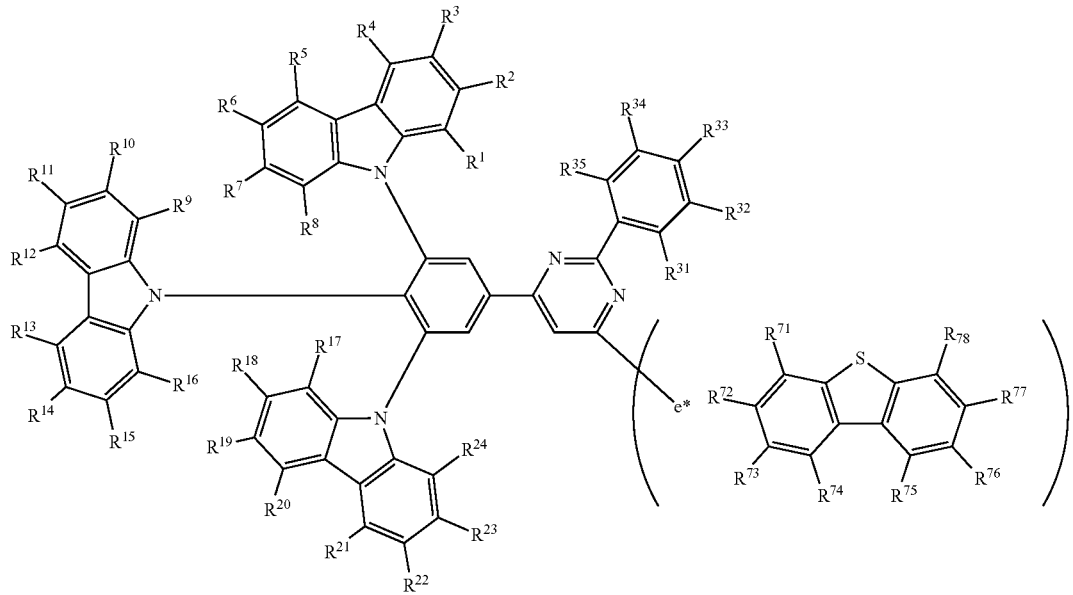
(10)

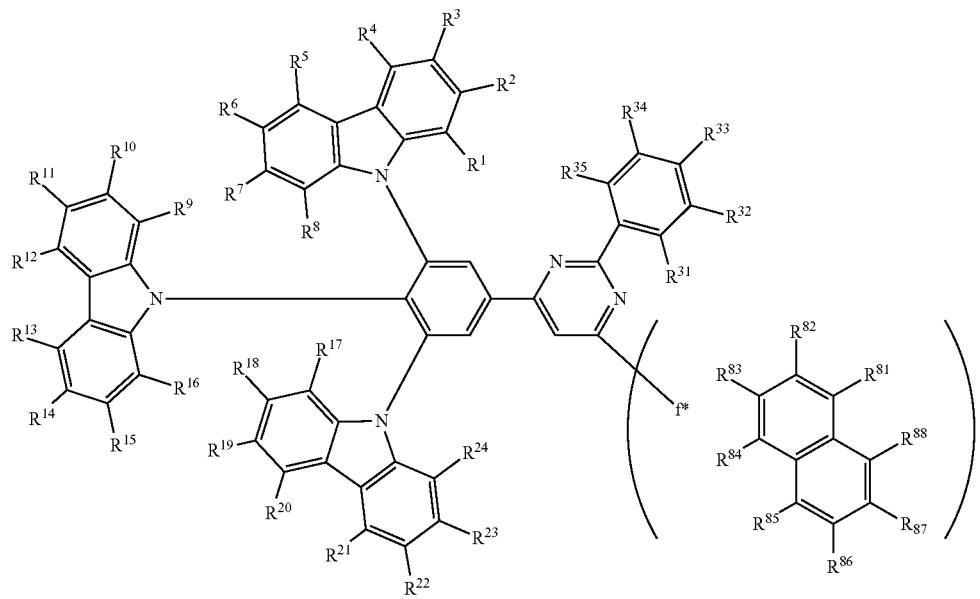
(11)
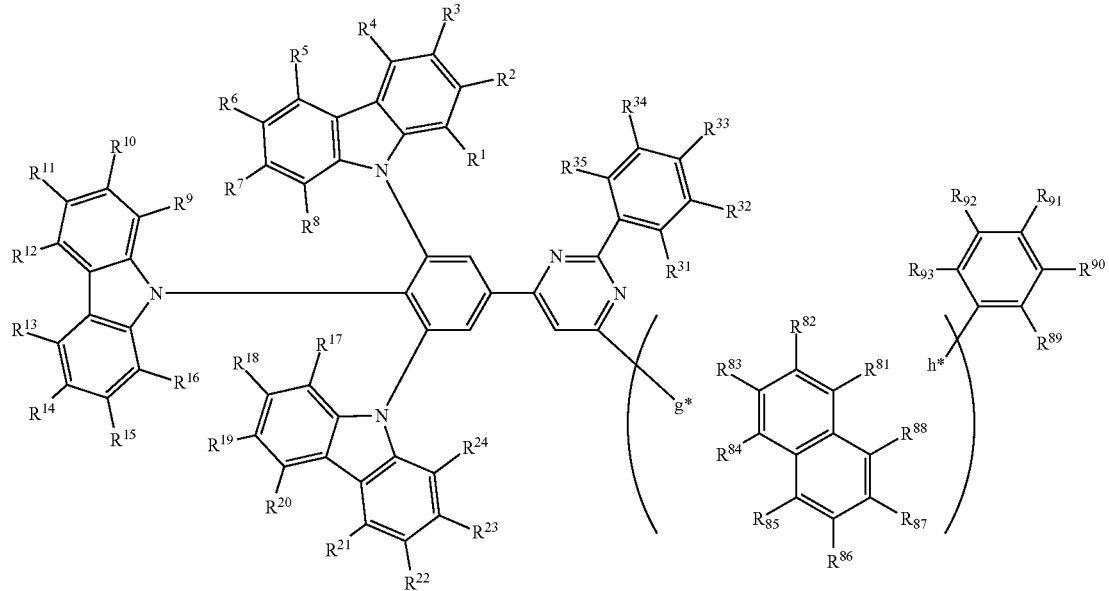
(12)

(13)
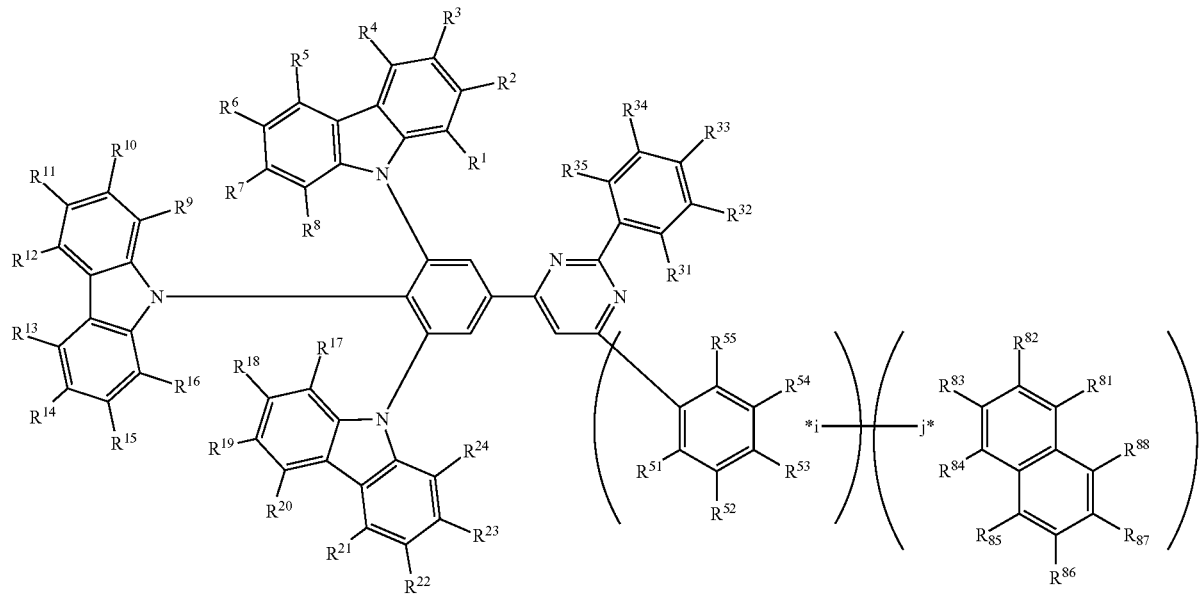
(14)
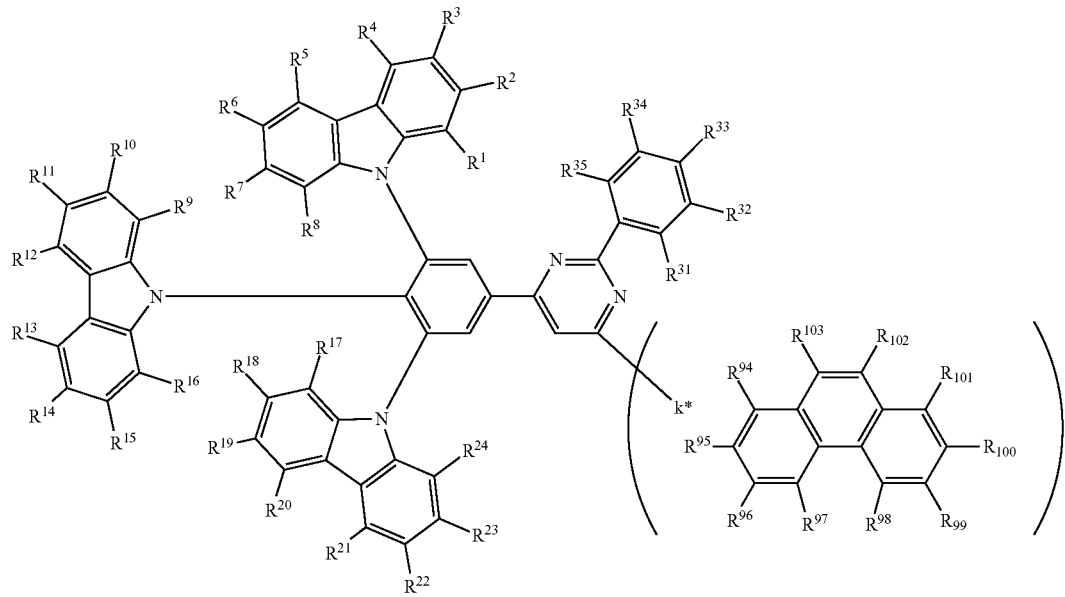

(15)
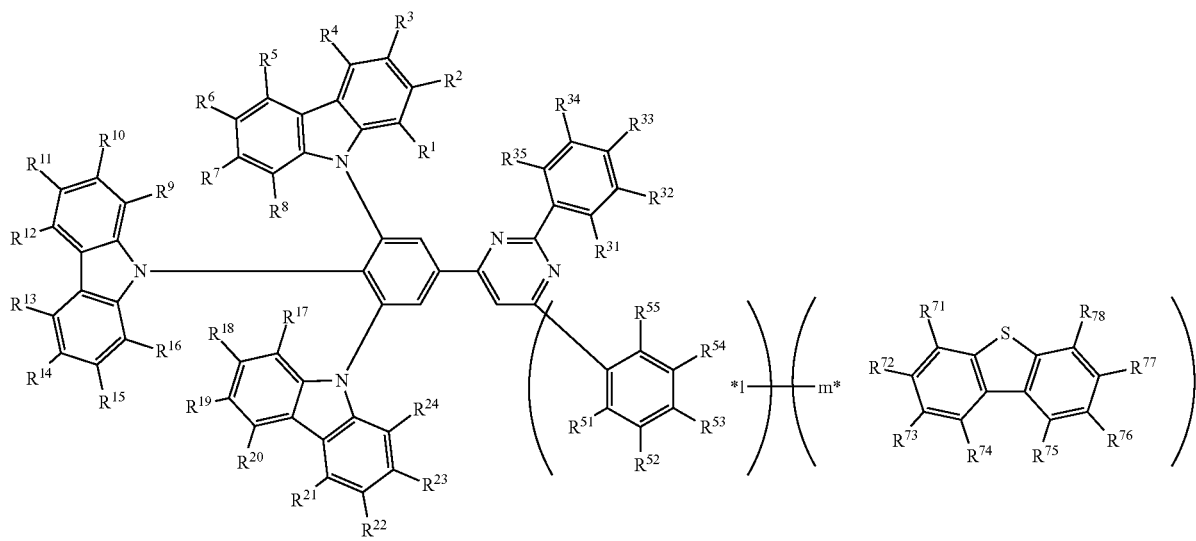
(16)
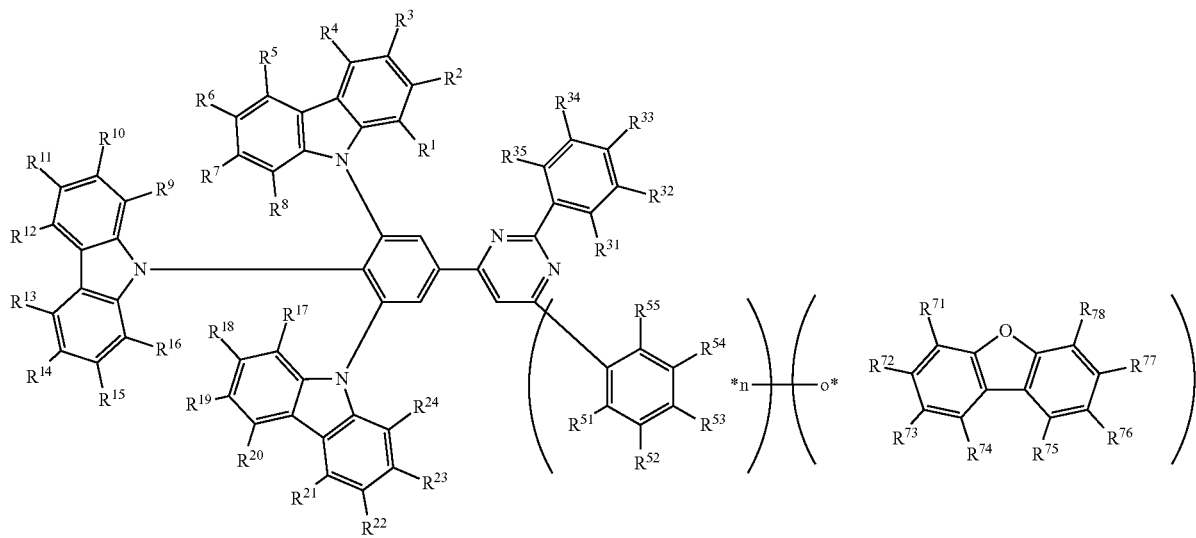

-continued (17)

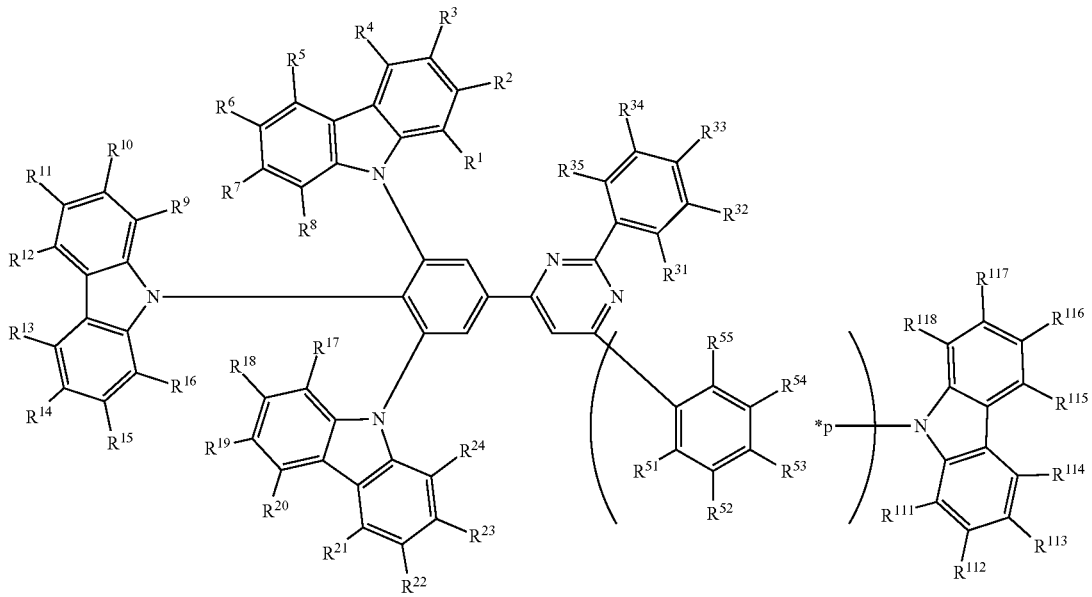

Next, symbols in the formula (1) to the formula (17) are described.

Described in the present specification, an aryl group having 6 to 30 ring carbon atoms, an aromatic hydrocarbon ring having 6 to 30 ring carbon atoms, an aromatic hydrocarbon having 6 to 30 ring carbon atoms; a heteroaryl group having 5 to 30 ring atoms, an aromatic heterocyclic compound having 5 to 30 ring atoms, a hetero ring having 5 to 30 ring atoms;
  an alkyl group having 1 to 50 carbon atoms;
  a cycloalkyl group having 5 to 50 ring carbon atoms, an aliphatic hydrocarbon ring having 5 to 50 ring carbon atoms; and
  an arbitrary substituent to be meant by the wording "substituted or unsubstituted";
have the following meanings, unless otherwise specifically indicated.

Specifically, the aryl group having 6 to 30 ring carbon atoms described in the present specification is, for example, a phenyl group, a biphenylyl group, a terphenylyl group, a biphenylenyl group, a naphthyl group, an anthryl group, a benzoanthryl group, a phenanthryl group, a benzophenanthryl group, a phenalenyl group, a picenyl group, a pentaphenyl group, a pyrenyl group, a chrysenyl group, a benzochrysenyl group, a fluorenyl group, a fluoranthenyl group, a perylenyl group, a triphenylenyl group, or a benzotriphenylenyl group.

Preferably, the group is a phenyl group, a naphthyl group, a phenanthryl group, a benzophenanthryl group, a fluorenyl group, a triphenylenyl group, a pyrenyl group, a fluoranthenyl group, or a benzotriphenylenyl group, more preferably a phenyl group, a naphthyl group, a fluorenyl group, a phenanthryl group or a triphenylenyl group.

The naphthyl group includes a 1-naphthyl group and a 2-naphthyl group.

The phenanthryl group is a 1-, 2-, 3-, 4- or 9-phenanthryl group, preferably a 2- or 9-phenanthryl group.

The triphenylenyl group is preferably a 2-triphenylenyl group.

The aromatic hydrocarbon ring having 6 to 30 ring carbon atoms is preferably a benzene, a biphenyl, a terphenyl, a naphthalene, an anthracene, a benzanthracene, a phenanthrene, a benzophenanthrene, a phenalene, a picene, a pentaphene, a pyrene, a chrysene, a benzochrysene, a fluorene, a fluoranthene, a perylene, or a triphenyl, more preferably a benzene, a biphenyl, a naphthalene or a phenanthrene.

The aromatic hydrocarbon having 6 to 30 ring carbon atoms is the same as the above-mentioned aromatic hydrocarbon ring having 6 to 30 ring carbon atoms.

In the heteroaryl group having 5 to 30 ring atoms, the ring hetero atom is selected from, for example, a nitrogen atom, a sulfur atom, and an oxygen atom. The free bond of the heteroaryl group is present on a ring carbon atom, or is present on a ring nitrogen atom if physically possible.

The heteroaryl group having 5 to 30 ring atoms is, for example, a pyrrolyl group, a furyl group, a thienyl group, a pyridyl group, an imidazopyridyl group, a pyridazinyl group, a pyrimidinyl group, a pyrazinyl group, a triazinyl group, an imidazolyl group, an oxazolyl group, a thiazolyl group, a pyrazolyl group, an isoxazolyl group, an isothiazolyl group, an oxadiazolyl group, a thiadiazolyl group, a triazolyl group, a tetrazolyl group, an indolyl group, an isoindolyl group, an indolizinyl group, a quinolizinyl group, a quinolyl group, an isoquinolyl group, a cinnolyl group, a phthalazinyl group, a quinazolinyl group, a quinoxalinyl group, a benzimidazolyl group, a benzoxazolyl group, a benzothiazolyl group, an indazolyl group, a benzoisoxazolyl group, a benzisothiazolyl group, a phenanthridinyl group, an acridinyl group, a phenanthrolinyl group, a phenazinyl group, a phenothiazinyl group, a phenoxazinyl group, a xanthenyl group, a benzofuranyl group, an isobenzofuranyl group, a naphthobenzofuranyl group, a dibenzofuranyl group, a benzothiophenyl group (a benzothienyl group, hereinafter the same), an isobenzothiophenyl group (an isobenzothienyl group, hereinafter the same), a naphthobenzothiophenyl group (a naphthobenzothienyl group, hereinafter the same), a dibenzothiophenyl group (a dibenzothienyl group, hereinafter the same), or a carbazolyl group.

A benzofuranyl group, an isobenzofuranyl group, a naphthobenzofuranyl group, a dibenzofuranyl group, a benzothiophenyl group, an isobenzothiophenyl group, a naphthobenzothiophenyl group, a dibenzothiophenyl group, or a carbazolyl group (a 9-carbazolyl group, or a 1-, 2-, 3- or 4-carbazolyl group) is preferred.

The aromatic heterocyclic compound having 5 to 30 ring atoms is preferably a pyrrole, a furan, a thiophene, a pyridine, a pyridazine, a pyrimidine, a pyrazine, a triazine, an imidazole, an oxazole, a thiazole, a pyrazole, an isoxazole, an isothiazole, an oxadiazole, a thiadiazole, a triazole, a tetrazole, an indole, an isoindole, a benzofuran, an isobenzofuran, a benzothiophene, an isobenzothiophene, an indolizine, a quinolidine, a quinoline, an isoquinoline, a cinnoline, a phthalazine, a quinazoline, a quinoxaline, a benzimidazole, a benzoxazole, a benzothiazole, an indazole, a benzisoxazole, a benzisothiazole, a dibenzofuran, a dibenzothiophene, a carbazole, a phenanthridine, an acridine, a phenanthroline, a phenazine, a phenothiazine, a phenoxazine, a xanthene or a benzonitrile, more preferably a pyridine, a dibenzofuran, a dibenzothiophene, a carbazole or a benzonitrile.

The hetero ring having 5 to 30 ring atoms preferably has a structure derived from the above-mentioned aromatic heterocyclic compound having 5 to 30 ring atoms by removing the benzene ring from the compound. Details thereof will be described below.

The alkyl group having 1 to 50 carbon atoms is preferably an alkyl group having 1 to 18 carbon atoms, more preferably an alkyl group having 1 to 8 carbon atoms. Examples of the alkyl group having 1 to 50 carbon atoms include a methyl group, an ethyl group, an n-propyl group, an isopropyl group, an n-butyl group, an isobutyl group, an s-butyl group, a t-butyl group, a pentyl group (including isomer groups), a hexyl group (including isomer groups), a heptyl group (including isomer groups), an octyl group (including isomer groups), a nonyl group (including isomer groups), a decyl group (including isomer groups), an undecyl group (including isomer groups), and a dodecyl group (including isomer groups). Among these, a methyl group, an ethyl group, an n-propyl group, an isopropyl group, an n-butyl group, an isobutyl group, an s-butyl group, a t-butyl group and a pentyl group (including isomer groups) are preferred, a methyl group, an ethyl group, an n-propyl group, an isopropyl group, an n-butyl group, an isobutyl group, an s-butyl group and a t-butyl group are more preferred, and a methyl group, an ethyl group, an isopropyl group and a t-butyl group are even more preferred.

Examples of the cycloalkyl group having 5 to 50 ring carbon atoms include a cyclopentyl group, a cyclohexyl group, a cycloheptyl group, a cyclooctyl group, and an adamantyl group. Among these, a cyclopentyl group and a cyclohexyl group are preferred.

Examples of the aliphatic hydrocarbon ring having 5 to 50 ring carbon atoms include a cyclopentene ring, a cyclopentadiene ring, a cyclohexene ring, a cyclohexadiene ring, and an aliphatic ring to be formed by partially hydrogenating the above-mentioned aromatic hydrocarbon ring having 6 to 30 ring carbon atoms.

An arbitrary substituent to be meant by the wording "substituted or unsubstituted" is, unless otherwise specifically indicated, selected from the group consisting of a halogen atom; a cyano group; a nitro group; an alkyl group having 1 to 30, preferably 1 to 18, more preferably 1 to 8 carbon atoms; a cycloalkyl group having 3 to 30, preferably 3 to 10, more preferably 3 to 8, even more preferably 5 or 6 ring carbon atoms; an aryl group having 6 to 30, preferably 6 to 25, more preferably 6 to 18 ring carbon atom; an aralkyl group having 7 to 36, preferably 7 to 26, more preferably 7 to 20 carbon atoms; an alkoxy group having 1 to 30, preferably 1 to 18, more preferably 1 to 8 carbon atoms; an aryloxy group having 6 to 30, more preferably 6 to 25, even more preferably 6 to 18 ring carbon atoms; a mono-, di- or tri-substituted silyl group having substituent(s) selected from an alkyl group having 1 to 30, preferably 1 to 18, more preferably 1 to 8 carbon atoms and an aryl group having 6 to 30, preferably 6 to 25 more preferably 6 to 18 ring carbon atoms; a haloalkyl group having 1 to 30, preferably 1 to 18, more preferably 1 to 8 carbon atoms; a haloalkoxy group having 1 to 30, preferably 1 to 18, more preferably 1 to 8 carbon atoms; and a heteroaryl group having 5 to 30, preferably 5 to 24, more preferably 5 to 13 ring atoms.

The arbitrary substituent is preferably selected from the group consisting of an alkyl group having 1 to 30 carbon atoms, a cycloalkyl group having 3 to 30 ring carbon atoms, an aryl group having 6 to 30 ring carbon atoms, a mono-, di- or tri-substituted silyl group having substituent(s) selected from an alkyl group having 1 to 30 carbon atoms and an aryl group having 6 to 30 ring carbon atoms, and a heteroaryl group having 5 to 30 ring atoms; more preferably selected from the group consisting of an alkyl group having 1 to 30 carbon atoms, an aryl group having 6 to 30 ring carbon atoms, and a heteroaryl group having 5 to 30 ring atoms; even more preferably an alkyl group having 1 to 30 carbon atoms or an aryl group having 6 to 30 ring carbon atoms; and especially more preferably an alkyl group having 1 to 30 carbon atoms.

$R^1$ to $R^{24}$ each independently represent a hydrogen atom or a substituent, and the substituent is a substituted or unsubstituted aryl group having 6 to 30 ring carbon atoms, a substituted or unsubstituted heteroaryl group having 5 to 30 ring atoms, a substituted or unsubstituted alkyl group having 1 to 50 carbon atoms, a substituted or unsubstituted cycloalkyl group having 5 to 50 ring carbon atoms, or a cyano group. $R^1$ to $R^{24}$ are preferably hydrogen atoms.

Here, details of the aryl group having 6 to 30 ring carbon atoms, a heteroaryl group having 5 to 30 ring atoms, the alkyl group having 1 to 50 carbon atoms, the cycloalkyl group having 5 to 50 ring carbon atoms, and the arbitrary substituent to be meant by the wording "substituted or unsubstituted" are as mentioned above.

At least one pair of $R^{31}$ and $R^{32}$, $R^{32}$ and $R^{33}$, $R^{33}$ and $R^{34}$, and $R^{34}$ and $R^{35}$ each independently bond to each other to form a substituted or unsubstituted aromatic hydrocarbon ring having 6 to 30 ring carbon atoms, a substituted or unsubstituted hetero ring having 5 to 30 ring atoms, or a substituted or unsubstituted aliphatic hydrocarbon ring having 5 to 50 ring carbon atoms, or $R^{31}$ and $R^{32}$, $R^{32}$ and $R^{33}$, $R^{33}$ and $R^{34}$, and $R^{34}$ and $R^{35}$ do not bond to form a ring, and in the case where they do not bond to form a ring, $R^{31}$ to $R^{35}$ each independently represent a hydrogen atom or a substituent, and the substituent is a substituted or unsubstituted aryl group having 6 to 30 ring carbon atoms, a substituted or unsubstituted heteroaryl group having 5 to 30 ring atoms, a substituted or unsubstituted alkyl group having 1 to 50 carbon atoms, a substituted or unsubstituted cycloalkyl group having 5 to 50 ring carbon atoms, or a cyano group. Preferably, $R^{31}$ to $R^{35}$ are hydrogen atoms.

Here, details of the aromatic hydrocarbon ring having 6 to 30 ring carbon atoms, the hetero ring having 5 to 30 ring atoms, the aliphatic hydrocarbon ring having 5 to 50 ring carbon atoms, the aryl group having 6 to 30 ring carbon atoms, a heteroaryl group having 5 to 30 ring atoms, the alkyl group having 1 to 50 carbon atoms, the cycloalkyl group having 5 to 50 ring carbon atoms, and details of the arbitrary substituent to be meant by the wording "substituted or unsubstituted" are as mentioned above.

Preferably, the hetero ring having 5 to 30 ring atoms constitutes the same structure as that of the above-mentioned aromatic heterocyclic compound, by at least one pair of $R^{31}$ and $R^{32}$, $R^{32}$ and $R^{33}$, $R^{33}$ and $R^{34}$, and $R^{34}$ and $R^{35}$, and the benzene ring in the formulae (1) to (17) to which these $R^{31}$ to $R^{35}$ bond.

$A^1$ represents a substituted or unsubstituted, (n+1)-valent residue of an aromatic hydrocarbon having 6 to 30 ring carbon atoms, or a substituted or unsubstituted, (n+1)-valent residue of an aromatic heterocyclic compound having 5 to 30 ring atoms, preferably an unsubstituted (n+1)-valent residue of an aromatic hydrocarbon having 6 to 30 ring carbon atoms, or an unsubstituted (n+1)-valent residue of an aromatic heterocyclic compound having 5 to 30 ring atoms.

Here, the aromatic hydrocarbon having 6 to 30 ring carbon atoms, the aromatic heterocyclic compound having 5 to 30 ring atoms, and details of the arbitrary substituent to be meant by the wording "substituted or unsubstituted" are as mentioned above.

$A^2$ each independently represents a substituted or unsubstituted aryl group having 6 to 30 ring carbon atoms, a substituted or unsubstituted heteroaryl group having 5 to 30 ring atoms or a cyano group, preferably an unsubstituted aryl group having 6 to 30 ring carbon atoms, an unsubstituted heteroaryl group having 5 to 30 ring atoms or a cyano group, more preferably an unsubstituted aryl group having 6 to 30 ring carbon atoms or an unsubstituted heteroaryl group having 5 to 30 ring atoms.

Here, the aryl group having 6 to 30 ring carbon atoms, the heteroaryl group having 5 to 30 ring atoms, and details of the arbitrary substituent to be meant by the wording "substituted or unsubstituted" are as mentioned above.

n represents an integer of 0 to 3, preferably 0 or 1, more preferably 1.

In the case where $A^1$ is an (n+1)-valent residue of benzene, n is an integer of 1 or more. When n is 0, $(A^2)_0$ is a hydrogen atom.

In the above-mentioned formula (1) to formula (17), preferably, $R^1$ to $R^{24}$ and $R^{31}$ to $R^{35}$ are hydrogen atoms, $A^1$ is an unsubstituted (n+1)-valent residue of an aromatic hydrocarbon having 6 to 30 ring carbon atoms, or an unsubstituted (n+1)-valent residue of an aromatic heterocyclic compound having 5 to 30 ring atoms, $A^2$ is an unsubstituted aryl group having 6 to 30 ring carbon atoms, or an unsubstituted heteroaryl group having 5 to 30 ring atoms.

In the formula (2), $R^1$ to $R^{24}$ and $R^{31}$ to $R^{35}$ are the same as above.

$R^{41}$ to $R^{42}$ each are independently the same as $R^1$.

m represents 0 or 1, preferably 0.

When m is 0, X is absent, and the two benzene rings are not crosslinked.

When m is 1, X is O or S.

p represents an integer of 0 to 5, preferably 0 or 1, more preferably 0.

q represents an integer of 0 to 4, preferably 0 or 1, more preferably 0.

In the formula (3), $R^1$ to $R^{24}$ and $R^{31}$ to $R^{35}$ are the same as above.

$A^2$ and n are the same as above.

$R^{43}$ is the same as $R^1$.

u represents an integer of 0 to (5-n), preferably 0 or 1, more preferably 0.

In the formula (4), $R^1$ to $R^{24}$ and $R^{31}$ to $R^{35}$ are the same as above.

$R^{44}$ represents a hydrogen atom or a cyano group, preferably a hydrogen atom.

Y represents CH or N, preferably CH.

Z represents CH or N, preferably CH.

v and w each independently represent 0 or 1, preferably at least one of v and w is 0 and the other is 0 or 1, more preferably both are 0.

In the formula (5), $R^1$ to $R^{24}$ and $R^{31}$ to $R^{35}$ are the same as above.

$R^{45}$ to $R^{49}$ are the same as $R^1$.

In the formula (6), $R^1$ to $R^{24}$ and $R^{31}$ to $R^{35}$ are the same as above.

One of $R^{51}$ to $R^{55}$ is a single bond bonding to a*, and $R^{51}$ to $R^{55}$ not bonding to a* each are independently the same as $R^1$.

$R^{56}$ to $R^{60}$ each are independently the same as $R^1$.

In the formula (7), $R^1$ to $R^{24}$ and $R^{31}$ to $R^{35}$ are the same as above.

One of $R^{51}$ to $R^{55}$ is a single bond bonding to b*, and $R^{51}$ to $R^{55}$ not bonding to b* each are independently the same as $R^1$.

One of $R^{61}$ to $R^{65}$ is a single bond bonding to c*, and $R^{61}$ to $R^{65}$ not bonding to c* each are independently the same as $R^1$.

In the formula (8), $R^1$ to $R^{24}$ and $R^{31}$ to $R^{35}$ are the same as above.

One of $R^{61}$ to $R^{65}$ is a single bond bonding to d*, and $R^{61}$ to $R^{65}$ not bonding to d* each are independently the same as $R^1$.

In the formula (9), $R^1$ to $R^{24}$ and $R^{31}$ to $R^{35}$ are the same as above.

One of $R^{71}$ to $R^{78}$ is a single bond bonding to e*, and $R^{71}$ to $R^{78}$ not bonding to e* each are independently the same as $R^1$.

In the formula (10), $R^1$ to $R^{24}$ and $R^{31}$ to $R^{35}$ are the same as above.

One of $R^{71}$ to $R^{78}$ is a single bond bonding to e*, and $R^{71}$ to $R^{78}$ not bonding to e* each are independently the same as $R^1$.

In the formula (11), $R^1$ to $R^{24}$ and $R^{31}$ to $R^{35}$ are the same as above.

One of $R^{81}$ to $R^{88}$ is a single bond bonding to f*, and $R^{81}$ to $R^{88}$ not bonding to f* each are independently the same as $R^1$.

In the formula (12), $R^1$ to $R^{24}$ and $R^{31}$ to $R^{35}$ are the same as above.

One of $R^{81}$ to $R^{88}$ is a single bond bonding to g*, one of $R^{81}$ to $R^{88}$ is a single bond bonding to h*, and $R^{81}$ to $R^{88}$ not bonding to g* and h* each are independently the same as $R^1$.

$R^{89}$ to $R^{93}$ each are independently the same as $R^1$.

In the formula (13), $R^1$ to $R^{24}$ and $R^{31}$ to $R^{35}$ are the same as above.

One of $R^{51}$ to $R^{55}$ is a single bond bonding to i*, and $R^{51}$ to $R^{55}$ not bonding to i* each are independently the same as $R^1$.

One of $R^{81}$ to $R^{88}$ is a single bond bonding to j*, and $R^{81}$ to $R^{88}$ not bonding to j* each are independently the same as $R^1$.

In the formula (14), $R^1$ to $R^{24}$ and $R^{31}$ to $R^{35}$ are the same as above.

One of $R^{94}$ to $R^{103}$ is a single bond bonding to k*, and $R^{94}$ to $R^{103}$ not bonding to k* each are independently the same as $R^1$.

In the formula (15), $R^1$ to $R^{24}$ and $R^{31}$ to $R^{35}$ are the same as above.

One of $R^{51}$ to $R^{55}$ is a single bond bonding to l*, and $R^{51}$ to $R^{55}$ not bonding to l* each are independently the same as $R^1$.

One of $R^{71}$ to $R^{78}$ is a single bond bonding to m*, and $R^{71}$ to $R^{78}$ not bonding to m* each are independently the same as $R^1$.

In the formula (16), $R^1$ to $R^{24}$ and $R^{31}$ to $R^{35}$ are the same as above.

One of $R^{51}$ to $R^{55}$ is a single bond bonding to n*, and $R^{51}$ to $R^{55}$ not bonding to n* each are independently the same as $R^1$.

One of $R^{71}$ to $R^{78}$ is a single bond bonding to o*, and $R^{71}$ to $R^{78}$ not bonding to o* each are independently the same as $R^1$.

In the formula (17), $R^1$ to $R^{24}$ and $R^{31}$ to $R^{35}$ are the same as above.

One of $R^{51}$ to $R^{55}$ is a single bond bonding to p*, and $R^{51}$ to $R^{55}$ not bonding to p* each are independently the same as $R^1$.

$R^{111}$ to $R^{118}$ each are independently the same as $R^1$.

In the formula (1) to the formula (17), the group represented by the following formula (18) is preferably represented by any of the following formulae (a) to (l), more preferably the formula (a), (b), (e) or (i), even more preferably the formula (a), (b) or (e), further more preferably the formula (a).

(18)

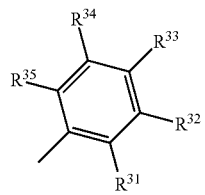

(a)

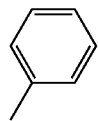

(b)

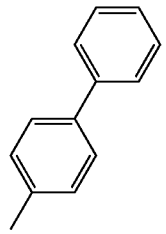

(c)

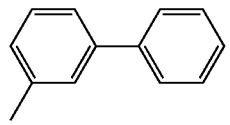

(d)

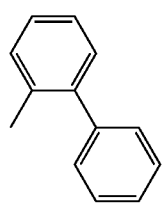

(e)

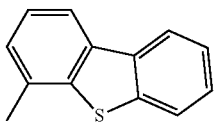

(f)

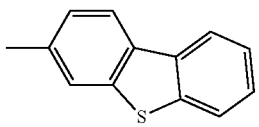

(g)

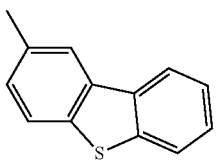

(h)

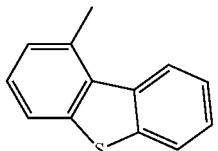

(i)

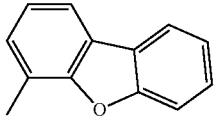

(j)

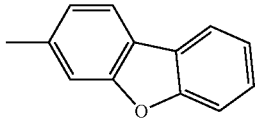

(k)

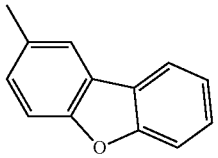

(l)

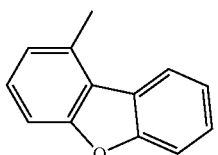

In the formula (1) to the formula (17), the group represented by $-A^1-(A^2)_n$ is preferably represented by any of the following formulae (m) to (x), more preferably the formula (m), (n), (o), (p), (q) or (r), even more preferably the formula (m) or (q).

(m) 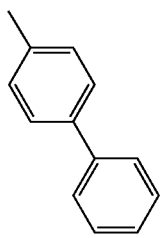

(n) 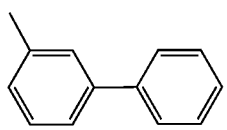

(o) 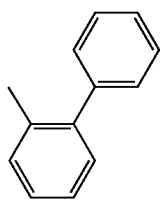

(p) 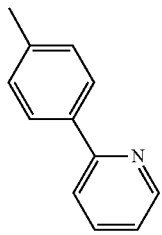

(q) 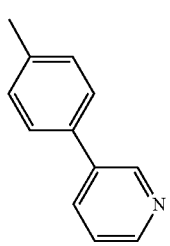

(r) 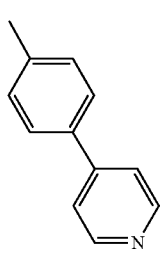

(s) 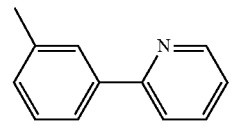

(t) 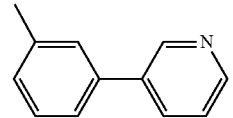

(u) 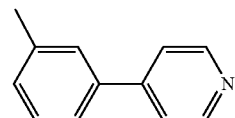

(v) 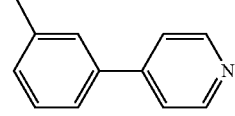

(w) 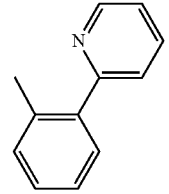

(x) 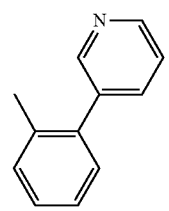

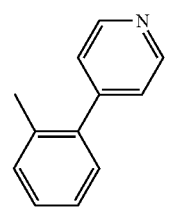

At least one hydrogen atom in the compounds represented by the formula (1) to the formula (17) may be a deuterium atom.

At least one of $R^1$ to $R^{24}$ may be a deuterium atom.

All the hydrogen atoms of $R^1$ to $R^{24}$ may be deuterium atoms. All $R^1$ to $R^{24}$ may be deuterium atoms.

The group represented by $A^1$ may have hydrogen atom(s), and at least one of the hydrogen atom(s) may be a deuterium atom.

n may be 0, the group represented by $A^1$ may be unsubstituted, and all the hydrogen atoms that the group represented by $A^1$ has may be deuterium atoms.

n may be 1, the group represented by $A^1$ may have hydrogen atoms, at least one of the hydrogen atoms may be a deuterium atom, the group represented by $A^2$ may have hydrogen atoms, and at least one of the hydrogen atoms may be a deuterium atom.

n may be 1, the group represented by $A^1$ may be unsubstituted, all hydrogen atoms that the group represented by $A^1$ has may be deuterium atoms, the group represented by $A^2$ may be unsubstituted, all hydrogen atoms that the group represented by $A^2$ has may be deuterium atoms At least one of $R^{31}$ to $R^{35}$ may be a deuterium atom.

All $R^{31}$ to $R^{35}$ may be deuterium atoms.

The compound of the present invention may be a compound represented by any of the following formulae (D1) to (D6).

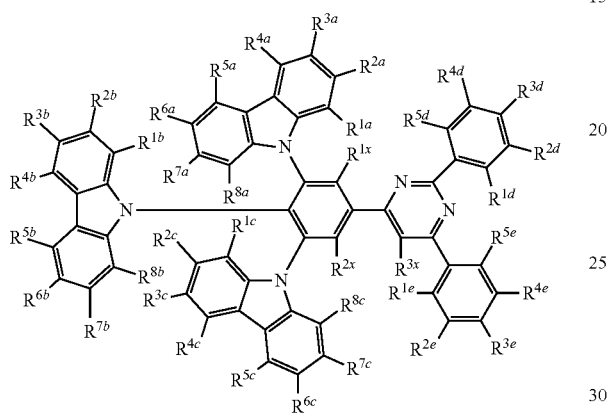

(D1)

In the formula (D1), $R^{1a}$ to $R^{8a}$, $R^{1b}$ to $R^{8b}$, $R^{1c}$ to $R^{8c}$, $R^{1d}$ to $R^{5d}$, $R^{1x}$ to $R^{3x}$, and $R^{1e}$ to $R^{5e}$ are hydrogen atoms, and 1 or more and 37 or less of the hydrogen atoms are deuterium atoms.

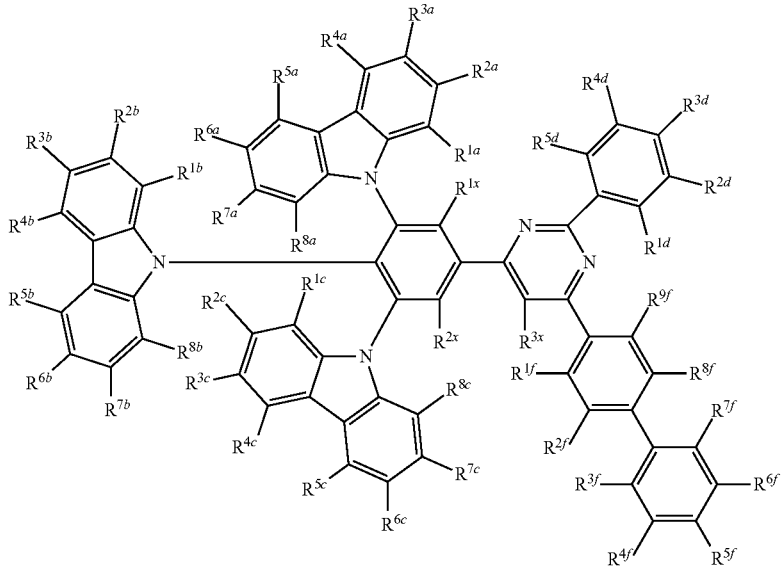

(D2)

In the formula (D2), $R^{1a}$ to $R^{8a}$, $R^{1b}$ to $R^{8b}$, $R^{1c}$ to $R^{8c}$, $R^{1d}$ to $R^{5d}$, $R^{1x}$ to $R^{3x}$, and $R^{1f}$ to $R^{9f}$ are hydrogen atoms, and 1 or more and 41 or less of the hydrogen atoms are deuterium atoms.

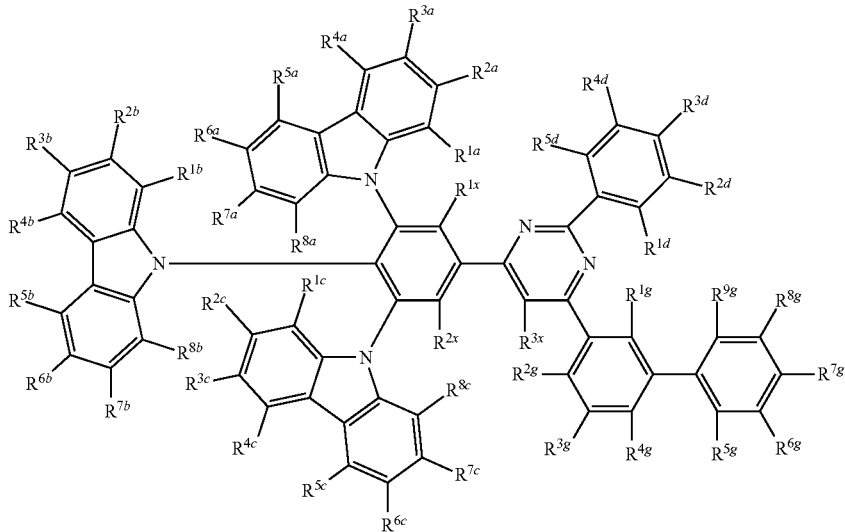

(D3)

In the formula (D3), $R^{1a}$ to $R^{8a}$, Rib to $R^{8b}$, $R^{1c}$ to $R^{8c}$, Rid to $R^{5d}$, $R^{1x}$ to $R^{3x}$, and $R^{1g}$ to $R^{9g}$ are hydrogen atoms, and 1 or more and 41 or less of the hydrogen atoms are deuterium atoms.

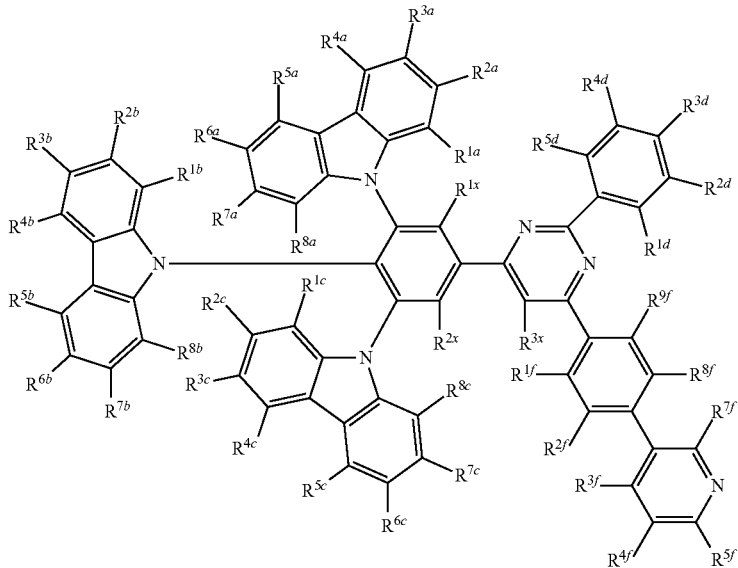

(D4)

In the formula (D4), $R^{1a}$ to $R^{8a}$, Rib to $R^{8b}$, $R^{1c}$ to $R^{8c}$, Rid to $R^{5d}$, $R^{1x}$ to $R^{3x}$, $R^{1f}$ to $R^{5f}$, and $R^{7f}$ to $R^{9f}$ are hydrogen atoms, and 1 or more and 40 or less of the hydrogen atoms are deuterium atoms.

(D5)

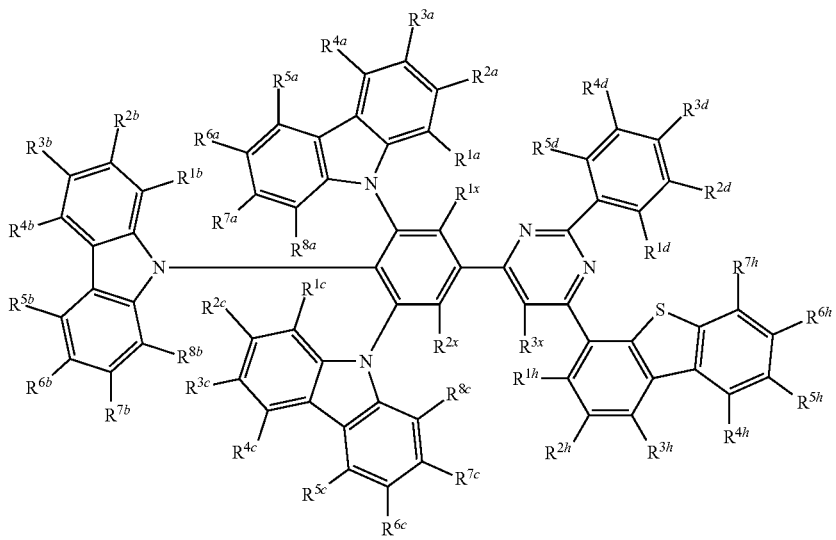

In the formula (D5), $R^{1a}$ to $R^{8a}$, $R^{1b}$ to $R^{8b}$, $R^{1c}$ to $R^{8c}$, $R^{1d}$ to $R^{5d}$, $R^{1x}$ to $R^{3x}$, and $R^{1h}$ to $R^{7h}$ are hydrogen atoms, and 1 or more and 39 or less of the hydrogen atoms are deuterium atoms.

(D6)

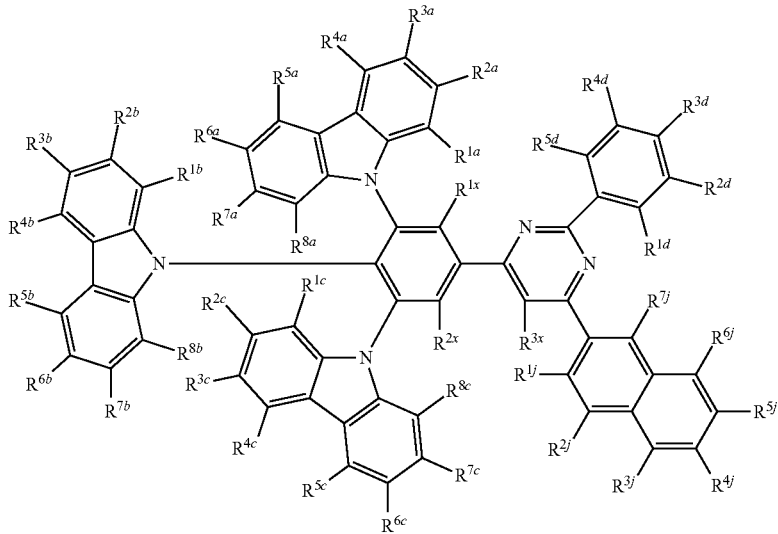

In the formula (D6), $R^{1a}$ to $R^{8a}$, $R^{1b}$ to $R^{8b}$, $R^{1c}$ to $R^{8c}$, $R^{1d}$ to $R^{5d}$, $R^{1x}$ to $R^{3x}$, and $R^{1j}$ to $R^{7j}$ are hydrogen atoms, and 1 or more and 39 or less of the hydrogen atoms are deuterium atoms.

Specific examples of the compound (specific compounds) of the present invention are mentioned below, but are not limited to these.

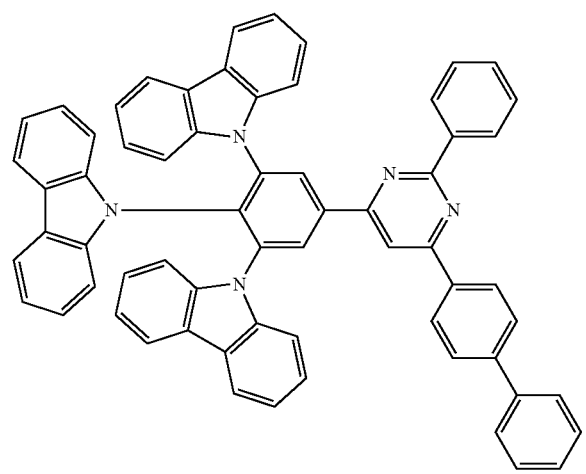
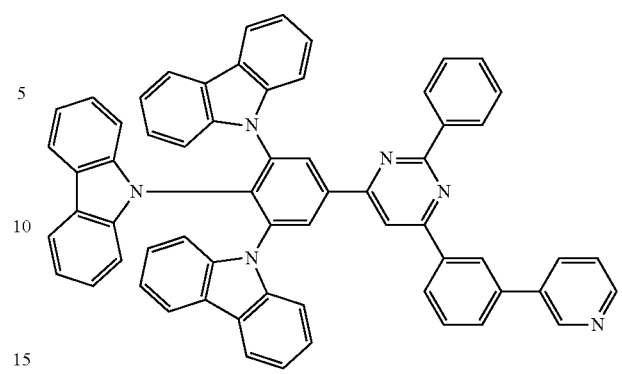
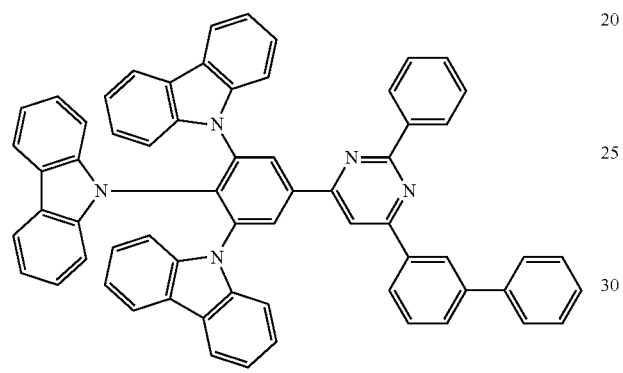
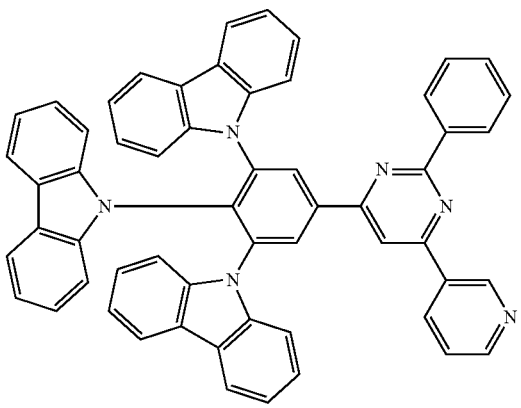
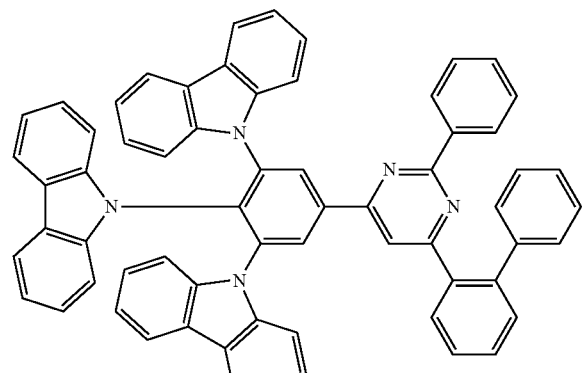
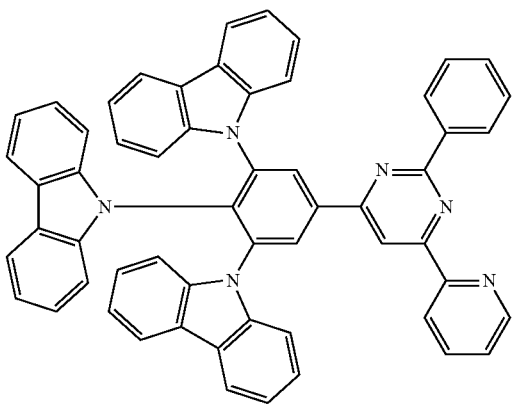
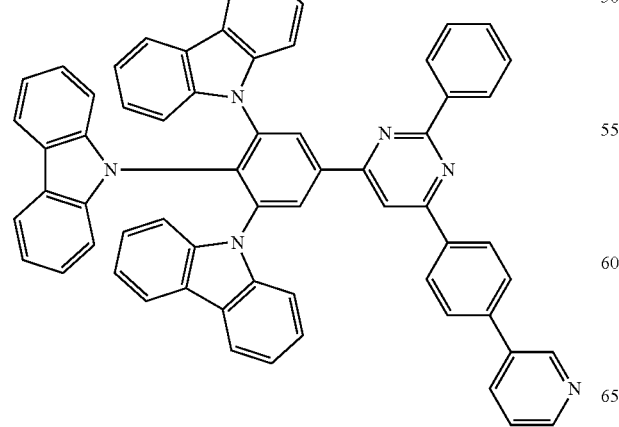
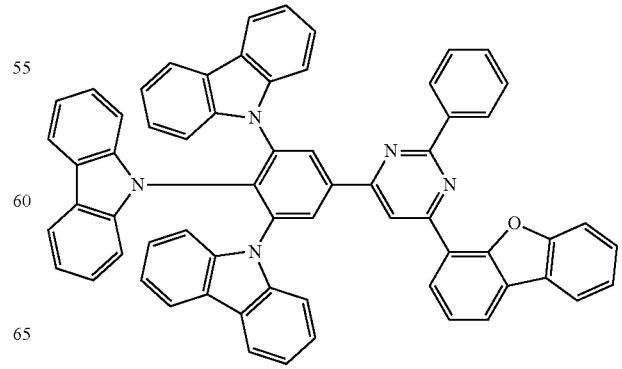

-continued
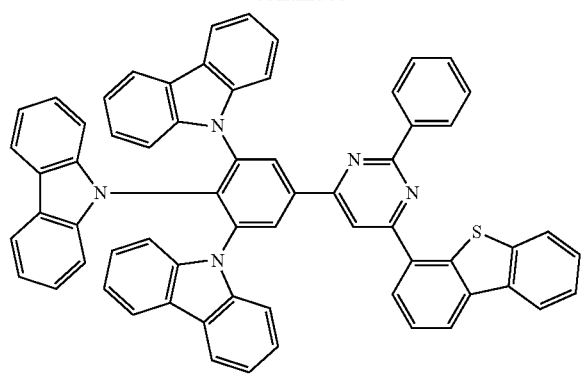
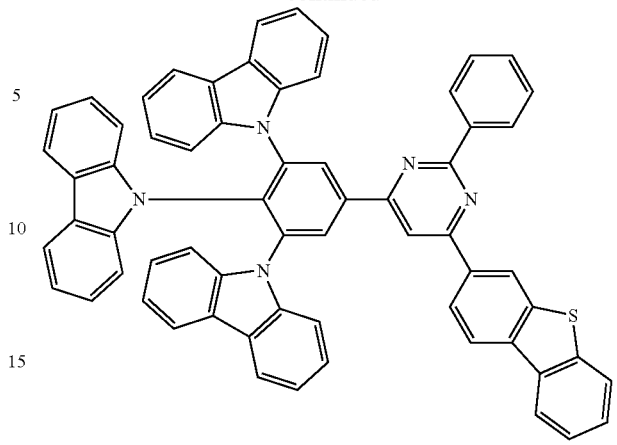
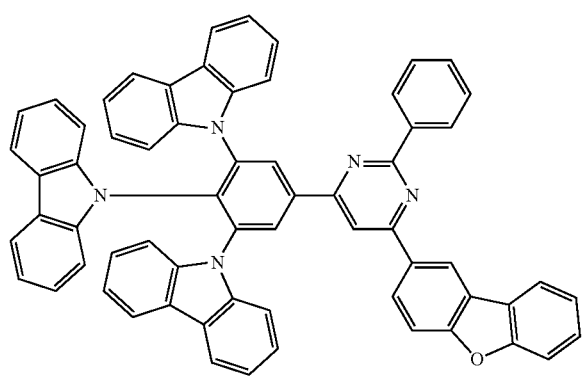
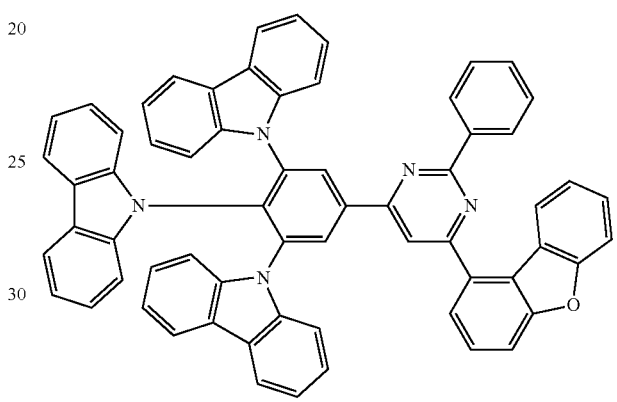
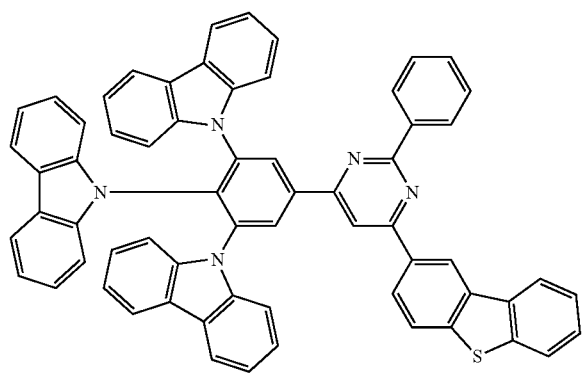
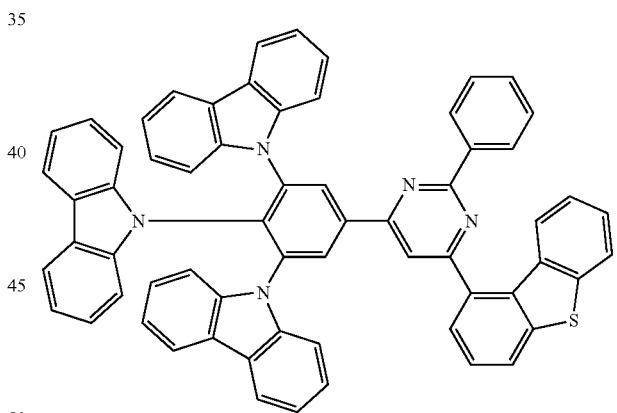
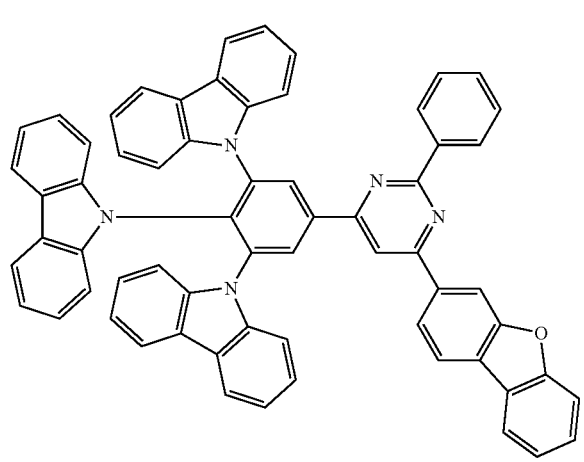
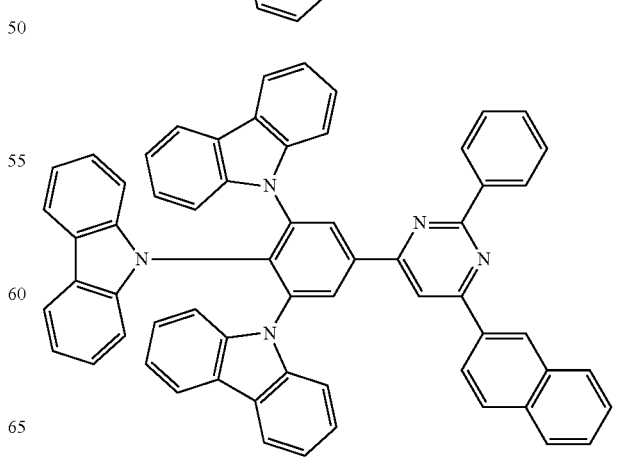

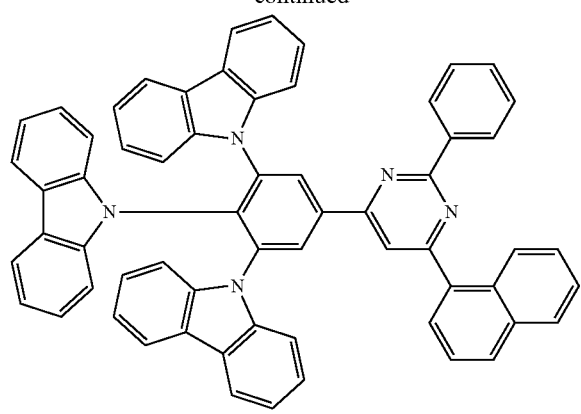
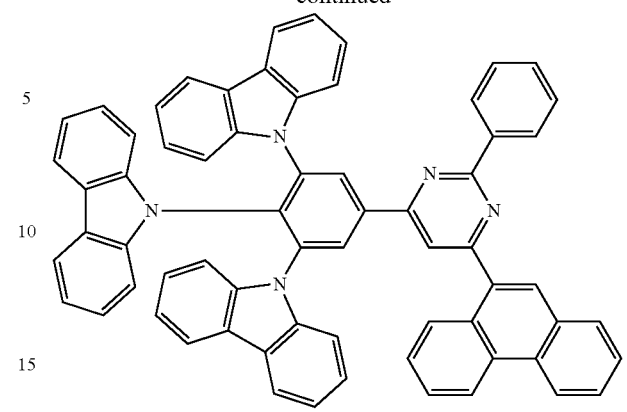
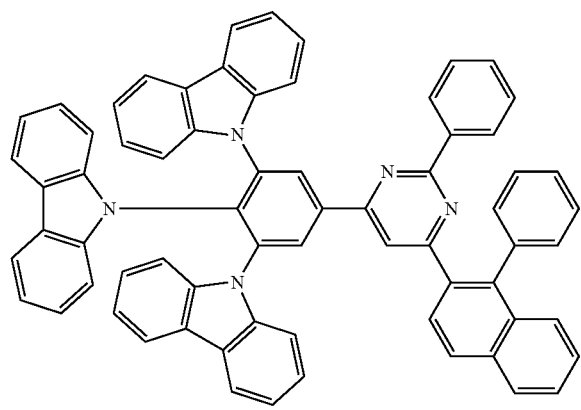
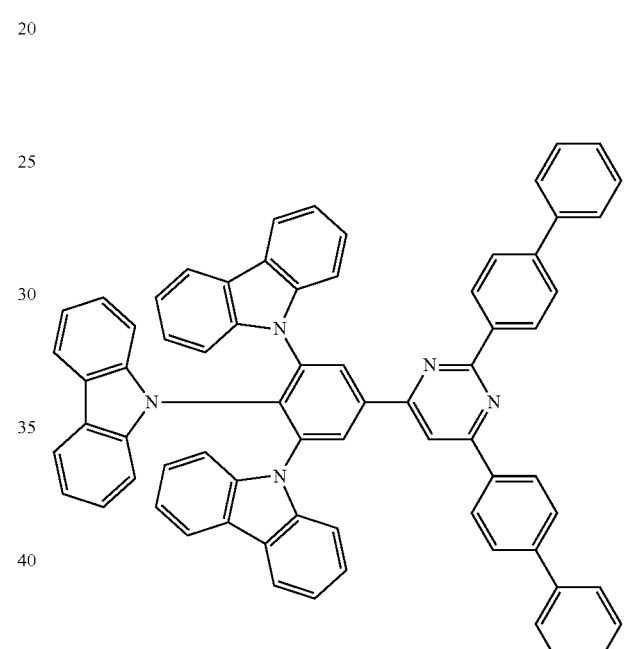
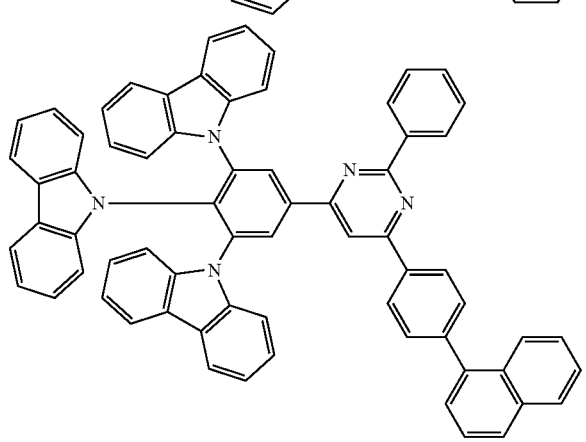
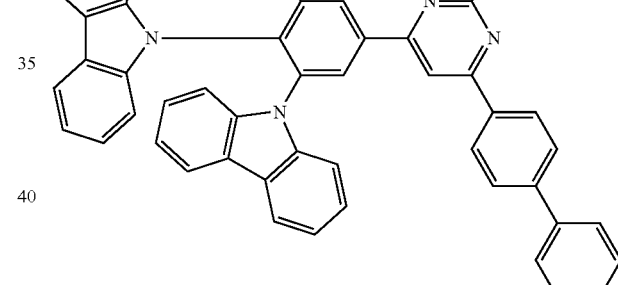
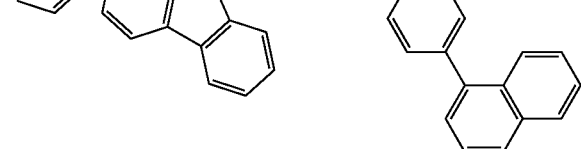
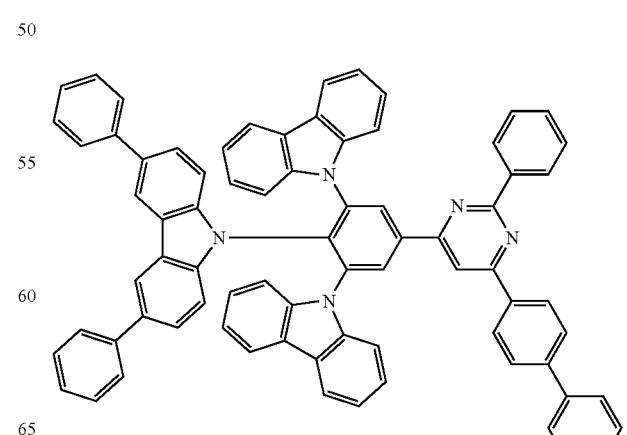

-continued
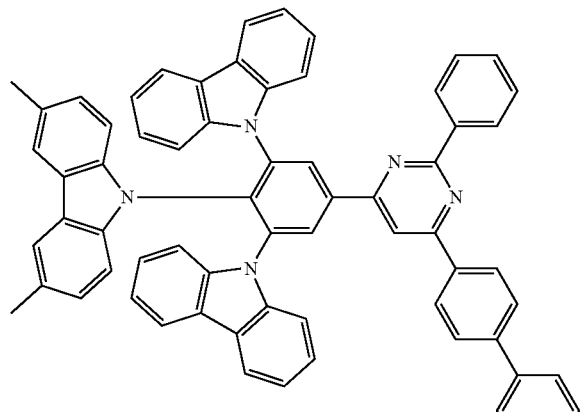
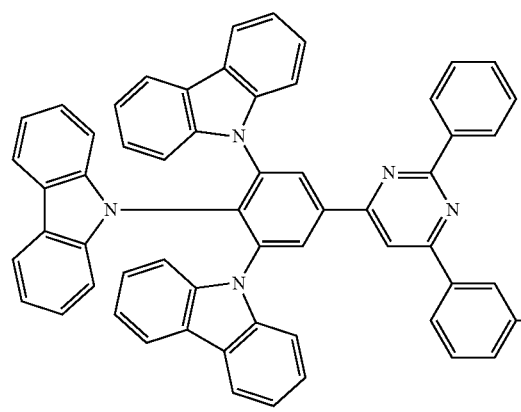
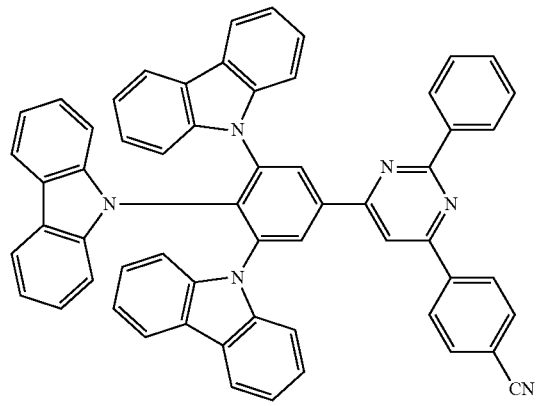
-continued
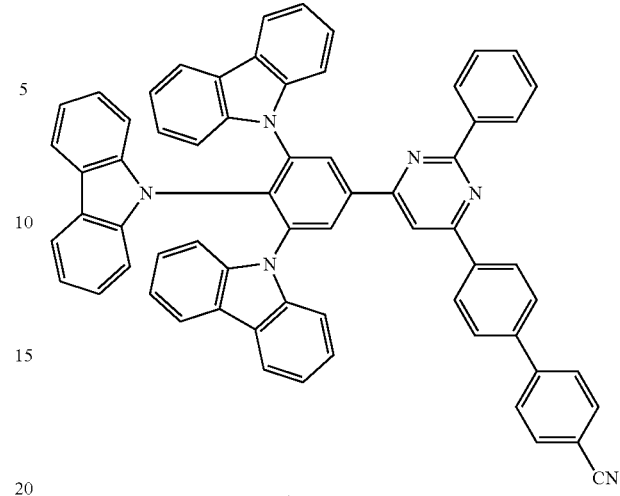
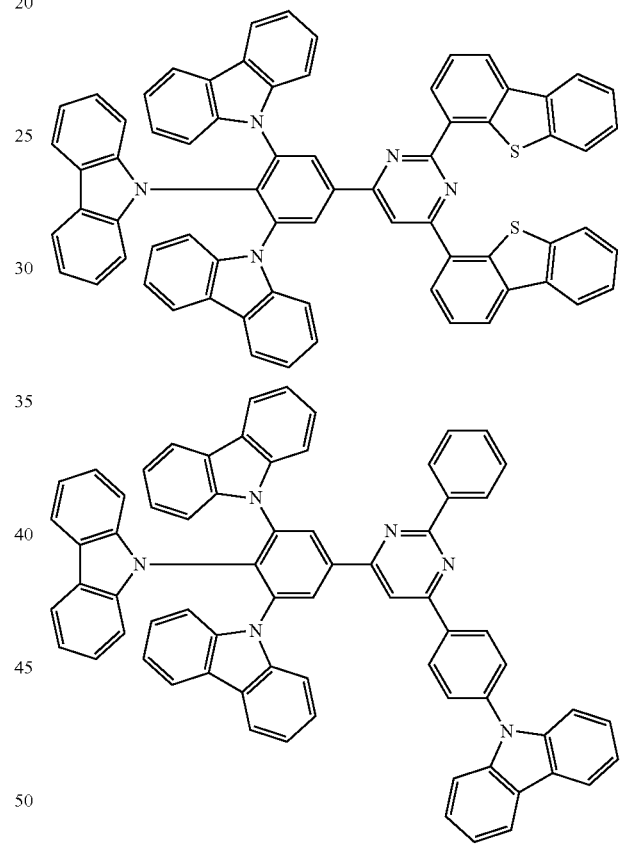
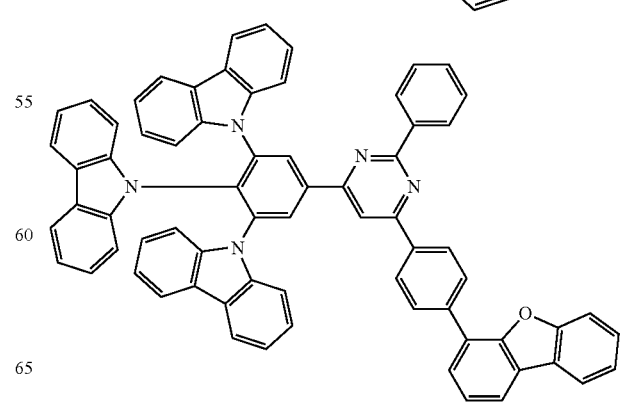

45
-continued
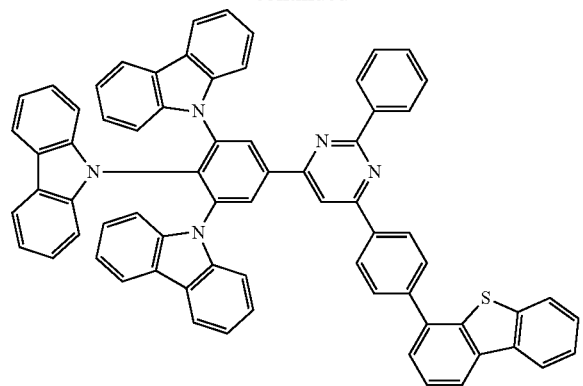
46
-continued
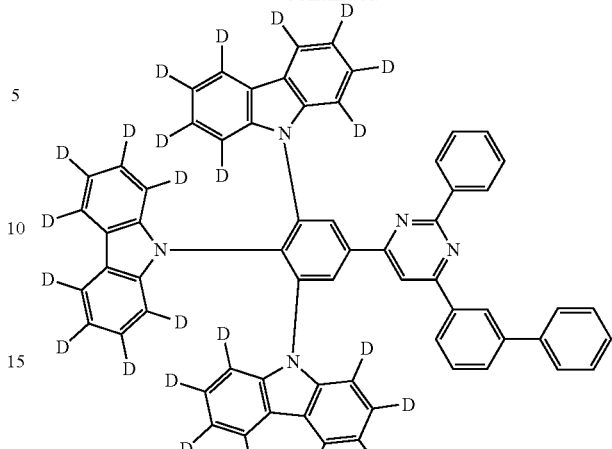
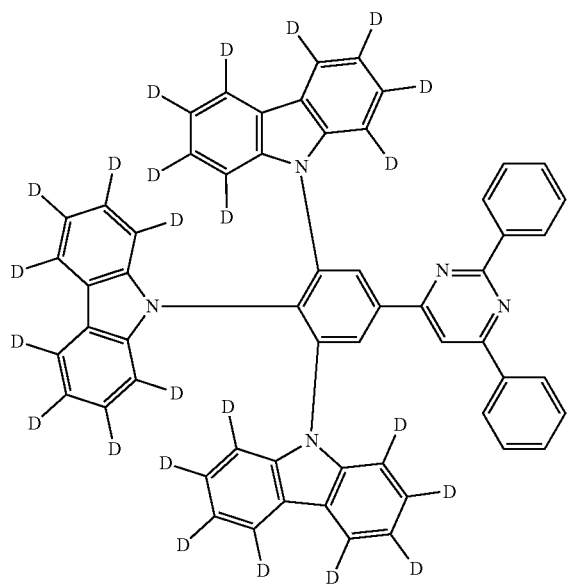
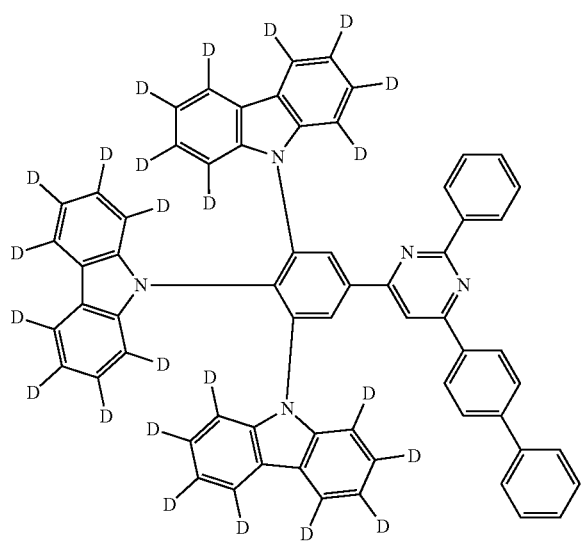
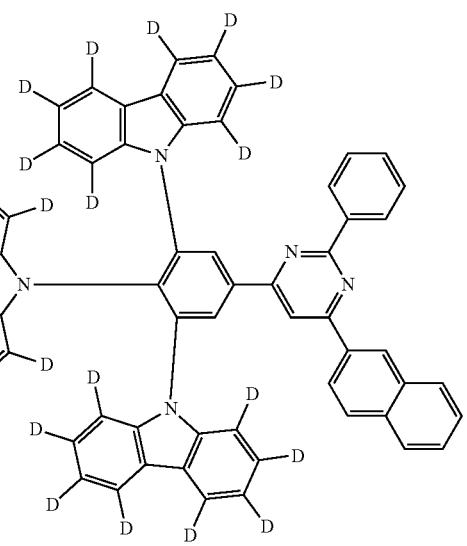

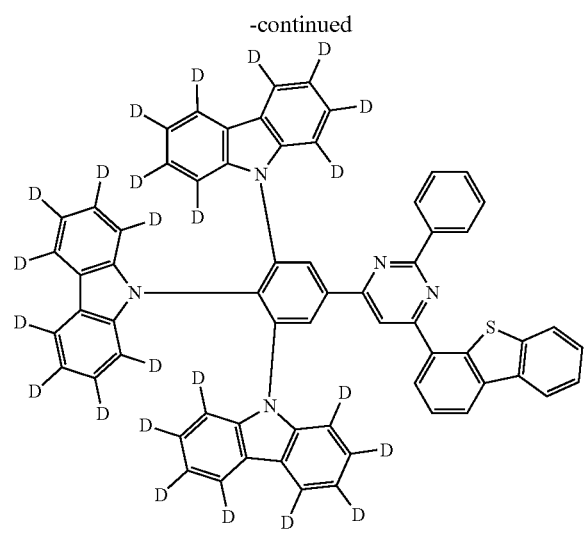
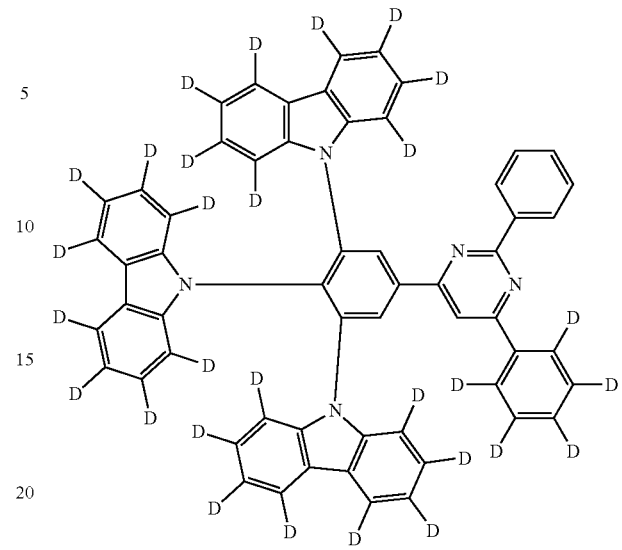
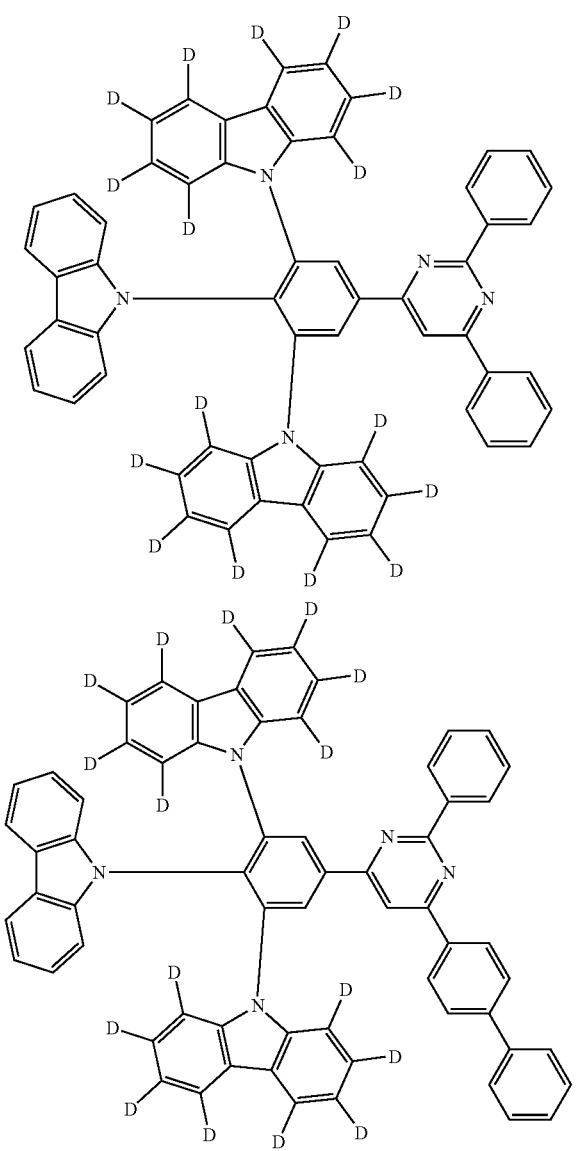
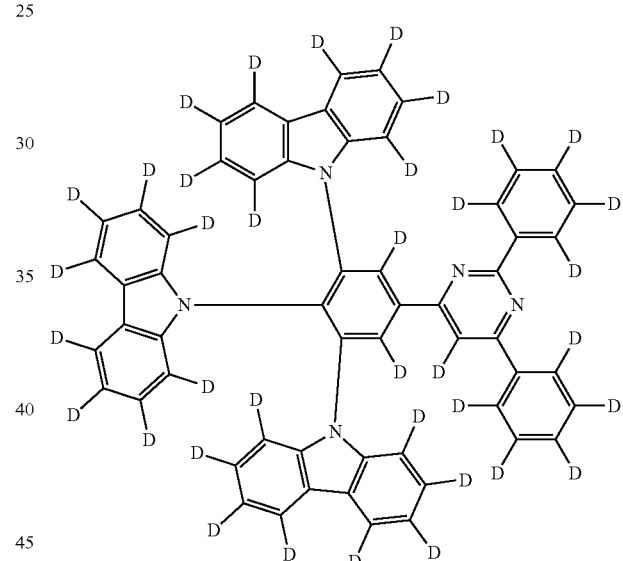
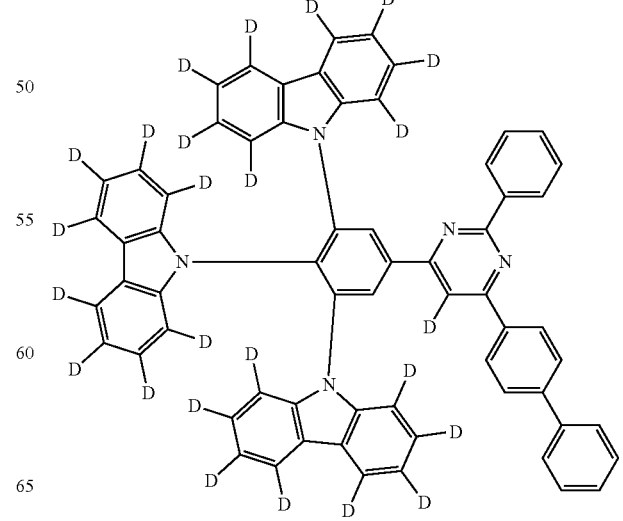

49
-continued
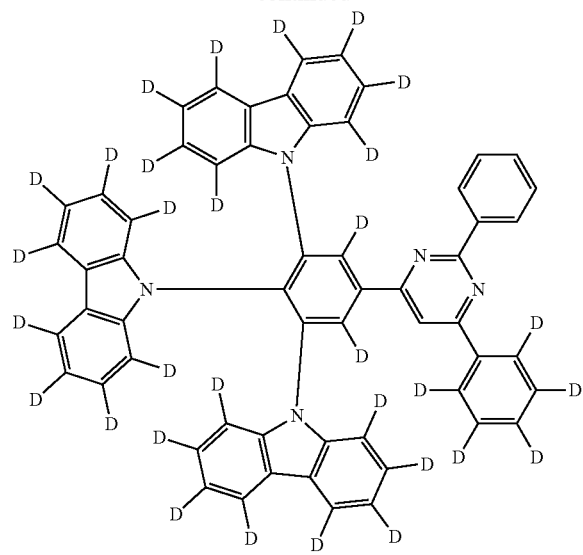
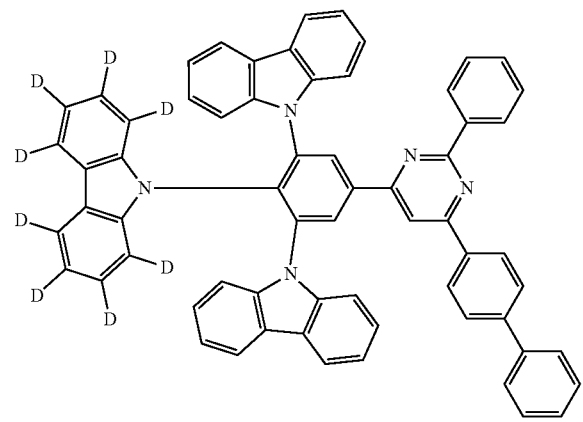
50
-continued
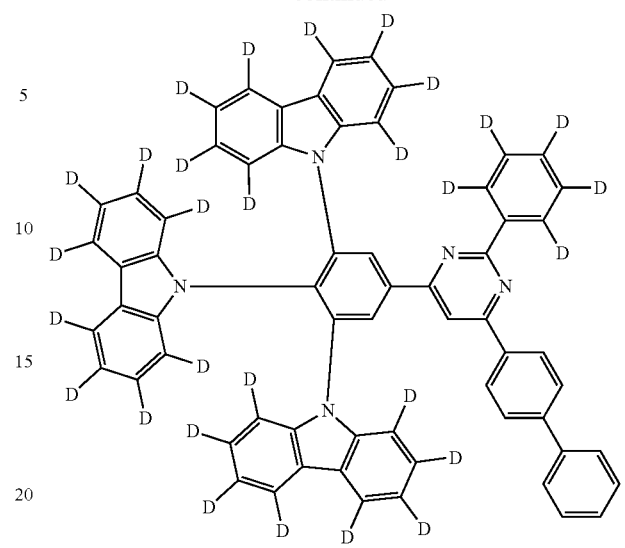
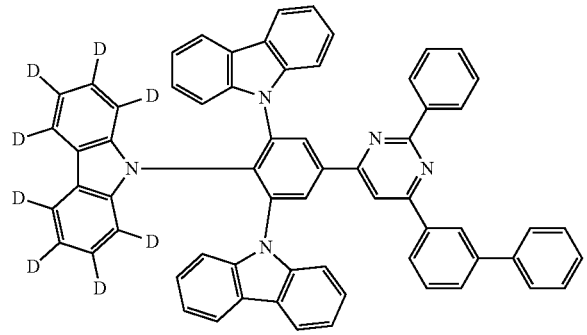
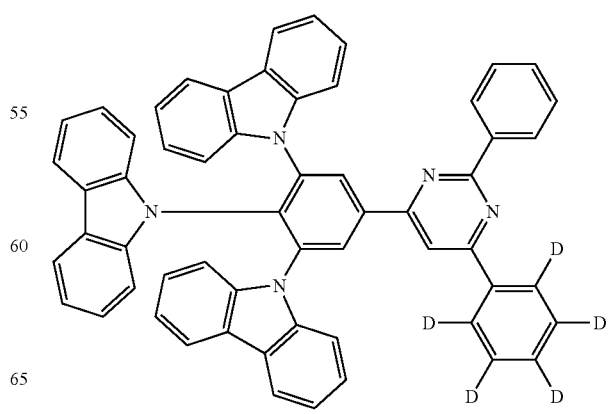

51
-continued
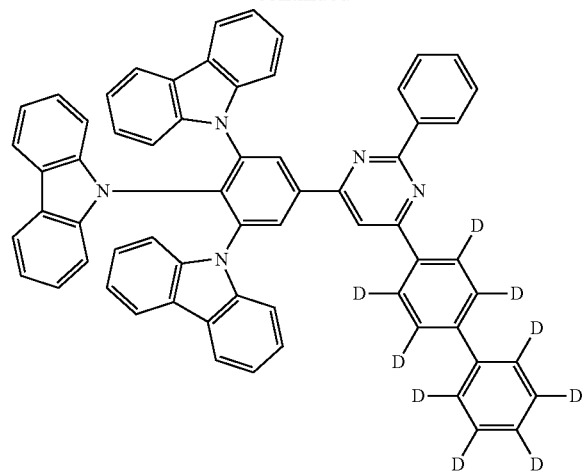
52
-continued
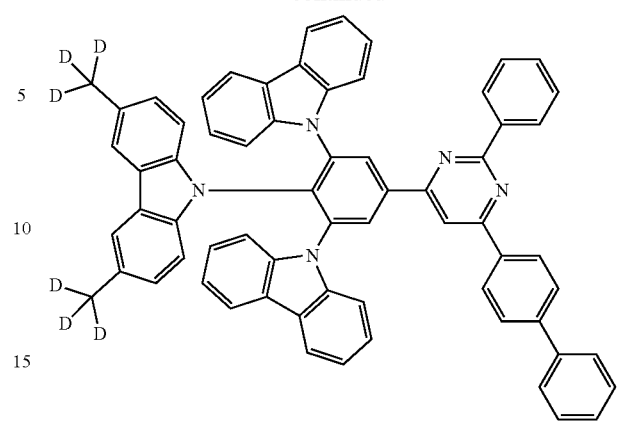
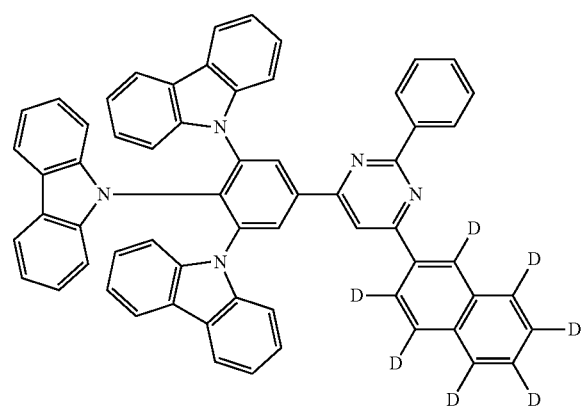
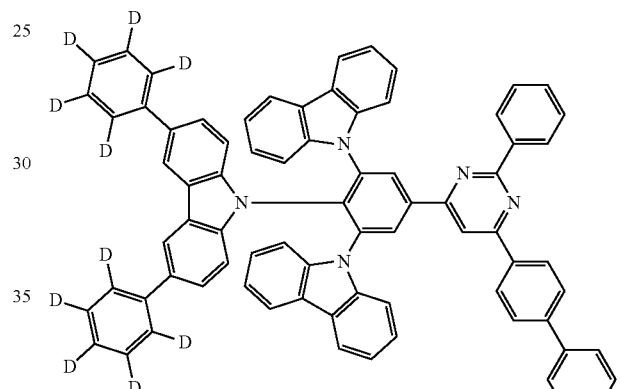
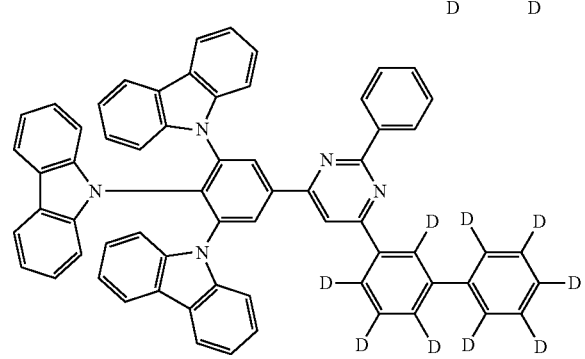
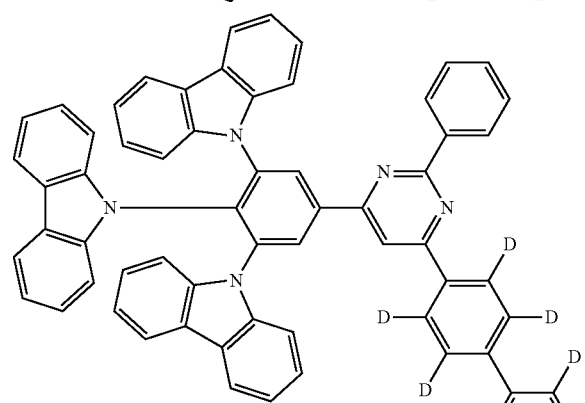
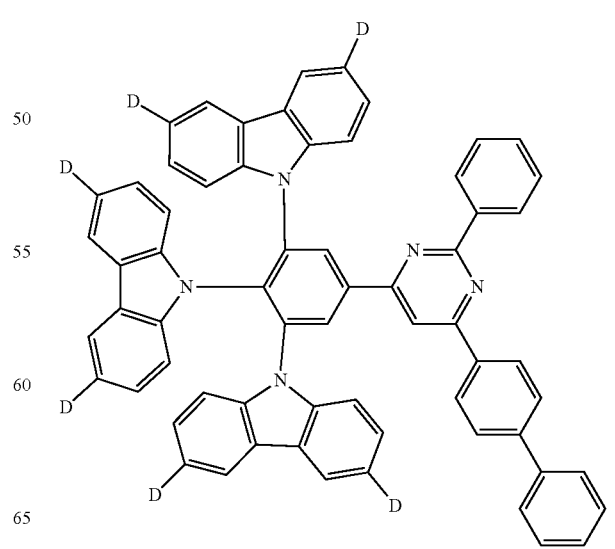

-continued
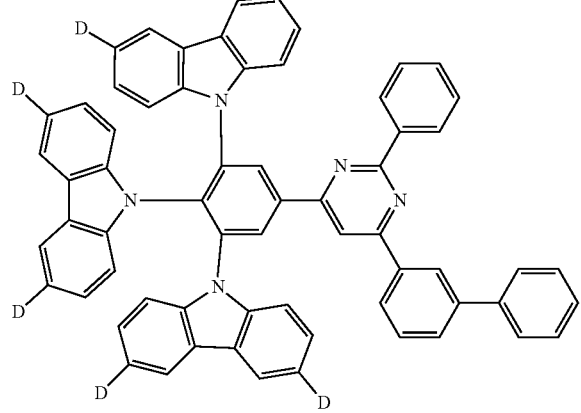
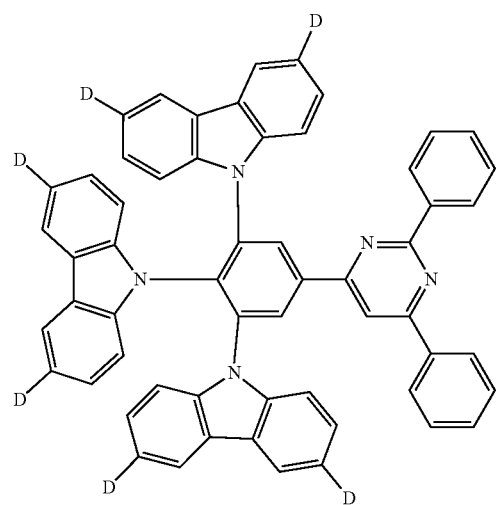
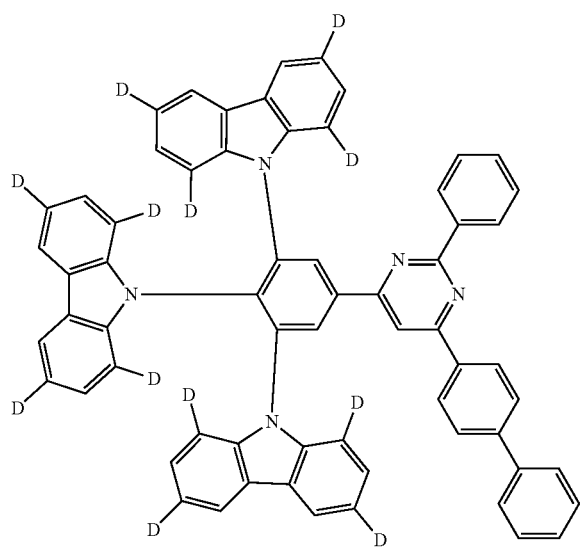
-continued
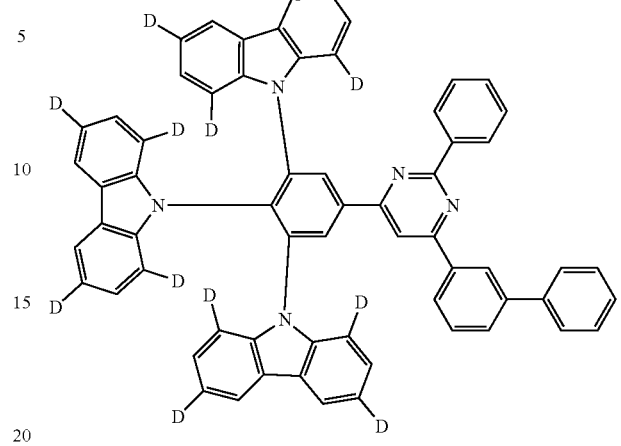
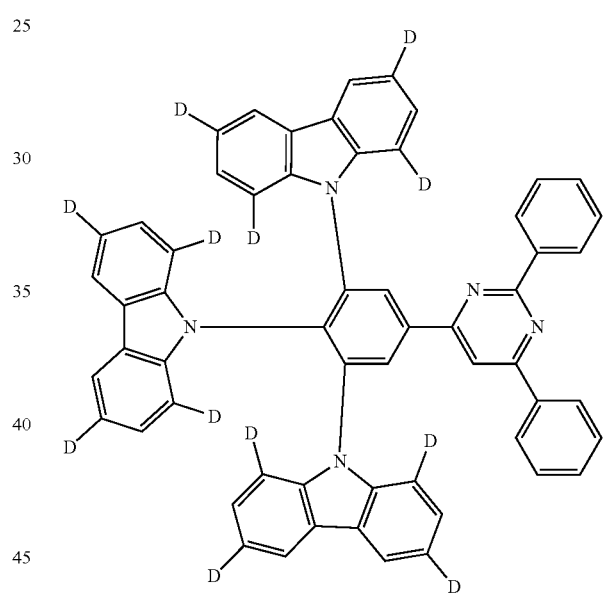
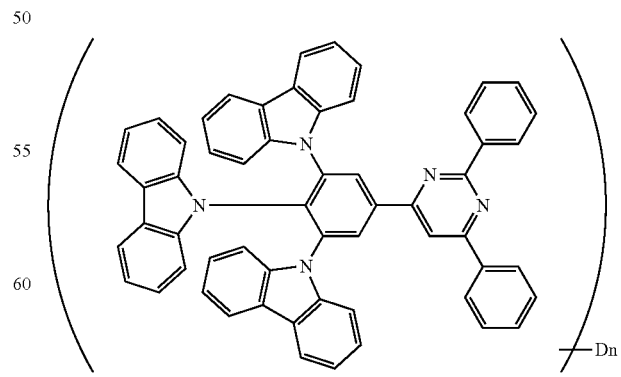
n represents the number of deuterium
atoms that the compound contains,
and is an integer of 1 to 37.

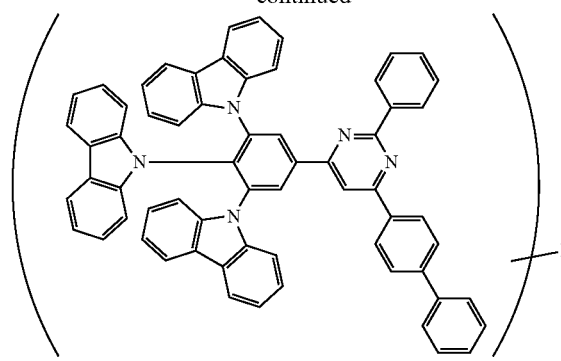

n represents the number of deuterium atoms that the compound contains, and is an integer of 1 to 41.

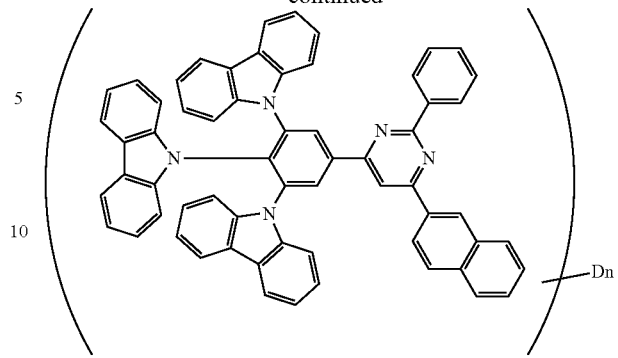

n represents the number of deuterium atoms that the compound contains, and is an integer of 1 to 39.

n represents the number of deuterium atoms that the compound contains, and is an integer of 1 to 41.

n represents the number of deuterium atoms that the compound contains, and is an integer of 1 to 40.

n represents the number of deuterium atoms that the compound contains, and is an integer of 1 to 39.

A method of producing the compound (1) is not particularly limited, and those skilled in the art may easily perform production by a method described in the following Examples, or by a method obtained by modifying the method with reference to a known synthesis method.

2. Material for Organic EL Device

The material for the organic EL device of the present invention contains the compound (1). The content of the compound (1) in the material for the organic EL device of the present invention is not particularly limited, and is, for example, 1% by mass or more (including 100%) relative to the total mass of the layer containing the compound (1), preferably 10% by mass or more (including 100%), more preferably 50% by mass or more (including 100%), further preferably 80% by mass or more (including 100%), and particularly preferably 90% by mass or more (including 100%). The material for the organic EL device of the present invention is useful in producing the organic EL device.

3. Organic EL Device

Next, the organic EL device of the present invention will be described.

3-1. Organic EL Device of First Embodiment

The organic EL device of the first embodiment of the present invention includes an anode, a cathode, and organic layers between the anode and the cathode. The organic layers include a light emitting layer, and at least one layer among the organic layers contains the compound (1) represented by the above-mentioned formula (1).

Examples of the organic layer containing the compound (1) may include a hole transporting zone (a hole injecting layer, a hole transporting layer, an electron blocking layer, an exciton blocking layer, etc.) provided between the anode and the light emitting layer, the light emitting layer, a space layer, an electron transporting zone (an electron injecting layer, an electron transporting layer, a hole blocking layer, etc.) provided between the cathode and the light emitting layer, but are not limited thereto. The compound (1) is preferably used as a material for the electron transporting zone or the light emitting layer in a fluorescent or phosphorescent EL device, more preferably as a material for the electron transporting zone, further preferably as a material for the electron transporting layer or the hole blocking layer.

3-2. Organic EL Device of Second Embodiment

The organic EL device of the second embodiment of the present invention includes an anode, a cathode, and organic layers between the anode and the cathode. The organic layers include a light emitting layer and a first layer arranged between the light emitting layer and the cathode, and the first layer contains the compound (1A) represented by the following formula (1A).

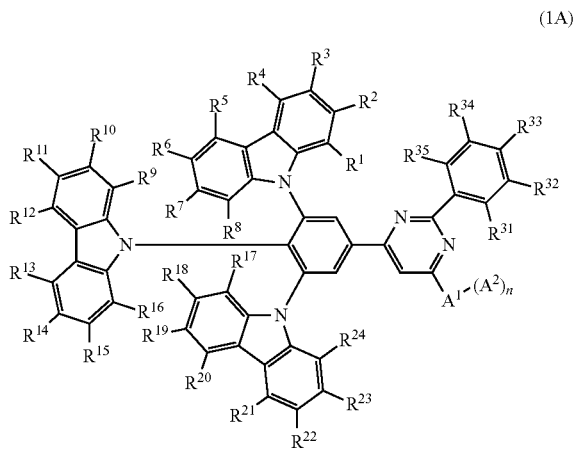

(1A)

In the formula,
$R^1$ to $R^{24}$ each independently represent a hydrogen atom, or a substituent, and the substituent is a substituted or unsubstituted aryl group having 6 to 30 ring carbon atoms, a substituted or unsubstituted heteroaryl group having 5 to 30 ring atoms, a substituted or unsubstituted alkyl group having 1 to 50 carbon atoms, a substituted or unsubstituted cycloalkyl group having 5 to 50 ring carbon atoms, or a cyano group, at least one pair of $R^{31}$ and $R^{32}$, $R^{32}$ and $R^{33}$, $R^{33}$ and $R^{34}$, and $R^{34}$ and $R^{35}$ each independently bond to each other to form a substituted or unsubstituted aromatic hydrocarbon ring having 6 to 30 ring carbon atoms, a substituted or unsubstituted hetero ring having 5 to 30 ring atoms, or a substituted or unsubstituted aliphatic hydrocarbon ring having 5 to 50 ring carbon atoms, or $R^{31}$ and $R^{32}$, $R^{32}$ and $R^{33}$, $R^{33}$ and $R^{34}$, and $R^{34}$ and $R^{35}$ do not bond to form a ring, and in the case where they do not bond to form a ring, $R^{31}$ to $R^{35}$ each independently represent a hydrogen atom or a substituent, and the substituent is a substituted or unsubstituted aryl group having 6 to 30 ring carbon atoms, a substituted or unsubstituted heteroaryl group having 5 to 30 ring atoms, a substituted or unsubstituted alkyl group having 1 to 50 carbon atoms, a substituted or unsubstituted cycloalkyl group having 5 to 50 ring carbon atoms, or a cyano group, $A^1$ represents a substituted or unsubstituted, (n+1)-valent residue of an aromatic hydrocarbon having 6 to 30 ring carbon atoms, or a substituted or unsubstituted, (n+1)-valent residue of an aromatic heterocyclic compound having 5 to 30 ring atoms, $A^2$ each independently represents a substituted or unsubstituted aryl group having 6 to 30 ring carbon atoms, a substituted or unsubstituted heteroaryl group having 5 to 30 ring atoms, or a cyano group, n represents an integer of 0 to 3, and when n is 0, $(A^2)_0$ is a hydrogen atom.

Specifically, the organic EL device of the second embodiment differs from the organic EL device of the first embodiment in point of the following difference 1 and the difference 2.

Difference 1:
In the first embodiment, the compound (1) is defined to be such that "when $A^1$ is an (n+1)-valent residue of benzene, n is an integer of 1 or more", but in the second embodiment, the compound (1A) does not have the definition.

Difference 2:
In the first embodiment, at least one organic layer contains the compound (1), but in the second embodiment, the first layer between the light emitting layer and the cathode contains the compound (1A) among the organic layers.

Specifically, regarding the difference 1, in the case where $A^1$ is an (n+1)-valent residue of benzene in the compound (1A) in the second embodiment, n may be an integer of 1 or more, and n may be 0. However, in the case where $A^1$ is an (n+1)-valent residue of benzene, n is preferably an integer of 1 or more.

The compound (1A) in the second embodiment is preferably the same as the compound (1) described in the section of "1. Compound".

Specific examples of the compound (1A) in the second embodiment are preferably the compounds listed as specific examples of the above-mentioned "1. Compound" (specific compounds), and the compound represented by the following formula (19), but are more preferably the compounds listed as specific examples of the above-mentioned "1. Compound".

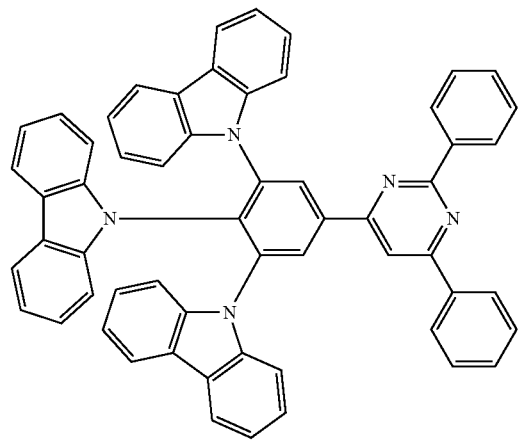

(19)

Regarding the difference 2, the organic EL device of the second embodiment contains the compound (1A) in the first layer therein. The compound (1A) may be contained in any other layer than the first layer, or may not be contained in any other layer, but preferably the compound (1A) is contained in only the first layer.

Preferably, the first layer is a layer neighboring to the light emitting layer.

Examples of the organic layer include a hole transporting zone (a hole injecting layer, a hole transporting layer, an electron blocking layer, an exciton blocking layer, etc.) provided between the anode and the light emitting layer, the light emitting layer, a space layer, an electron transporting zone (an electron injecting layer, an electron transporting layer, a hole blocking layer, etc.) provided between the cathode and the light emitting layer. In the organic EL device of the second embodiment, the compound (1A) is contained in the first layer between the light emitting layer and the cathode among the organic layers. The compound (1A) is preferably used as a material for the electron transporting zone in a fluorescent or phosphorescent EL device, more preferably as a material for the electron transporting layer or the hole blocking layer.

3-3. Organic EL Devices of First Embodiment and Second Embodiment

The organic EL devices of the first embodiment and the second embodiment of the present invention may be a fluorescent or phosphorescent light emission-type monochromatic light emitting device or a fluorescent/phosphorescent hybrid-type white light emitting device, and may be a simple type having a single light emitting unit or a tandem type having a plurality of light emitting units. Among these, the fluorescent light emission-type device is preferred. The "light emitting unit" referred to herein refers to a minimum unit that emits light by recombination of injected holes and electrons, which includes organic layers among which at least one layer is a light emitting layer.

For example, as a representative device configuration of the simple type organic EL device, the following device configuration may be exemplified.

(1) Anode/Light Emitting Unit/Cathode

Also, the light emitting unit may be a stacked-type having a plurality of phosphorescent light emitting layers or fluorescent light emitting layers. In this case, a space layer may be provided between the light emitting layers for the purpose of preventing excitons generated in the phosphorescent light emitting layer from diffusing into the fluorescent light emitting layer. Representative layer configurations of the simple type light emitting unit are described below. Layers in parentheses are optional.

(a) (hole injecting layer/) hole transporting layer/fluorescent light emitting layer (/electron transporting layer/electron injecting layer)

(b) (hole injecting layer/) hole transporting layer/phosphorescent light emitting layer (/electron transporting layer/electron injecting layer)

(c) (hole injecting layer/) hole transporting layer/first fluorescent light emitting layer/second fluorescent light emitting layer (/electron transporting layer/electron injecting layer)

(d) (hole injecting layer/) hole transporting layer/first phosphorescent light emitting layer/second phosphorescent light emitting layer (/electron transporting layer/electron injecting layer)

(e) (hole injecting layer/) hole transporting layer/phosphorescent light emitting layer/space layer/fluorescent light emitting layer (/electron transporting layer/electron injecting layer)

(f) (hole injecting layer/) hole transporting layer/first phosphorescent light emitting layer/second phosphorescent light emitting layer/space layer/fluorescent light emitting layer (/electron transporting layer/electron injecting layer)

(g) (hole injecting layer/) hole transporting layer/first phosphorescent light emitting layer/space layer/second phosphorescent light emitting layer/space layer/fluorescent light emitting layer (/electron transporting layer/electron injecting layer)

(h) (hole injecting layer/) hole transporting layer/phosphorescent light emitting layer/space layer/first fluorescent light emitting layer/second fluorescent light emitting layer (/electron transporting layer/electron injecting layer)

(i) (hole injecting layer/) hole transporting layer/electron blocking layer/fluorescent light emitting layer (/electron transporting layer/electron injecting layer)

(j) (hole injecting layer/) hole transporting layer/electron blocking layer/phosphorescent light emitting layer (/electron transporting layer/electron injecting layer)

(k) (hole injecting layer/) hole transporting layer/exciton blocking layer/fluorescent light emitting layer (/electron transporting layer/electron injecting layer)

(l) (hole injecting layer/) hole transporting layer/exciton blocking layer/phosphorescent light emitting layer (/electron transporting layer/electron injecting layer)

(m) (hole injecting layer/) first hole transporting layer/second hole transporting layer/fluorescent light emitting layer (/electron transporting layer/electron injecting layer)

(n) (hole injecting layer/) first hole transporting layer/second hole transporting layer/phosphorescent light emitting layer (/electron transporting layer/electron injecting layer)

(o) (hole injecting layer/) first hole transporting layer/second hole transporting layer/fluorescent light emitting layer/first electron transporting layer/second electron transporting layer (/electron injecting layer)

(p) (hole injecting layer/) first hole transporting layer/second hole transporting layer/phosphorescent light emitting layer/first electron transporting layer/second electron transporting layer (/electron injecting layer)

(q) (hole injecting layer/) hole transporting layer/fluorescent light emitting layer/hole blocking layer (/electron transporting layer/electron injecting layer)

(r) (hole injecting layer/) hole transporting layer/phosphorescent light emitting layer/hole blocking layer (/electron transporting layer/electron injecting layer)

(s) (hole injecting layer/) hole transporting layer/fluorescent light emitting layer/exciton blocking layer (/electron transporting layer/electron injecting layer)

(t) (hole injecting layer/) hole transporting layer/phosphorescent light emitting layer/exciton blocking layer (/electron transporting layer/electron injecting layer)

The phosphorescent and fluorescent light emitting layers may emit emission colors different from each other, respectively. Specifically, in the stacked light emitting unit (f), a layer configuration such as (hole injecting layer/) hole transporting layer/first phosphorescent light emitting layer (red light emission)/second phosphorescent light emitting layer (green light emission)/space layer/fluorescent light emitting layer (blue light emission)/electron transporting layer may be exemplified.

An electron blocking layer may be properly provided between each light emitting layer and the hole transporting layer or the space layer. Also, a hole blocking layer may be properly provided between each light emitting layer and the electron transporting layer. The employment of the electron blocking layer or the hole blocking layer allows to improve the emission efficiency by trapping electrons or holes within the light emitting layer and increasing the probability of charge recombination in the light emitting layer.

As a representative device configuration of the tandem type organic EL device, the following device configuration may be exemplified.

(2) Anode/First Light Emitting Unit/Intermediate Layer/Second Light Emitting Unit/Cathode Here, for example, each of the first light emitting unit and second light emitting unit may be independently selected from the above-described light emitting units.

The intermediate layer is also generally referred to as an intermediate electrode, an intermediate conductive layer, a charge generation layer, an electron withdrawing layer, a connecting layer, or an intermediate insulating layer, and a known material configuration may be used, in which electrons are supplied to the first light emitting unit, and holes are supplied to the second light emitting unit.

FIG. 1 is a schematic view illustrating an example of a configuration of the organic EL device of the embodiments of the present invention. The organic EL device 1 of this example includes a substrate 2, an anode 3, a cathode 4, and a light emitting unit 10 disposed between the anode 3 and the cathode 4. The light emitting unit 10 includes a light emitting layer 5. A hole transporting zone 6 (a hole injecting layer, a hole transporting layer, etc.) is provided between the light emitting layer 5 and the anode 3, and an electron transporting zone 7 (an electron injecting layer, an electron transporting layer, etc.) is provided between the light emitting layer 5 and the cathode 4.

FIG. 2 is a schematic view illustrating another configuration of the embodiments of the organic EL device of the present invention. An organic EL device 11 of this example includes the substrate 2, the anode 3, the cathode 4, and a light emitting unit 20 disposed between the anode 3 and the cathode 4. The light emitting unit 20 includes the light emitting layer 5. A hole transporting zone 6 is disposed between the light emitting layer 5 and the anode 3, and an electron transporting zone 7 is disposed between the light emitting layer 5 and the cathode 4. A hole blocking layer 8 is disposed neighboring to the light emitting layer 5 on the side of the cathode 4 of the light emitting layer 5. Accordingly, holes are trapped in the light emitting layer 5 to thereby more increase the production efficiency of excitons in the light emitting layer 5. The hole blocking layer 8 can also be considered to be a part of the electron transporting zone 7. An electron blocking layer (not shown) can be provided on the side of the anode 3 of the light emitting layer 5 to thereby trap electrons in the light emitting layer 5 to further increase the production efficiency of excitons in the light emitting layer 5.

FIG. 3 is a schematic view illustrating still another configuration of the embodiments of the organic EL device of the present invention. An organic EL device 12 includes the substrate 2, the anode 3, the cathode 4, and a light emitting unit 30 disposed between the anode 3 and the cathode 4. The light emitting unit 20 includes the light emitting layer 5. A hole transporting zone disposed between the anode 3 and the light emitting layer 5 is formed of a first hole transporting layer 6a and a second hole transporting layer 6b. Also, an electron transporting zone disposed between the light emitting layer 5 and the cathode 4 is formed of a first electron transporting layer 7a and a second electron transporting layer 7b. The organic EL device 12 may have a combination of a single layer of an electron transporting layer and plural layers of hole transporting layers, or a combination of a single layer of a hole transporting layer and plural layers of electron transporting layers. A hole blocking layer and an electron blocking layer may be provided in the organic EL device 12.

In the present specification, a host combined with a fluorescent dopant (a fluorescent emitting material) is called a fluorescent host, and a host combined with a phosphorescent dopant is called a phosphorescent host. The fluorescent host and the phosphorescent host are not distinguished from each other merely by their molecular structures. That is, the phosphorescent host means a material that forms a phosphorescent light emitting layer containing a phosphorescent dopant, but does not mean unavailability as a material that forms a fluorescent light emitting layer. The same also applies to the fluorescent host.

The layers and the members constituting the organic EL device are described below.

Substrate

The substrate is used as a support of the organic EL device. Examples of the substrate include a plate of glass, quartz, and plastic. Also, a flexible substrate may be used. Examples of the flexible substrate include a plastic substrate made of polycarbonate, polyarylate, polyether sulfone, polypropylene, polyester, polyvinyl fluoride, or polyvinyl chloride. Also, an inorganic vapor deposition film may be used.

Anode

It is preferable that a metal, an alloy, an electrically conductive compound, or a mixture thereof which has a high work function (specifically 4.0 eV or more) is used for the anode formed on the substrate. Specific examples thereof include indium oxide-tin oxide (ITO: Indium Tin Oxide), indium oxide-tin oxide containing silicon or silicon oxide, indium oxide-zinc oxide, indium oxide containing tungsten oxide and zinc oxide, and graphene. Besides, gold (Au), platinum (Pt), nickel (Ni), tungsten (W), chromium (Cr), molybdenum (Mo), iron (Fe), cobalt (Co), copper (Cu), palladium (Pd), titanium (Ti), or nitrides of the metals (for example, titanium nitride) may be exemplified.

These materials are usually deposited by a sputtering method. For example, through a sputtering method, it is possible to form indium oxide-zinc oxide by using a target in which 1 to 10 wt % of zinc oxide is added to indium oxide, and to form indium oxide containing tungsten oxide and zinc oxide by using a target containing 0.5 to 5 wt % of tungsten oxide and 0.1 to 1 wt % of zinc oxide with respect to indium oxide. Besides, the manufacturing may be performed by a vacuum vapor deposition method, a coating method, an inkjet method, a spin coating method, etc.

The hole injecting layer formed in contact with the anode is formed by using a material that facilitates hole injection regardless of a work function of the anode, and thus, it is possible to use materials generally used as an electrode material (for example, metals, alloys, electrically conductive compounds, or mixtures thereof, elements belonging to Group 1 or 2 of the periodic table of the elements).

It is also possible to use elements belonging to Group 1 or 2 of the periodic table of the elements, which are materials having low work functions, that is, alkali metals such as lithium (Li) and cesium (Cs), alkaline earth metals such as magnesium (Mg), calcium (Ca), and strontium (Sr), and alloys containing these (for example, MgAg, AlLi), and rare earth metals such as europium (Eu), and ytterbium (Yb) and alloys containing these. When the anode is formed by using the alkali metals, the alkaline earth metals, and alloys containing these, a vacuum vapor deposition method or a sputtering method may be used. Further, when a silver paste or the like is used, a coating method, an inkjet method, etc. may be used.

Hole Injecting Layer

The hole injecting layer is a layer containing a material having a high hole injection ability (a hole injecting material). The hole injecting materials may be used alone or in combination in the hole injecting layer.

Examples of the hole injecting material include molybdenum oxide, titanium oxide, vanadium oxide, rhenium oxide, ruthenium oxide, chromium oxide, zirconium oxide, hafnium oxide, tantalum oxide, silver oxide, tungsten oxide, and manganese oxide.

Examples of the hole injecting layer material also include aromatic amine compounds as low molecular organic compounds, such as 4,4',4"-tris(N,N-diphenylamino)triphenylamine (abbreviation: TDATA), 4,4', 4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1).

High molecular compounds (oligomers, dendrimers, polymers, etc.) may also be used. Examples thereof include high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), and poly[N,N'-bis(4-butylphenyl)-N,N'-bis(phenyl)benzidine] (abbreviation: Poly-TPD). In addition, high molecular compounds to which an acid is added, such as poly(3,4-ethylenedioxythiophene)/poly (styrene sulfonic acid) (PEDOT/PSS), and polyaniline/poly (styrenesulfonic acid) (PAni/PSS), may also be used.

Also, it is also preferable to use an acceptor material such as a hexaazatriphenylene (HAT) compound represented by formula (K), in combination with another compound.

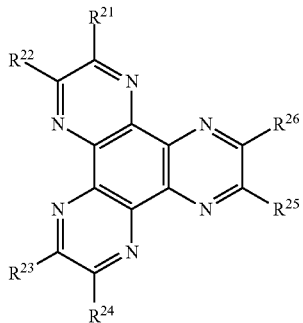

(K)

In formula (K), each of $R^{21}$ to $R^{26}$ independently represents a cyano group, —$CONH_2$, a carboxy group, or —$COOR^{27}$ ($R^{27}$ represents an alkyl group having 1 to 20 carbon atoms or a cycloalkyl group having 3 to 20 carbon atoms). Also, adjacent two selected from $R^{21}$ and $R^{22}$, $R^{23}$ and $R^{24}$, and $R^{25}$ and $R^{26}$ may be bonded to each other to form a group represented by —CO—O—CO—.

Examples of $R^{27}$ include a methyl group, an ethyl group, an n-propyl group, an isopropyl group, an n-butyl group, an isobutyl group, a t-butyl group, a cyclopentyl group, and a cyclohexyl group.

Hole Transporting Layer

The hole transporting layer is a layer containing a material having a high hole transporting ability (a hole transporting material). The hole transporting materials may be used alone or in combination. Examples of the hole transporting material include an aromatic amine compound, a carbazole derivative, and an anthracene derivative.

Examples of the aromatic amine compound include 4,4'-bis[N-(1-naphthyl)-N-phenylamino]biphenyl (abbreviation: NPB) or N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluorene-2-yl)-N-phenylamino]biphenyl (abbreviation: DFLDPBi), 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). These aromatic amine compounds have a hole mobility of $10^{-6}$ cm$^2$/Vs or more.

Examples of the carbazole derivative include 4,4'-di(9-carbazolyl)biphenyl (abbreviation: CBP), 9-[4-(9-carbazolyl)phenyl]-10-phenylanthracene (abbreviation: CzPA), and 9-phenyl-3-[4-(10-phenyl-9-anthryl)phenyl]-9H-carbazole (abbreviation: PCzPA). Examples of the anthracene derivative include 2-t-butyl-9,10-di(2-naphthyl)anthracene (abbreviation: t-BuDNA), 9,10-di(2-naphthyl)anthracene (abbreviation: DNA), and 9,10-diphenylanthracene (abbreviation: DPAnth).

Examples thereof also include high molecular compounds such as poly(N-vinylcarbazole) (abbreviation: PVK) or poly (4-vinyltriphenylamine) (abbreviation: PVTPA).

Meanwhile, compounds other than the above may also be used as long as they are compounds high in the hole transporting ability rather than in the electron transporting ability.

The hole transporting layer may have a single-layer structure, or a multi-layer structure including two or more layers. For example, the hole transporting layer may have a two-layer structure including a first hole transporting layer (anode side) and a second hole transporting layer (cathode side).

Dopant Material of Light Emitting Layer

The light emitting layer is a layer containing a material having a high light emitting property (a dopant material), and various materials may be used. For example, a fluorescent emitting material or a phosphorescent emitting material may be used as the dopant material. The fluorescent emitting material is a compound that emits light from a singlet excited state, and the phosphorescent emitting material is a compound that emits from a light triplet excited state.

Examples of a blue-based fluorescent emitting material that may be used for the light emitting layer include a pyrene derivative, a styrylamine derivative, a chrysene derivative, a fluoranthene derivative, a fluorene derivative, a diamine derivative, and a triarylamine derivative. Specific examples thereof include N,N'-bis[4-(9H-carbazole-9-yl)phenyl]-N, N'-diphenylstilbene-4,4'-diamine (abbreviation: YGA2S), 4-(9H-carbazole-9-yl)-4'-(10-phenyl-9-anthryl)triphenylamine (abbreviation: YGAPA), and 4-(10-phenyl-9-anthryl)-4'-(9-phenyl-9H-carbazole-3-yl)triphenylamine (abbreviation: PCBAPA).

Examples of a green-based fluorescent emitting material that may be used for the light emitting layer include an aromatic amine derivative. Specific examples thereof include N-(9,10-diphenyl-2-anthryl)-N,9-diphenyl-9H-carbazole-3-amine (abbreviation: 2PCAPA), N-[9,10-bis(1,1'-biphenyl-2-yl)-2-anthryl]-N,9-diphenyl-9H-carbazole-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), N-[9,10-bis(1,1'-biphenyl-2-yl)]-N-[4-(9H-carbazole-9-yl)phenyl]-N-phenylanthrac ene-2-amine (abbreviation: 2YGABPhA), and N,N,9-triphenylanthracene-9-amine (abbreviation: DPhAPhA).

Examples of a red-based fluorescent emitting material that may be used for the light emitting layer include a tetracene derivative and a diamine derivative. Specific examples thereof include N,N,N',N'-tetrakis(4-methylphenyl)tetracene-5,11-diamine (abbreviation: p-mPhTD) and 7,14-diphenyl-N,N,N',N'-tetrakis(4-methylphenyl)acenaphtho[1,2-a]fluoranthene-3,10-diamine (abbreviation: p-mPhAFD).

Examples of a blue-based phosphorescent emitting material that may be used for the light emitting layer include a metal complex such as an iridium complex, an osmium complex, and a platinum complex. Specific examples thereof include bis[2-(4',6'-difluorophenyl)pyridinato-N,C2']iridium(III)tetrakis(1-pyrazolyl)borate (abbreviation: FIr6), bis[2-(4',6'-difluorophenyl)pyridinato-N,C2']iridium(III)picolinate (abbreviation: FIrpic), bis[2-(3',5'bistrifluoromethylphenyl)pyridinato-N,C2']iridium(III)picolinate (abbreviation: Ir(CF3ppy)2(pic)), and bis[2-(4',6'-difluorophenyl)pyridinato-N,C2']iridium(III)acetylacetonate (abbreviation: FIracac).

Examples of a green-based phosphorescent emitting material that may be used for the light emitting layer include an iridium complex. Examples thereof include tris(2-phenylpyridinato-N,C2')iridium(III) (abbreviation: Ir(ppy)3), bis(2-phenylpyridinato-N,C2')iridium(III)acetylacetonate (abbreviation: Ir(ppy)2(acac)), bis(1,2-diphenyl-1H-benzimidazolato)iridium(III)acetylacetonate (abbreviation: Ir(pbi)2(acac)), and bis(benzo[h]quinolinato)iridium(III)acetylacetonate (abbreviation: Ir(bzq)2(acac)).

Examples of a red-based phosphorescent emitting material that may be used for the light emitting layer include a metal complex such as an iridium complex, a platinum complex, a terbium complex, and a europium complex. Specific examples thereof include organic metal complexes such as bis[2-(2'-benzo[4,5-a]thienyl)pyridinato-N,C3']iridium(III)acetylacetonate (abbreviation: Ir(btp)2(acac)), bis(1-phenylisoquinolinato-N,C2')iridium(III)acetylacetonate (abbreviation: Ir(piq)2(acac)), (acetylacetonate)bis[2,3-bis(4-fluorophenyl)quinoxalinato]iridium(III) (abbreviation: Ir(Fdpq)2(acac)), and 2,3,7,8,12,13,17,18-octaethyl-21H,23H-porphyrinplatinum(II) (abbreviation: PtOEP).

Also, rare earth metal complexes such as tris(acetylacetonate) (monophenanthroline)terbium(III) (abbreviation: Tb(acac)3(Phen)), tris(1,3-diphenyl-1,3-propandionato) (monophenanthroline)europium(III) (abbreviation: Eu(DBM)3(Phen)), and tris[1-(2-thenoyl)-3,3,3-trifluoroacetonate](monophenanthroline)europium(III) (abbreviation: Eu(TTA)3(Phen)) emit light from rare earth metal ions (electron transition between different multiplicities), and thus may be used as the phosphorescent emitting material.

Host Material of Light Emitting Layer

The light emitting layer may have a configuration in which the above-described dopant material is dispersed in another material (a host material). The host material is preferably a material that has a higher lowest unoccupied orbital level (LUMO level) and a lower highest occupied orbital level (HOMO level) than the dopant material.

Examples of the host material include:
(1) a metal complex such as an aluminum complex, a beryllium complex, or a zinc complex,
(2) a heterocyclic compound such as an oxadiazole derivative, a benzimidazole derivative, or a phenanthroline derivative,
(3) a fused aromatic compound such as a carbazole derivative, an anthracene derivative, a phenanthrene derivative, a pyrene derivative, or a chrysene derivative, or
(4) an aromatic amine compound such as a triarylamine derivative or a fused polycyclic aromatic amine derivative.

For example, metal complexes such as tris(8-quinolinolato)aluminum(III) (abbreviation: Alq), tris(4-methyl-8-quinolinolato)aluminum(III) (abbreviation: Almq3), bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-biphenylyl)-4-phenyl-5-(4-tert-butylphenyl)-1,2,4-triazole (abbreviation: TAZ), 2,2',2"-(1,3,5-benzenetriyl)tris(1-phenyl-1H-benzimidazole) (abbreviation: TPBI), and bathophenanthroline (abbreviation: BPhen), bathocuproine (abbreviation: BCP); fused aromatic compounds such as 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl(abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3"-(benzene-1,3,5-triyl)tripyrene (abbreviation: TPB3), 9,10-diphenylanthracene (abbreviation: DPAnth), and 6,12-dimethoxy-5,11-diphenylchrysene; and aromatic amine compounds such as N,N-diphenyl-9-[4-(10-phenyl-9-anthryl)phenyl]-9H-carbazole-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazole-3-amine (abbreviation: PCAPA), N,9-diphenyl-N-{4-[4-(10-phenyl-9-anthryl)phenyl]phenyl}-9H-carbazole-3-amine (abbreviation: PCAPBA), N-(9,10-diphenyl-2-anthryl)-N,9-diphenyl-9H-carbazole-3-amine (abbreviation: 2PCAPA), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(9,9-dimethylfluoren-2-yl)-N-phenylamino]biphenyl (abbreviation: DFLDPBi), and 4,4'-bis[N-(spiro-9,9'-bifluorene-2-yl)-N-phenylamino]biphenyl (abbreviation: BSPB) may be used. A plurality of types of host materials may be used.

In particular, in the case of a blue fluorescent device, it is preferable to use the following anthracene compounds as the host material.

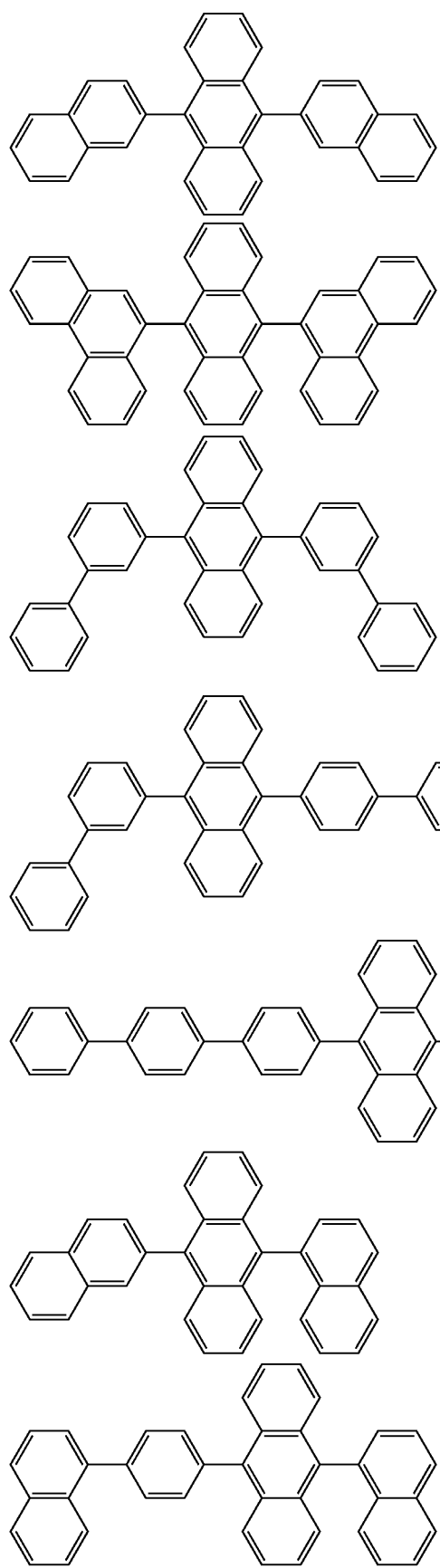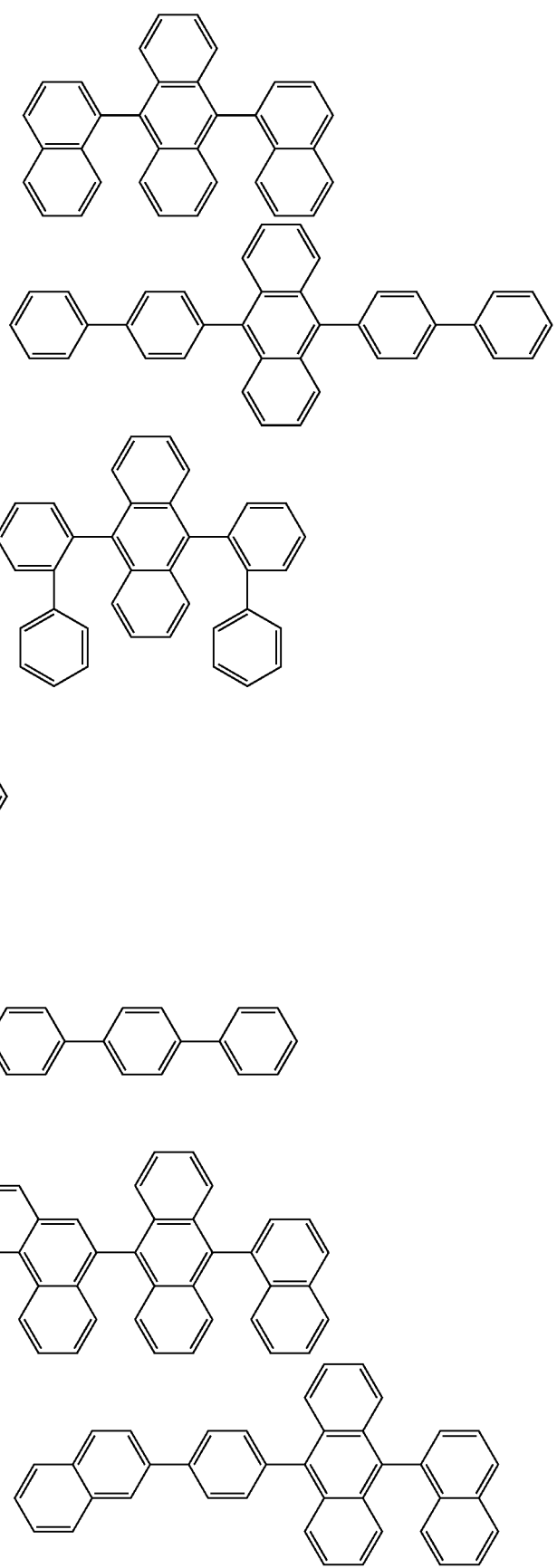

-continued
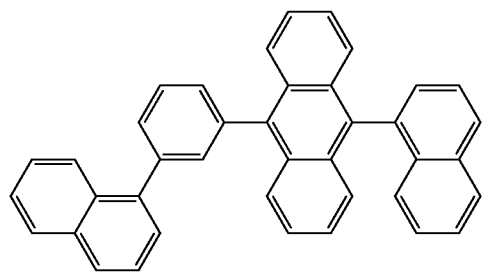
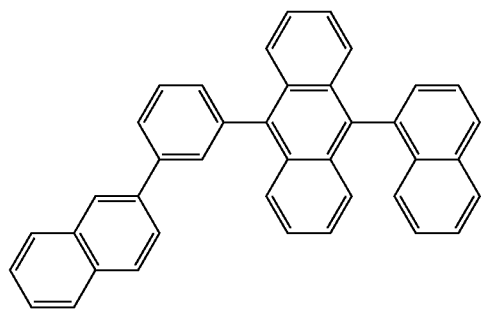
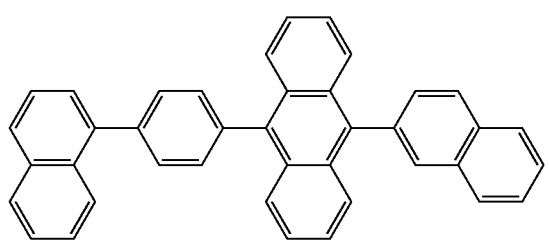
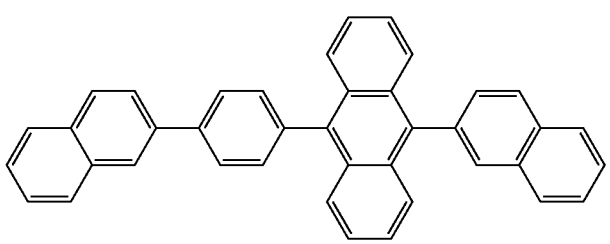
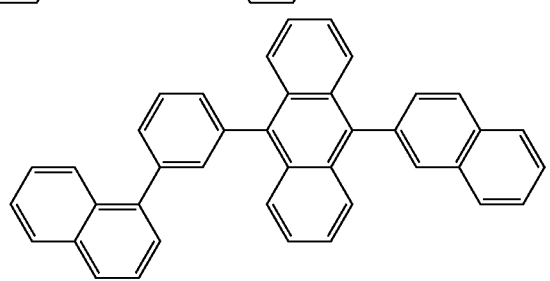
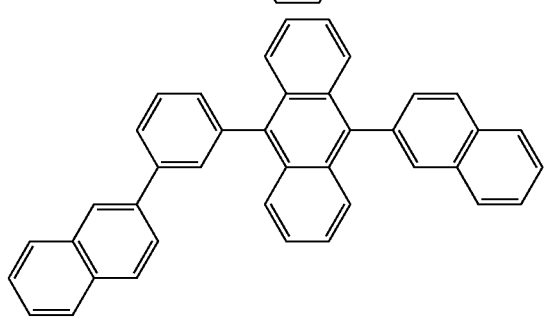
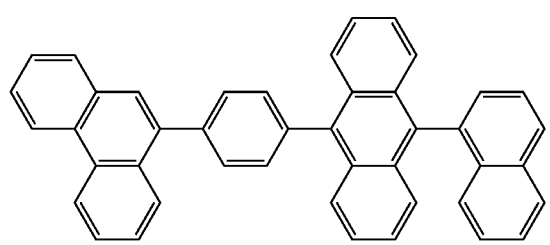
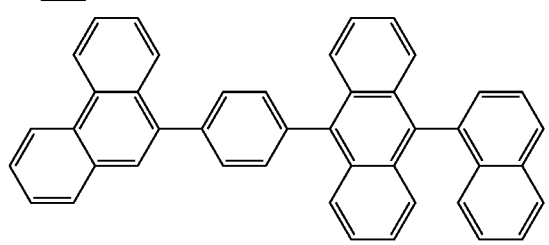
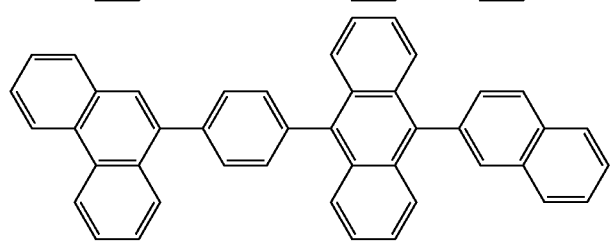
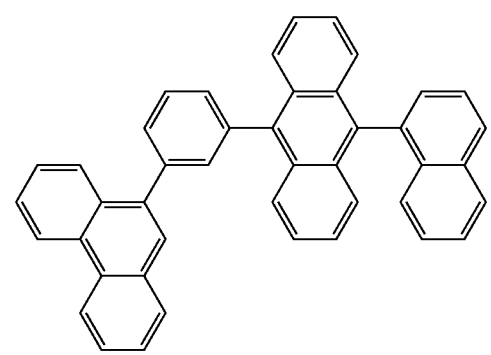

-continued
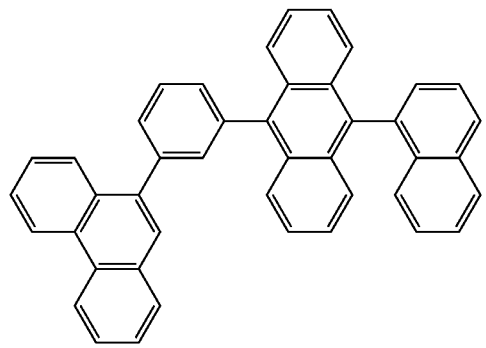
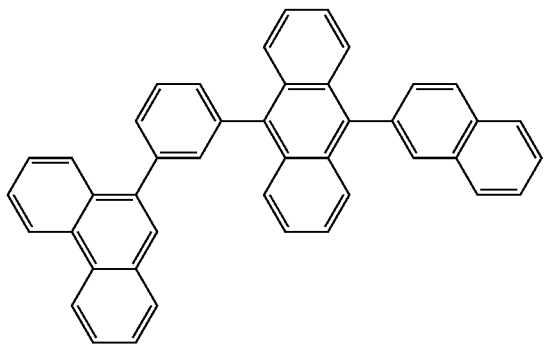
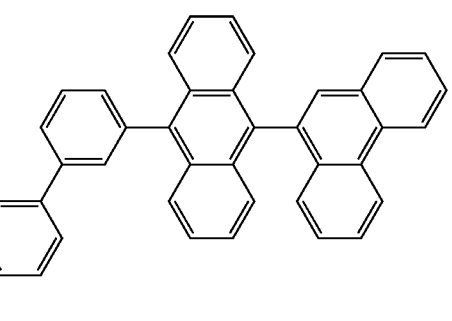
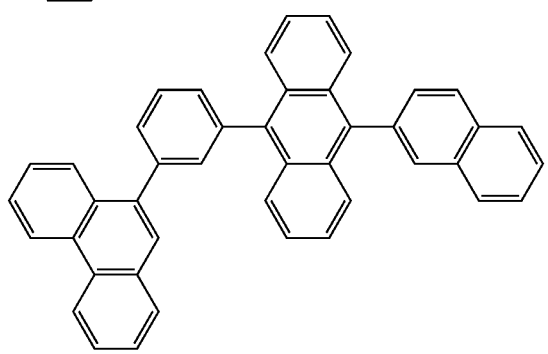
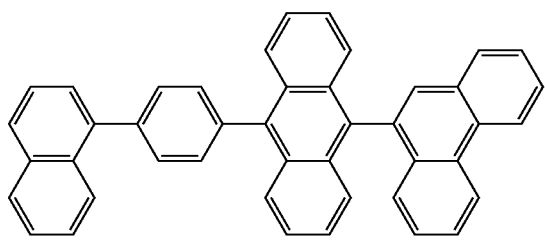
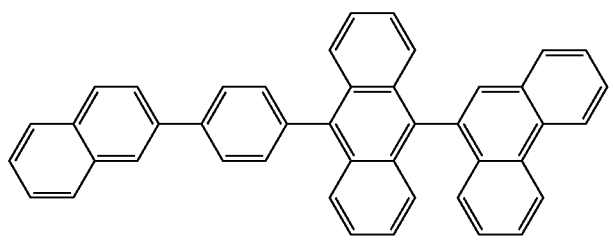
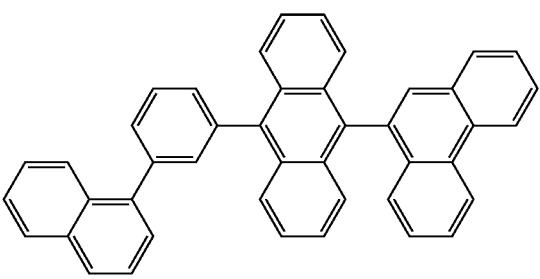
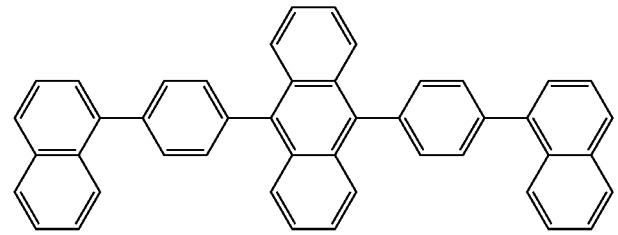
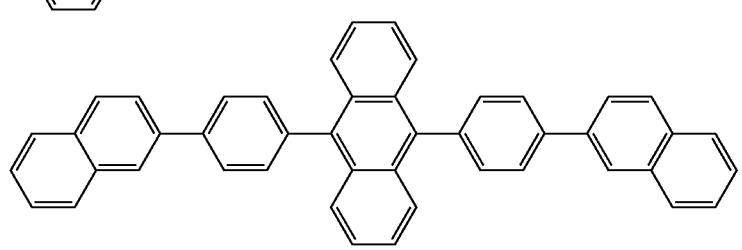
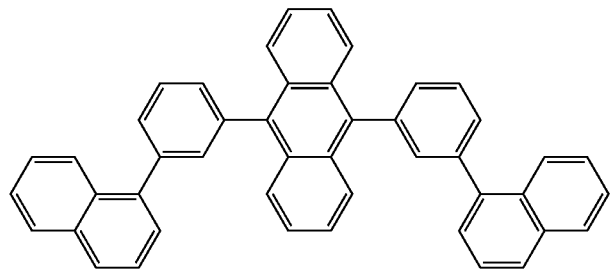

-continued
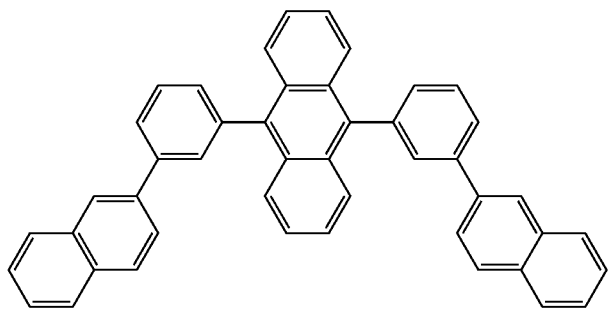
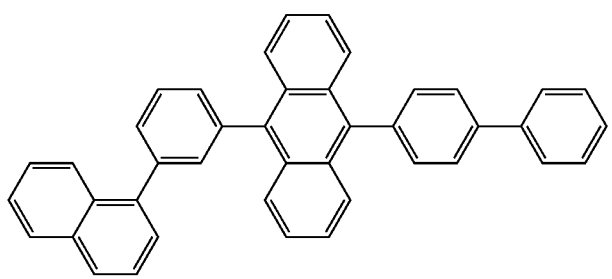
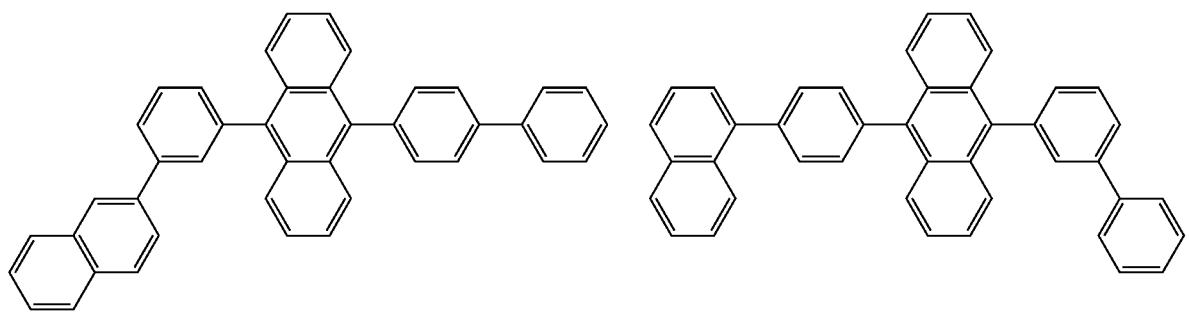
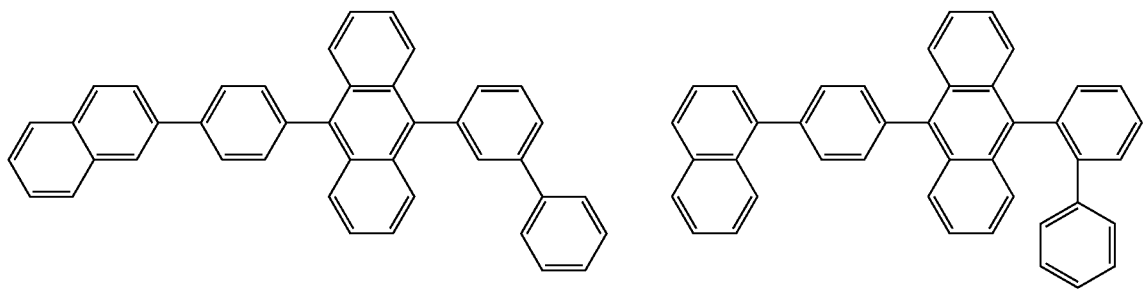
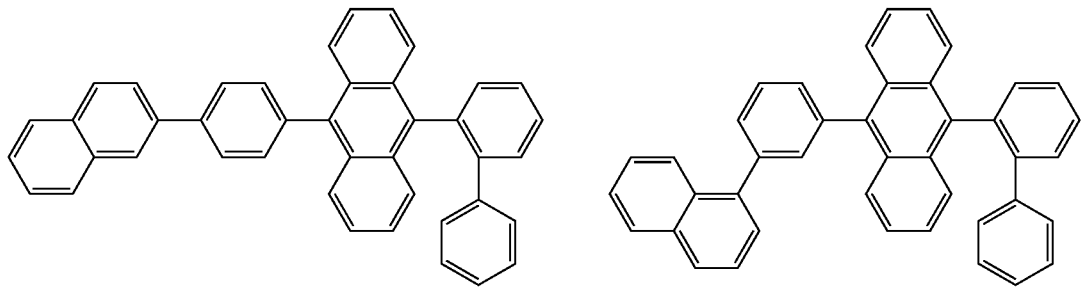

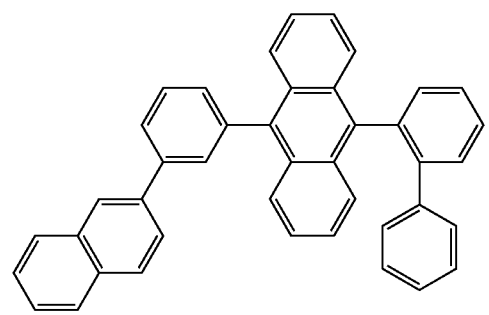

-continued
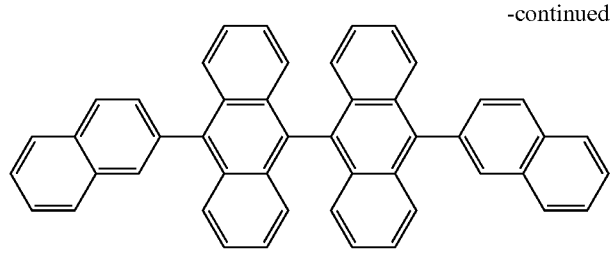
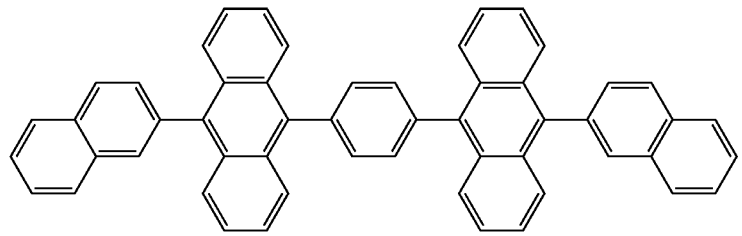
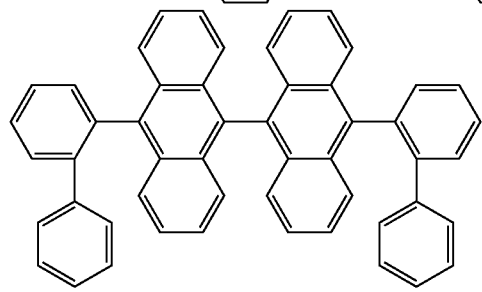
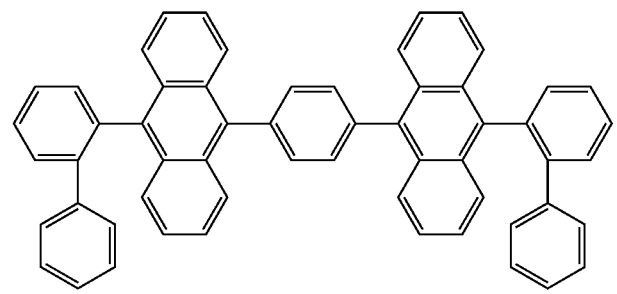
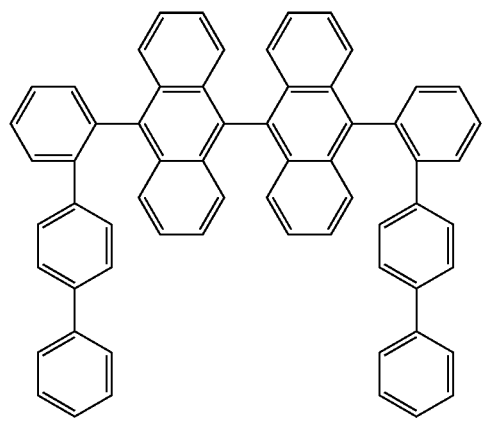
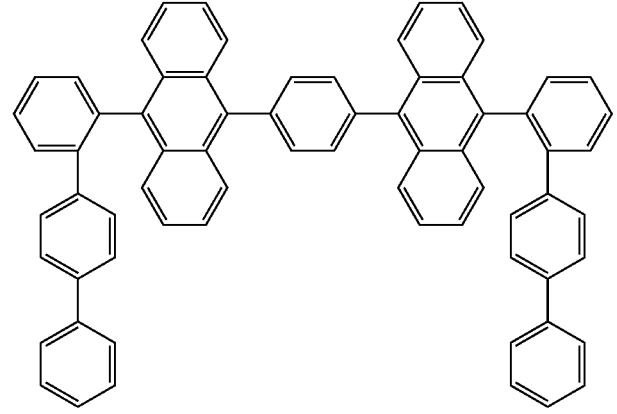
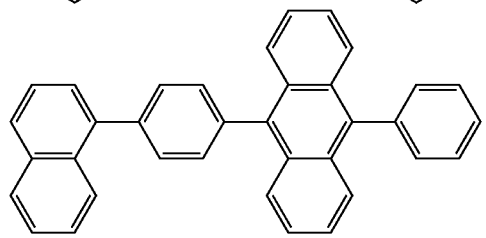
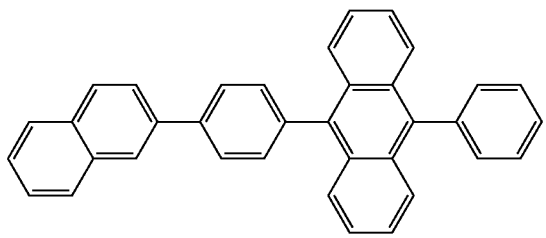
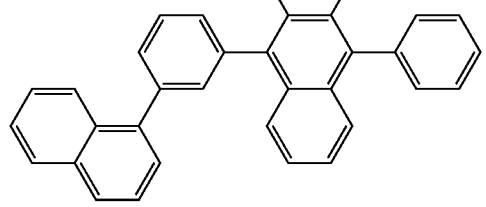
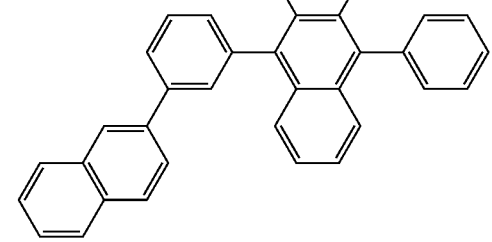

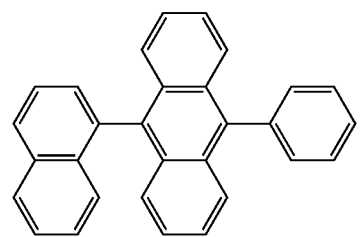 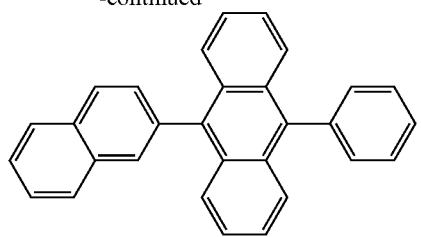
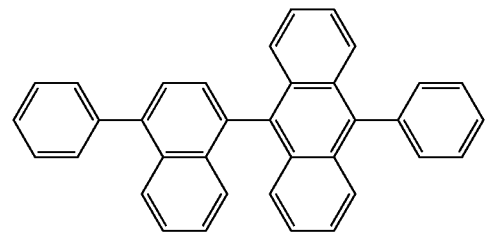 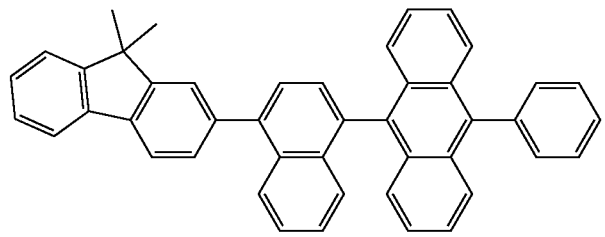
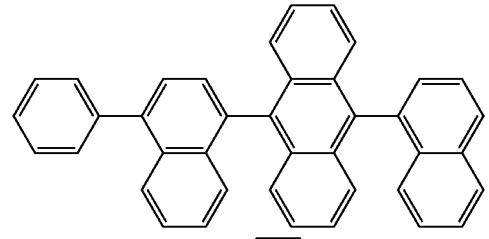 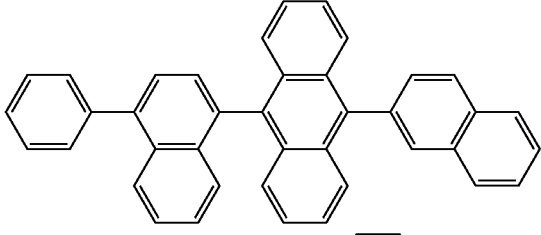
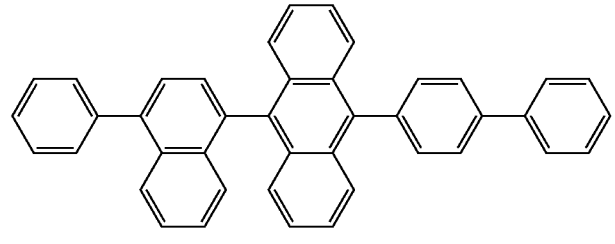 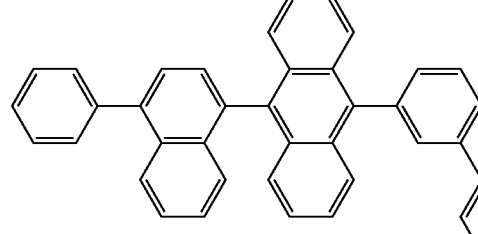
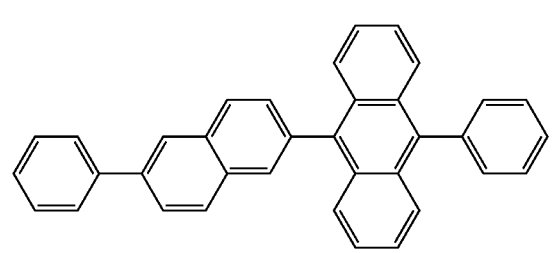 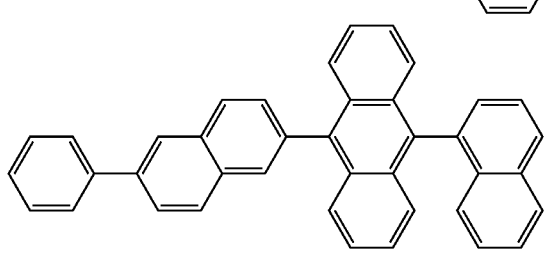
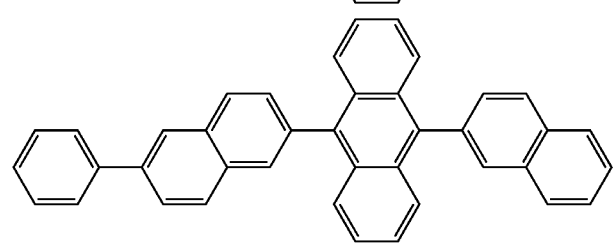 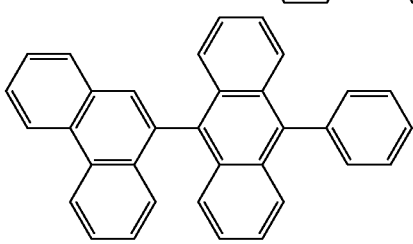
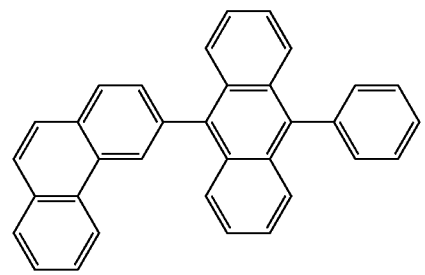 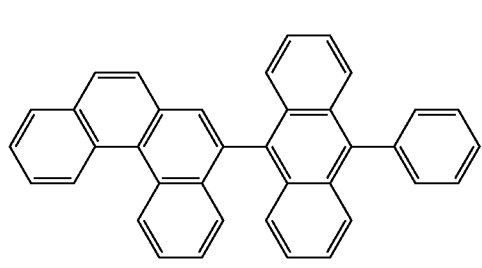

-continued
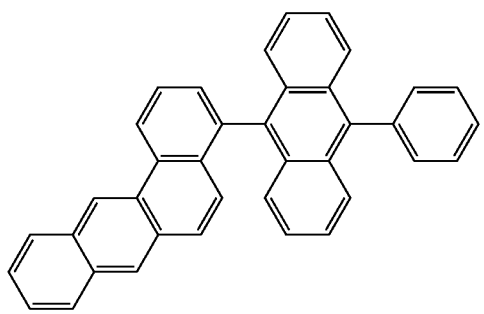
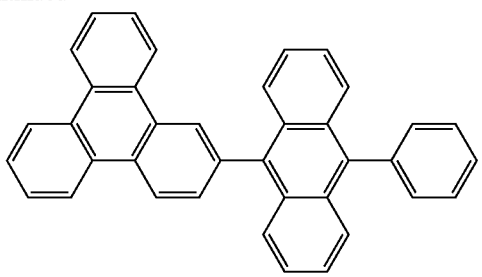
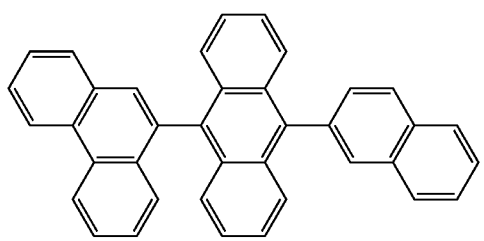
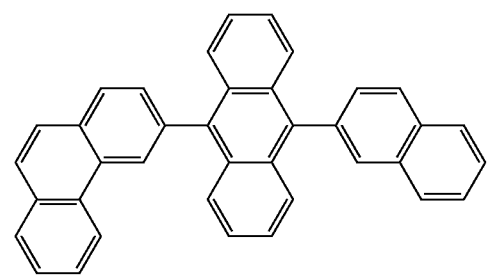
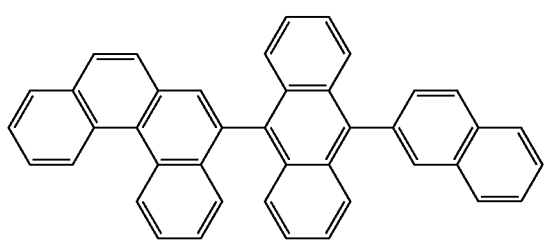
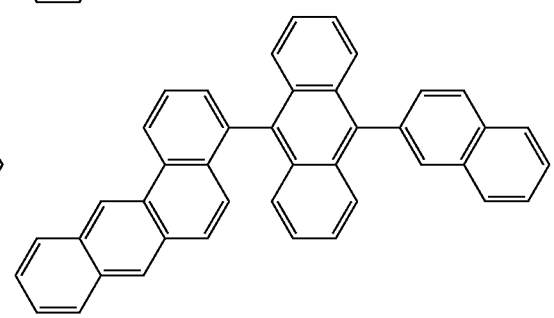
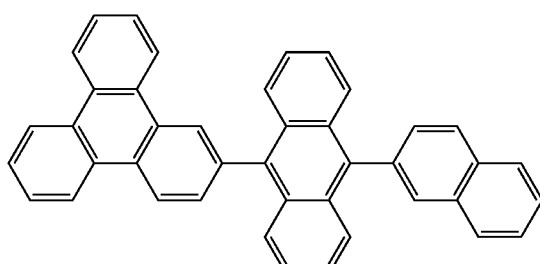
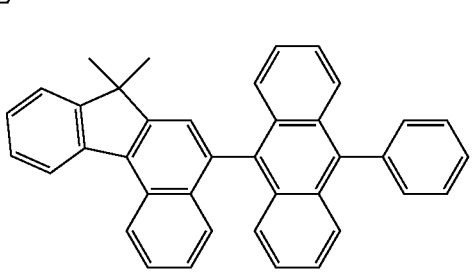
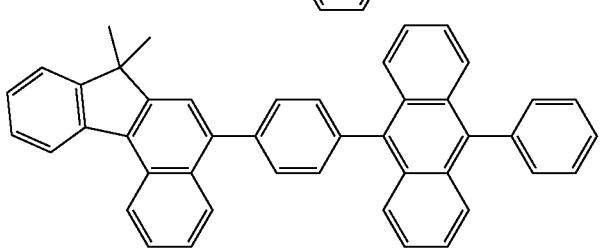
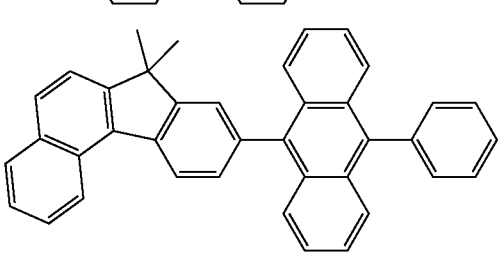
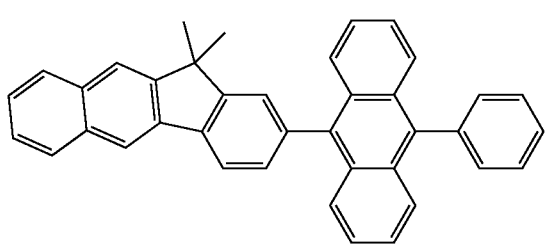
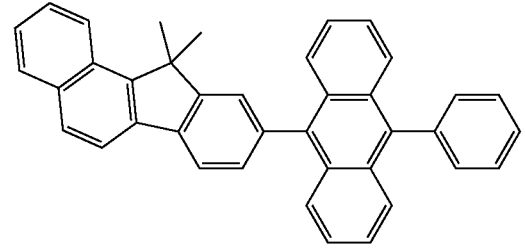

83
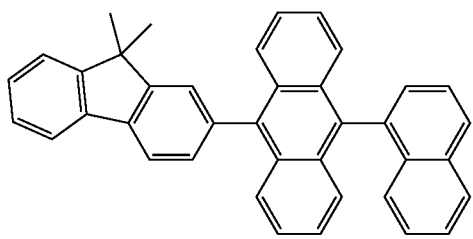
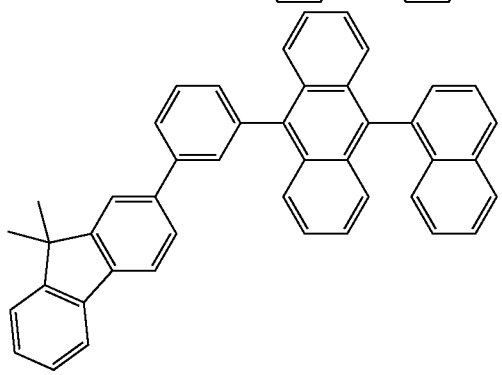
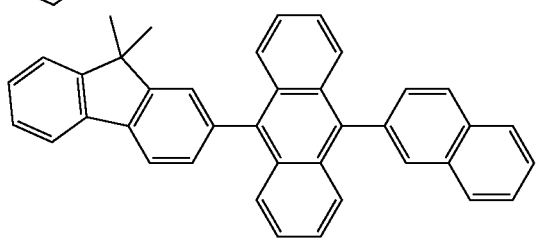
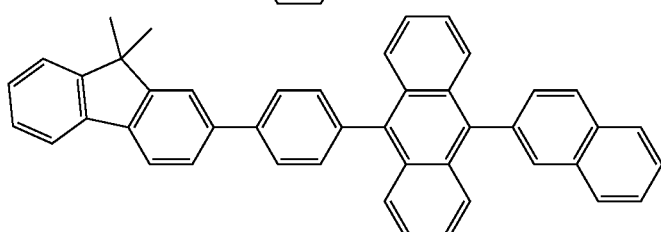
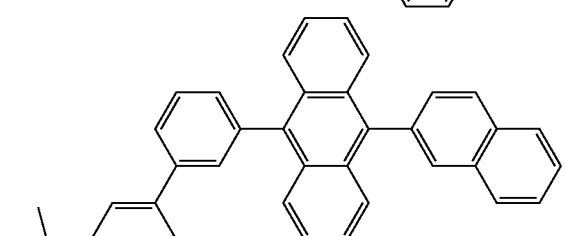
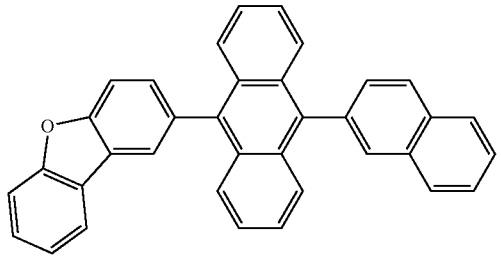
84
-continued
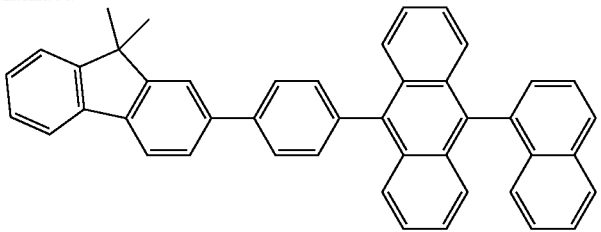
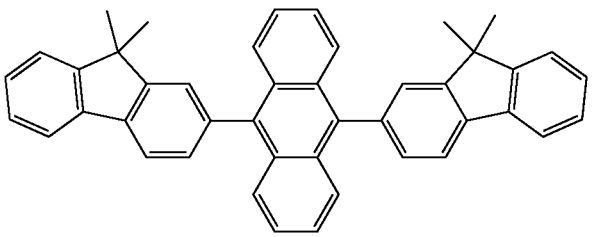
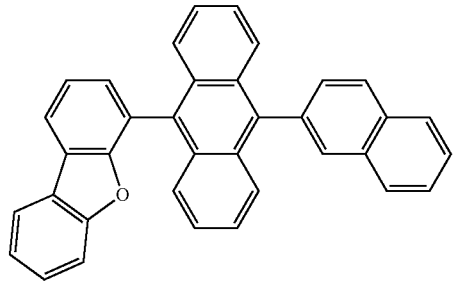

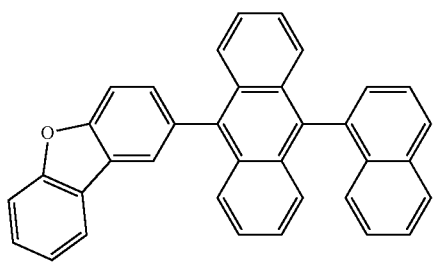
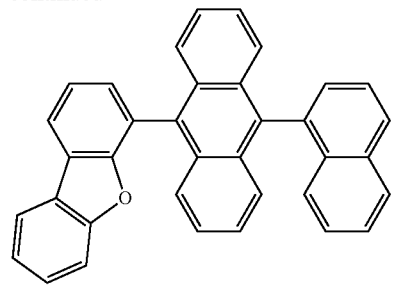
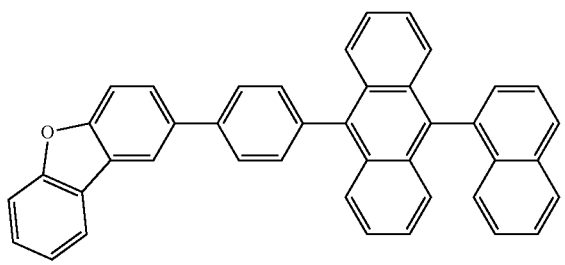
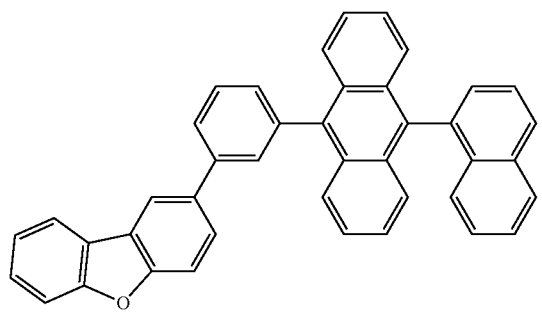
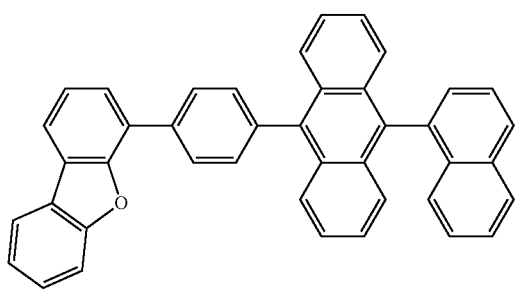
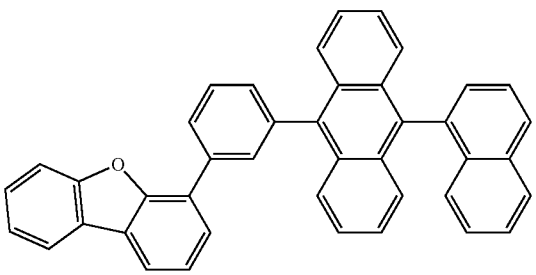
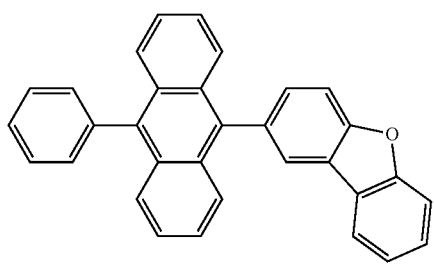
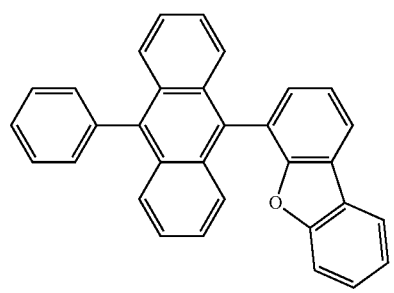
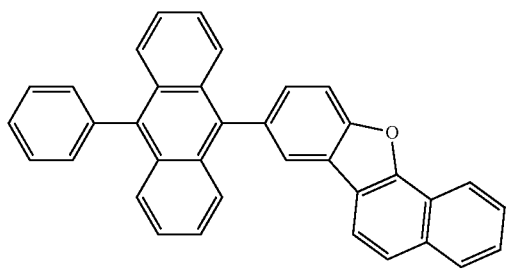
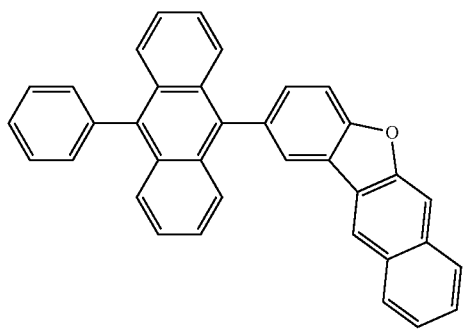

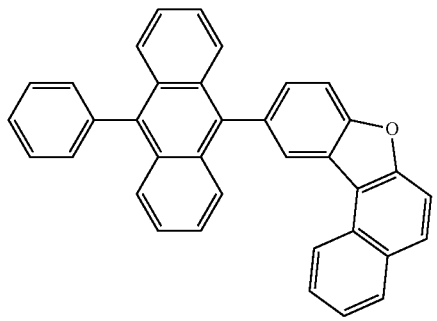
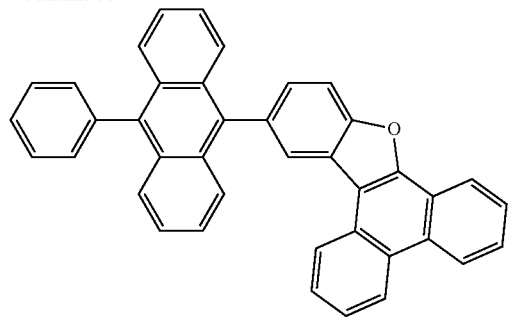
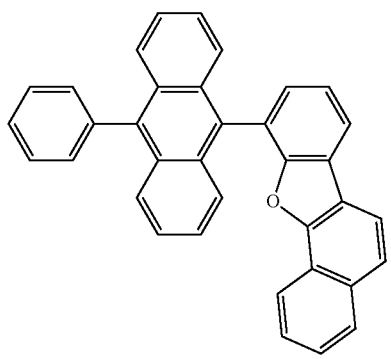
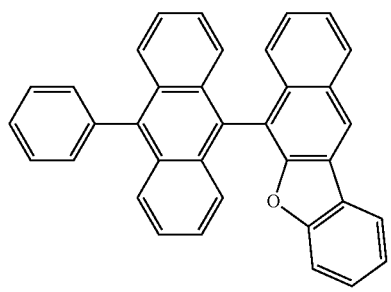
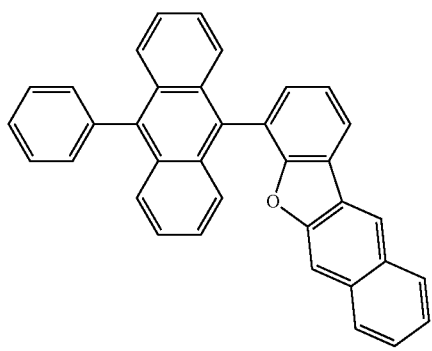
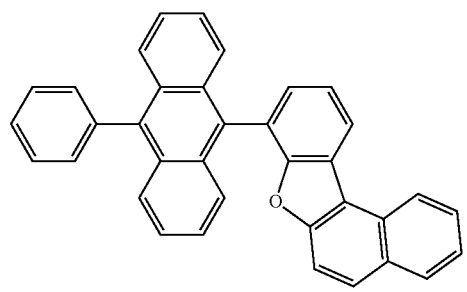
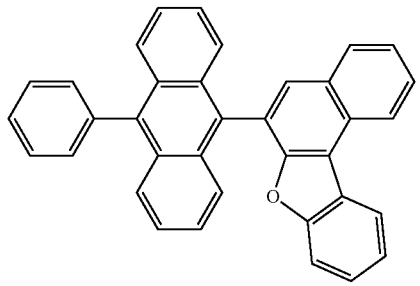
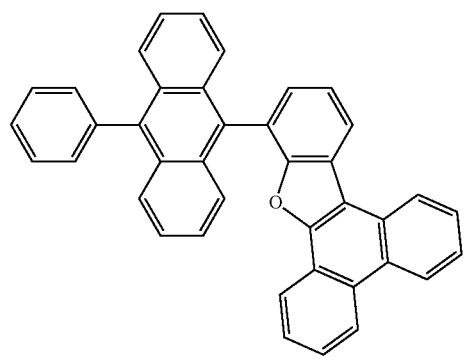
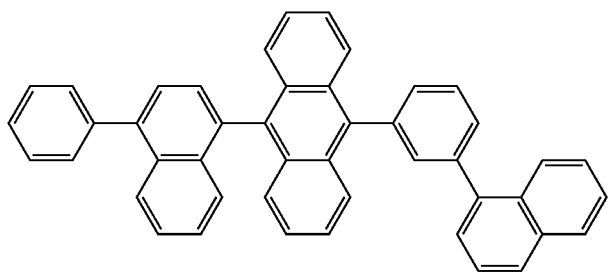

-continued
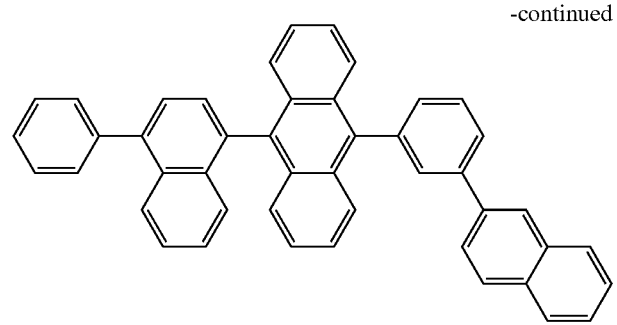
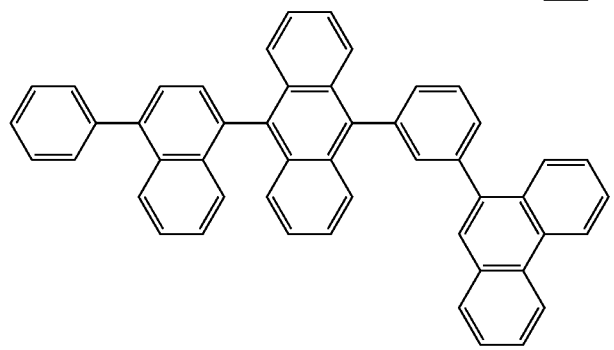
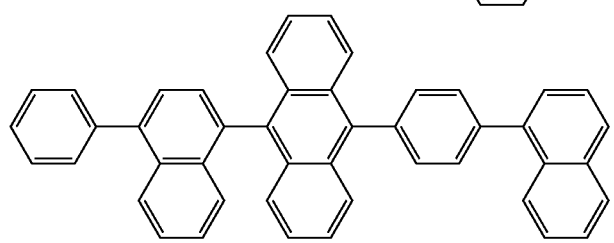
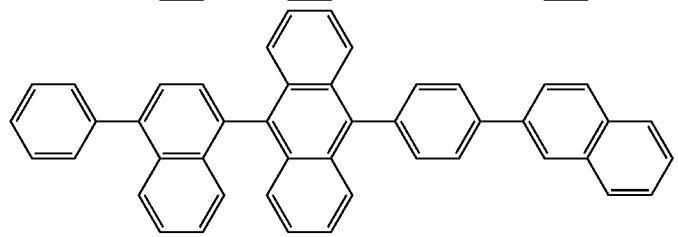
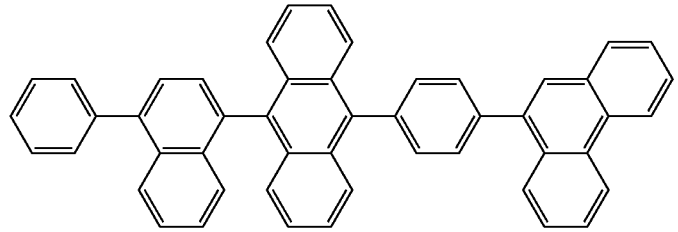
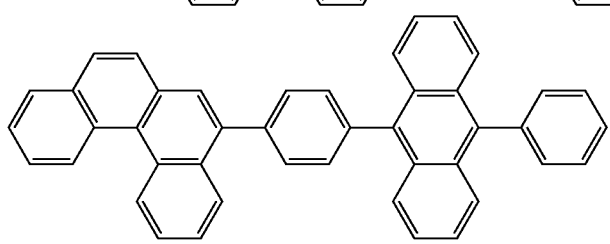
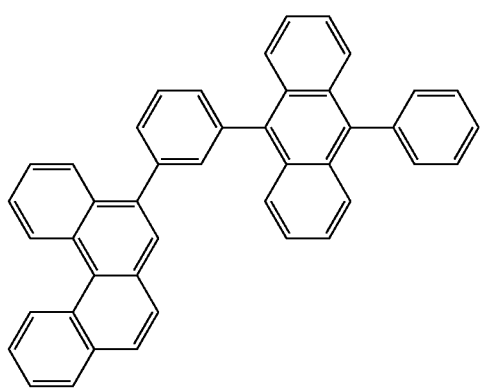

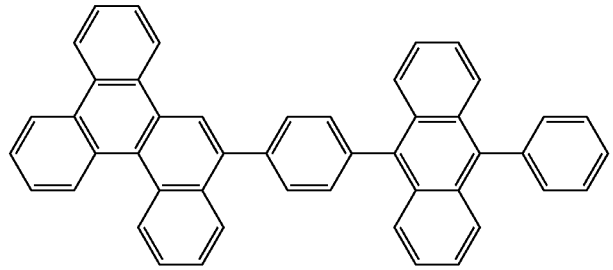
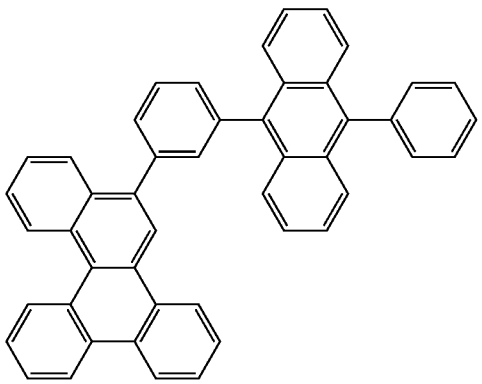
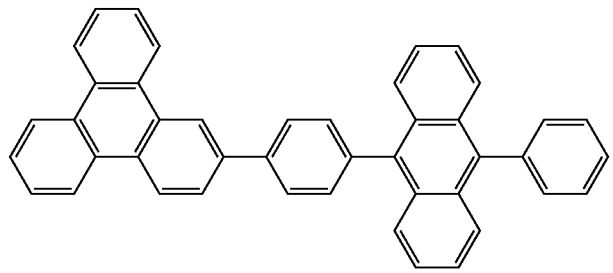
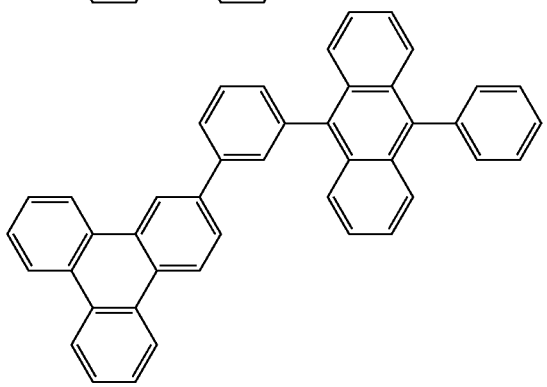

The electron transporting zone is constituted by the electron injecting layer, the electron transporting layer, the hole blocking layer, etc. It is preferable that any one of these layers contains the compound (1), and it is more preferable that at least one of the electron transporting layer and the hole blocking layer contains the compound (1). Also, any one of the layers in the electron transporting zone, particularly, the electron transporting layer preferably contains one or more selected from the group of an alkali metal, an alkaline earth metal, a rare earth metal, oxide of the alkali metal, an alkali metal halide, oxide of the alkaline earth metal, an alkaline earth metal halide, oxide of the rare earth metal, a rare earth metal halide, an organic complex containing the alkali metal, an organic complex containing the alkaline earth metal, and an organic complex containing the rare earth metal.

Electron Transporting Layer

The electron transporting layer is a layer containing a material having a high electron transporting ability (an electron transporting material). For the electron transporting layer, the compound (1) or a combination of the compound (1) with another electron transporting material may be used. Examples of another electron transporting material include:
(1) a metal complex such as an aluminum complex, a beryllium complex, or a zinc complex,
(2) a heteroaromatic compound such as an imidazole derivative, a benzimidazole derivative, an azine derivative, a carbazole derivative, or a phenanthroline derivative, or
(3) a high molecular compound.

Examples of the metal complex include tris(8-quinolinolato)aluminum(III) (abbreviation: Alq), tris(4-methyl-8-quinolinolato)aluminum (abbreviation: Almq3), bis(10-hydroxybenzo[h]quinolinato)beryllium (abbreviation: BeBq2), bis(2-methyl-8-quinolinolato)(4-phenylphenolato) aluminum(III) (abbreviation: BAlq), bis(8-quinolinolato) zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ).

Examples of the heteroaromatic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzxazol-2-yl)stilbene (abbreviation: BzOs).

Examples of the high molecular compound include poly[(9,9-dihexylfluorene-2,7-diyl)-co-(pyridine-3,5-diyl)] (abbreviation: PF-Py), and poly[(9,9-dioctylfluorene-2,7-diyl)-co-(2,2'-bipyridine-6,6'-diyl)] (abbreviation: PF-BPy).

The materials are materials having an electron mobility of $10^{-6}$ cm$^2$/Vs or more. Materials other than the above may also be used in the electron transporting layer as long as they are materials high in the electron transporting ability rather than in the hole transporting ability.

The electron transporting layer may be a single-layer, or a multi-layer including two or more layers. For example, the electron transporting layer may be a layer including a first electron transporting layer (anode side) and a second electron transporting layer (cathode side). The first electron transporting layer may be called a hole blocking layer. Each of the two or more electron transporting layers is formed of the above-mentioned electron transporting material.

In the electron transporting layer having a two-layer structure, the compound (1) may be contained in either or both of the first electron transporting layer and the second electron transporting layer.

In one embodiment of the present invention, the compound (1) is preferably contained in the second electron transporting layer, in another embodiment, the compound (1) is preferably contained in the first electron transporting layer, and in a still another embodiment, the compound (1) is preferably contained in the first electron transporting layer and the second electron transporting layer.

Electron Injecting Layer

The electron injecting layer is a layer containing a material having a high electron injection ability. In the electron injecting layer, alkali metals, alkaline earth metals, or compounds thereof such as lithium (Li), cesium (Cs), calcium (Ca), lithium fluoride (LiF), cesium fluoride (CsF), calcium fluoride ($CaF_2$), or lithium oxide ($LiO_x$) may be used. Besides, a material having an electron transporting ability, in which an alkali metal, an alkaline earth metal, or a compound thereof is contained, specifically Alq in which magnesium (Mg) is contained may be used. In this case, electron injection from the cathode may be more efficiently performed.

Otherwise, in the electron injecting layer, a composite material obtained by mixing an organic compound with an electron donor may be used. Such a composite material is excellent in the electron injection ability and the electron transporting ability because the organic compound receives electrons from the electron donor. In this case, the organic compound is preferably a material excellent in transporting received electrons, and specific examples thereof include a material constituting the electron transporting layer as described above (a metal complex, a heteroaromatic compound, etc.). As the electron donor, a material having an electron donation property for the organic compound may be used. Specifically, alkali metals, alkaline earth metals and rare earth metals are preferred, and examples thereof include lithium, cesium, magnesium, calcium, erbium, and ytterbium. Also, alkali metal oxide or alkaline earth metal oxide is preferred, and examples thereof include lithium oxide, calcium oxide, and barium oxide. Also, a Lewis base such as magnesium oxide may also be used. Further, an organic compound such as tetrathiafulvalene (abbreviation: TTF) may also be used. The compound (1) may be contained in the electron injecting layer.

Cathode

It is preferable that a metal, an alloy, an electrically conductive compound, or a mixture thereof which has a low work function (specifically 3.8 eV or less) is used for the cathode. Specific examples of such a cathode material include elements belonging to group 1 or 2 of the periodic table of the elements, that is, alkali metals such as lithium (Li) and cesium (Cs), alkaline earth metals such as magnesium (Mg), calcium (Ca), and strontium (Sr), and alloys containing these (for example, MgAg, and AlLi), and rare earth metals such as europium (Eu), and ytterbium (Yb) and alloys containing these.

When the cathode is formed by using the alkali metals, the alkaline earth metals, and the alloys containing these, a vacuum vapor deposition method or a sputtering method may be used. Also, when a silver paste or the like is used, a coating method, an inkjet method, etc. may be used.

By providing the electron injecting layer, the cathode may be formed using various conductive materials such as Al, Ag, ITO, graphene, and indium oxide-tin oxide containing silicon or silicon oxide regardless of the magnitude of a work function. Such a conductive material may be deposited by using a sputtering method, an inkjet method, a spin coating method or the like.

Insulating Layer

The organic EL device applies an electric field to an ultrathin film, and thus pixel defects are likely to occur due to leaks or short-circuiting. In order to prevent this, an insulating layer formed of an insulating thin film layer may be inserted between a pair of electrodes.

Examples of the material used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, and vanadium oxide. A mixture or a laminate of these may also be used.

Space Layer

The space layer is, for example, a layer provided between a fluorescent light emitting layer and a phosphorescent light emitting layer for the purpose of preventing excitons generated in the phosphorescent light emitting layer from diffusing into the fluorescent light emitting layer, or adjusting a carrier balance, in the case where the fluorescent light emitting layers and the phosphorescent light emitting layers are stacked. The space layer may also be provided between the plurality of phosphorescent light emitting layers. The "carrier" mentioned herein means a charge carrier in a substance.

Since the space layer is provided between the light emitting layers, a material having both an electron transporting ability and a hole transporting ability is preferred. Also, one having a triplet energy of 2.6 eV or more is preferred in order to prevent triplet energy diffusion in the adjacent phosphorescent light emitting layer. Examples of the material used for the space layer include the same as those used for the hole transporting layer as described above.

Blocking Layer

The blocking layer such as the electron blocking layer, the hole blocking layer, or the exciton blocking layer may be provided adjacent to the light emitting layer. The electron blocking layer is a layer that prevents electrons from leaking from the light emitting layer to the hole transporting layer, and the hole blocking layer is a layer that prevents holes from leaking from the light emitting layer to the electron transporting layer. The exciton blocking layer has a function of preventing excitons generated in the light emitting layer from diffusing into the surrounding layers, and trapping the excitons within the light emitting layer. As described above, it is preferable that the hole blocking layer contains the compound (1).

Each layer of the organic EL device may be formed by a conventionally known vapor deposition method, a coating method, etc. For example, formation may be performed by a known method using a vapor deposition method such as a vacuum vapor deposition method, or a molecular beam vapor deposition method (MBE method), or a coating method using a solution of a compound for forming a layer, such as a dipping method, a spin-coating method, a casting method, a bar-coating method, or a roll-coating method.

The film thickness of each layer is not particularly limited, but is usually 5 nm to 10 μm, more preferably 10 nm to 0.2 μm because in general, when the film thickness is too small, defects such as pinholes are likely to occur, and conversely, when the film thickness is too large, a high driving voltage is required and the efficiency decreases.

The organic EL device may be used for electronic devices, such as display components of organic EL panel modules, etc., display devices of televisions, mobile phones, personal computers, etc., and light emitting devices of lightings and vehicular lamps.

EXAMPLES
Hereinafter, the present invention will be described in more detail by using Examples, but the present invention is not limited to the following Examples.
Compounds ET-1, ET-2, ET-3, ET-4, ET-5, ET-6, ET-7 and ET-8 used as the compound (1A) or the compound (1) in the following Examples are as follows.
ET-1
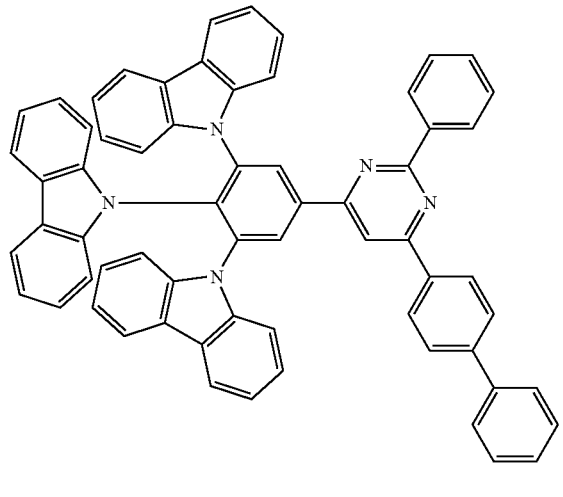
ET-2
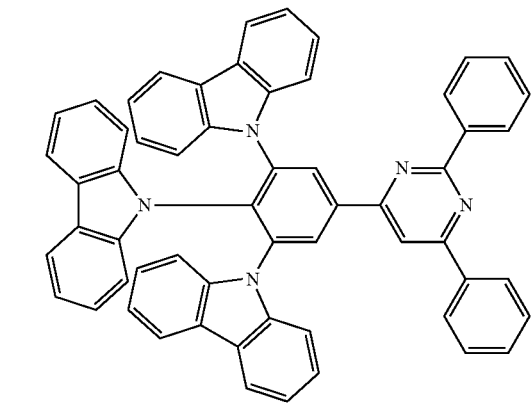
ET-3
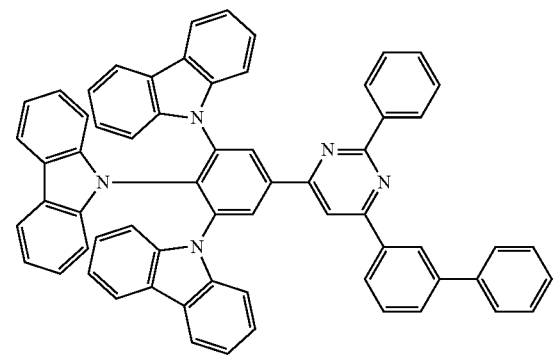
ET-4
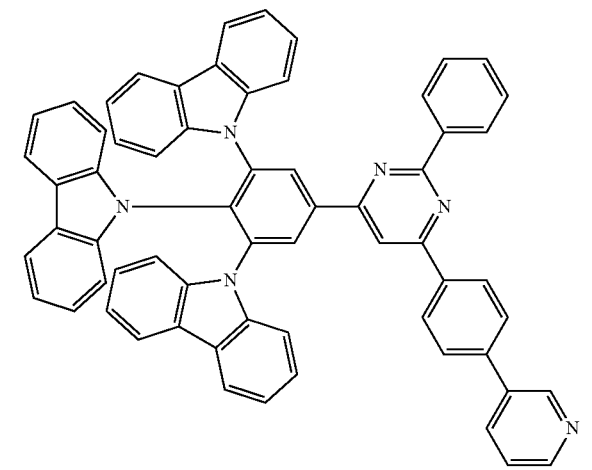
ET-5
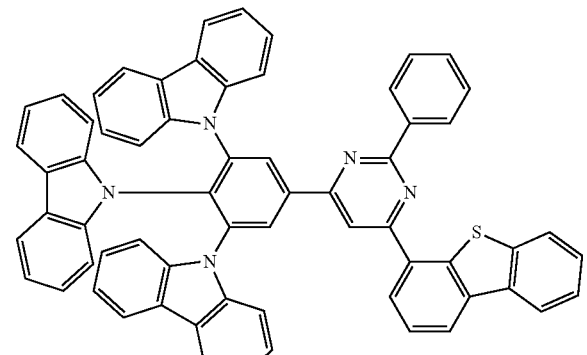
ET-6
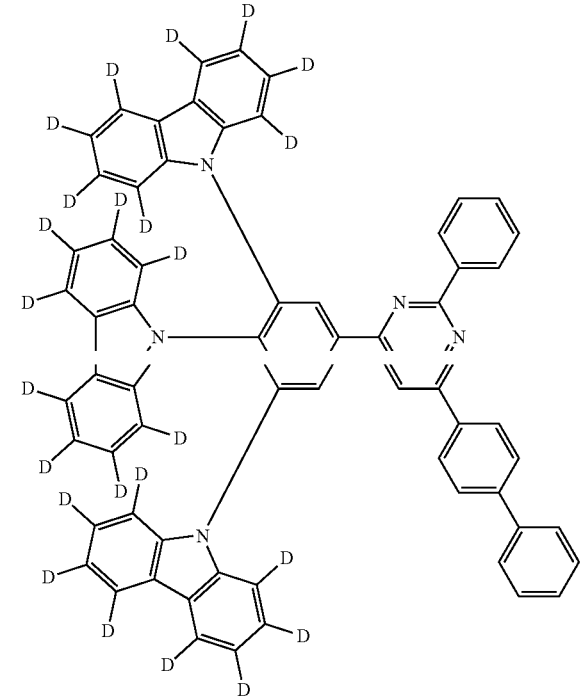

ET-7
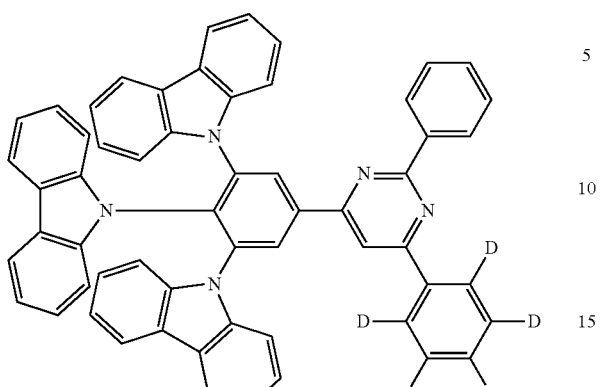
ET-8
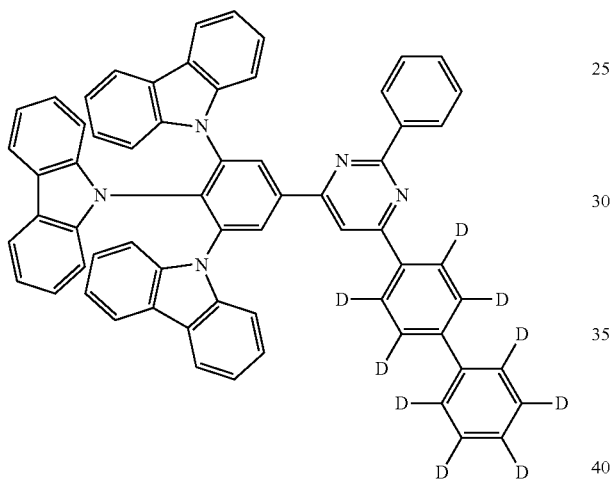
Compounds ET-A, ET-B and ET-C used in place of the compound (1A) and the compound (1) in the following Comparative Examples are as follows.
ET-A
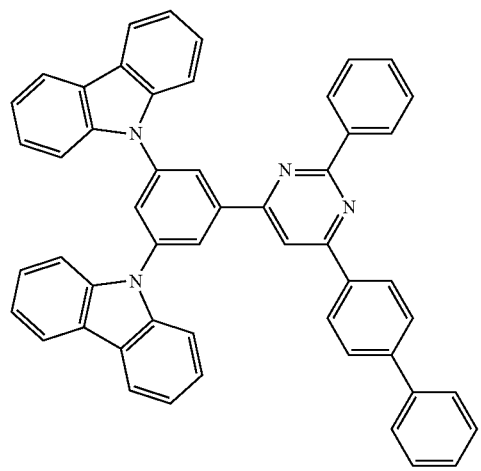
ET-B
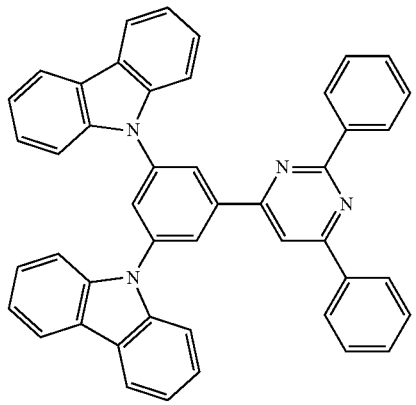
ET-C
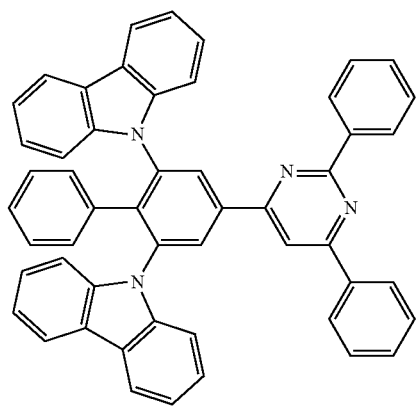
The other compounds used in the following Examples and Comparative Examples are as follows.
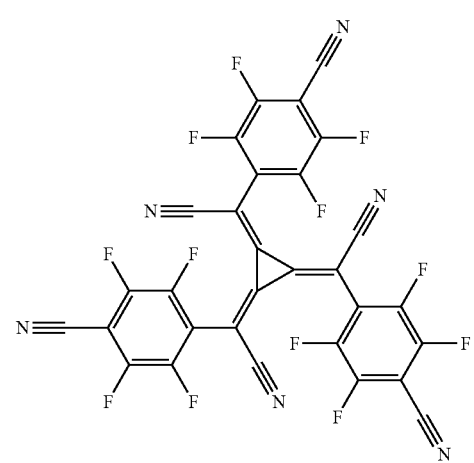
HI-a

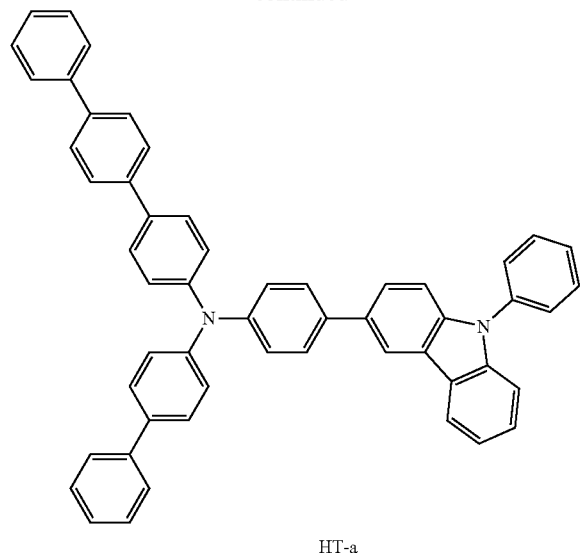
HT-a
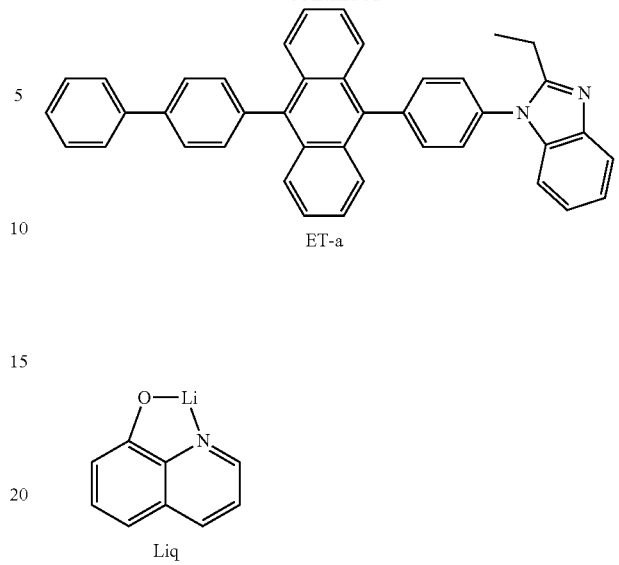
ET-a
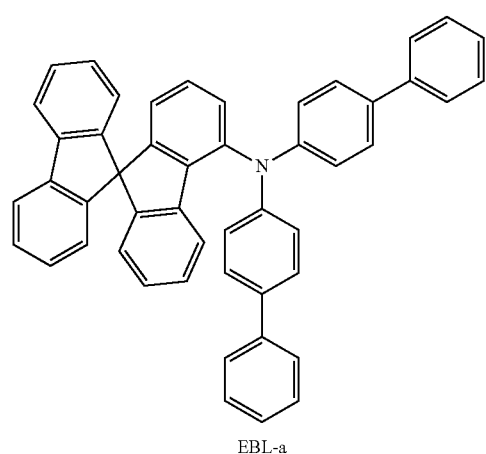
EBL-a
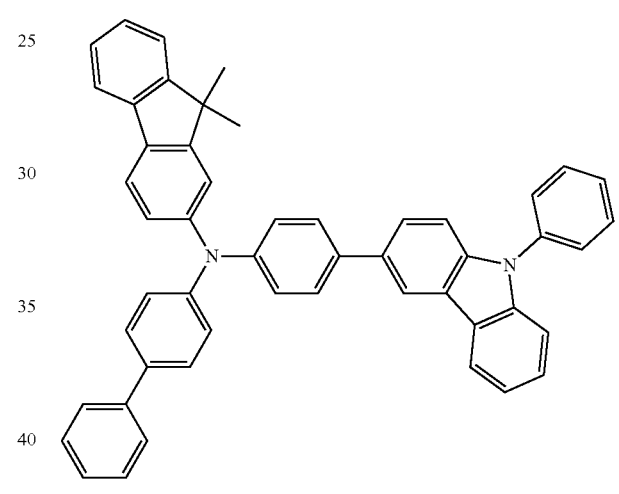
HT-b
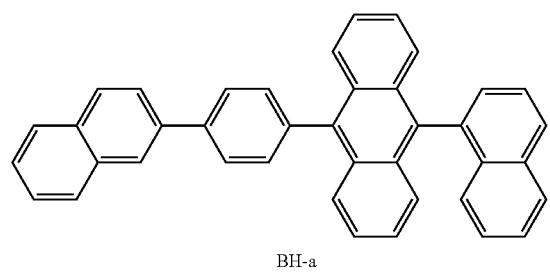
BH-a
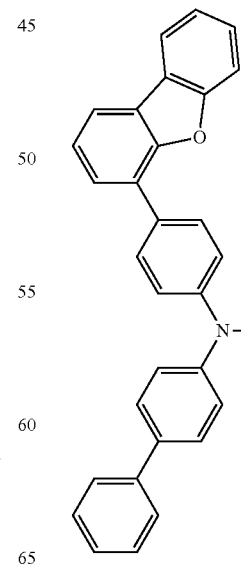
Liq
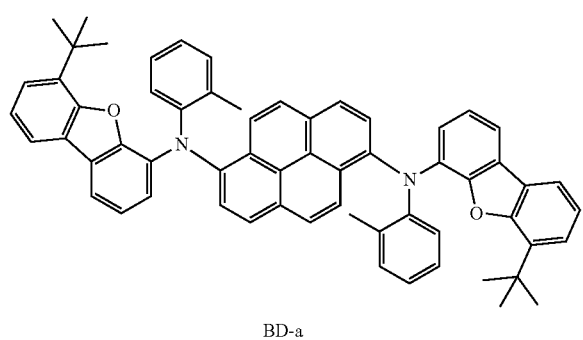
BD-a
EBL-b

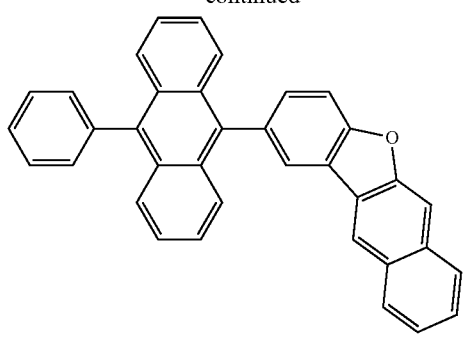

BH-b

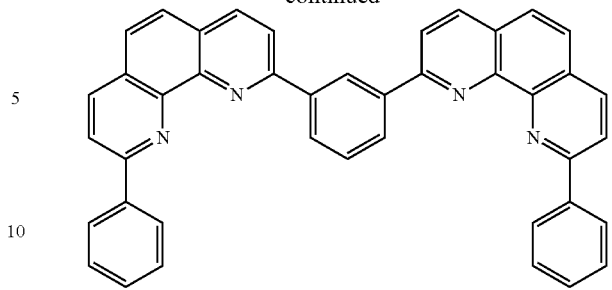

ET-c

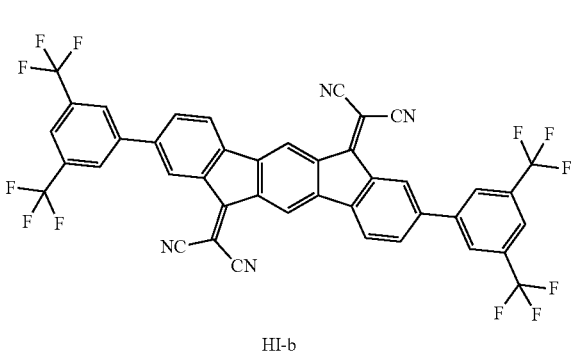

ET-b

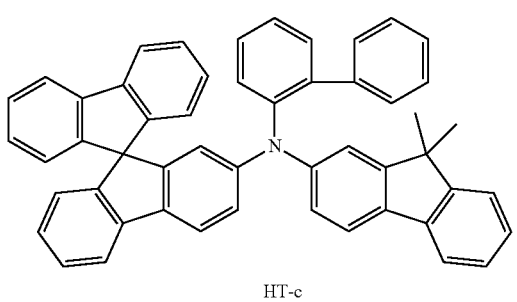

HI-b

HT-c

<Production of Organic EL Device>

Organic EL devices was produced as follows, and the EL device performance of each device was evaluated.

Evaluation methods for EL device performance are as follows.

95% Lifetime (LT95) Evaluation

Regarding the organic EL devices produced in Examples and Comparative Examples, a voltage was applied to the organic EL device so that the current density could be 50 mA/cm$^2$, and the 95% lifetime (LT95) of the device was evaluated. Here, LT95 refers to a time (hr) until the luminance is reduced to 95% of the initial luminance during constant current driving.

90% Lifetime (LT90) Evaluation

Regarding the organic EL devices produced in Examples and Comparative Examples, a voltage was applied to the organic EL device so that the current density could be 50 mA/cm$^2$, and the 90% lifetime (LT90) of the device was evaluated. Here, LT90 refers to a time (hr) until the luminance is reduced to 90% of the initial luminance during constant current driving.

Example 1

A glass substrate (25 mm×75 mm×1.1 mm) provided with an ITO transparent electrode (manufactured by GEO-MATEC Co., Ltd.) was ultrasonically cleaned in isopropyl alcohol for 5 min, and then was subjected to UV ozone cleaning for 30 min. The thickness of the ITO transparent electrode was 130 nm.

The cleaned glass substrate provided with the ITO transparent electrode was mounted on a substrate holder of a vacuum vapor deposition apparatus. First, the above Compound HT-a and the above Compound HI-a were co-deposited so as to cover the ITO transparent electrode to form a hole injecting layer with a film thickness of 10 nm. The concentration of Compound HI-a in the hole injecting layer was 3.0% by mass.

Next, on the hole injecting layer, the above compound HT-a (a first hole transporting layer material) was vapor-deposited so as to form a first hole transporting layer with a film thickness of 80 nm.

Next, on the first hole transporting layer, the above compound EBL-a (a second hole transporting layer material) was vapor-deposited so as to form a second hole transporting layer with a film thickness of 5 nm.

Next, on the second hole transporting layer, the above compound BH-a (a host material) and BD-a (a dopant material) were co-deposited so as to form a light emitting layer with a film thickness of 25 nm. The concentration of Compound BD-a in the light emitting layer was 4.0% by mass.

Next, on the light emitting layer, the above compound ET-1 (a first electron transporting layer material) was vapor-deposited so as to form a first electron transporting layer with a film thickness of 5 nm.

Next, on the first electron transporting layer, the above compound ET-a (a second electron transporting layer material) was vapor-deposited so as to form a second electron transporting layer with a film thickness of 20 nm.

Next, on the second electron transporting layer, LiF was vapor-deposited so as to form an LiF film with a film thickness of 1 nm.

Then, on the LiF film, metal Al was vapor-deposited to form a metal Al cathode with a film thickness of 80 nm.

As in the above, an organic EL device was produced.

A device configuration of Example 1 is schematically illustrated as follows.

ITO(130)/HT-$a$:HI-$a$=97:3(10)/HT-$a$(80)/EBL-$a$(5)/
BH-$a$:BD-$a$=96:4(25)/Compound ET-1(5)/ET-$a$
(20)/LiF(1)/Al(80)

"1" indicates a boundary between a layer and a layer. Numbers in parentheses indicate a film thickness (unit: nm). The ratio is by mass. The same also applies to the corresponding descriptions in the following Examples and the following Comparative Examples.

The organic EL device was evaluated for the 95% lifetime (LT95) thereof. The result is shown in Table 1.

Examples 2 to 8 and Comparative Examples 1 to 3

Organic EL devices of Examples 2 to 8 and Comparative Examples 1 to 3 were produced in the same manner as in Example 1 except that the compound ET-1 (first electron transporting layer material) in Example 1 was changed to the compounds and the comparative compounds shown in Table 1.

The organic EL devices were evaluated for the 95% lifetime (LT95) thereof. The results are shown in Table 1.

TABLE 1

|  | ET | LT95 (hr) |
| --- | --- | --- |
| Example 1 | ET-1 | 330 |
| Example 2 | ET-2 | 264 |
| Example 3 | ET-3 | 315 |
| Example 4 | ET-4 | 340 |
| Example 5 | ET-5 | 320 |
| Example 6 | ET-6 | 330 |
| Example 7 | ET-7 | 260 |
| Example 8 | ET-8 | 325 |
| Comparative Example 1 | ET-A | 169 |
| Comparative Example 2 | ET-B | 54 |
| Comparative Example 3 | ET-C | 51 |

Example 9

A glass substrate (25 mm×75 mm×1.1 mm) provided with an ITO transparent electrode (manufactured by GEO-MATEC Co., Ltd.) was ultrasonically cleaned in isopropyl alcohol for 5 min, and then was subjected to UV ozone cleaning for 30 min. The thickness of the ITO transparent electrode was 130 nm.

The cleaned glass substrate provided with the ITO transparent electrode was mounted on a substrate holder of a vacuum vapor deposition apparatus. First, the above Compound HT-b and the above Compound HI-a were co-deposited so as to cover the ITO transparent electrode to form a hole injecting layer with a film thickness of 10 nm. The concentration of Compound HI-a in the hole injecting layer was 3.0% by mass.

Next, on the hole injecting layer, the above compound HT-b (a first hole transporting layer material) was vapor-deposited so as to form a first hole transporting layer with a film thickness of 80 nm.

Next, on the first hole transporting layer, the above compound EBL-b (a second hole transporting layer material) was vapor-deposited so as to form a second hole transporting layer with a film thickness of 5 nm.

Next, on the second hole transporting layer, the above compound BH-b (a host material) and BD-a (a dopant material) were co-deposited so as to form a light emitting layer with a film thickness of 25 nm. The concentration of Compound BD-a in the light emitting layer was 4.0% by mass.

Next, on the light emitting layer, the above compound ET-1 (a first electron transporting layer material) was vapor-deposited so as to form a first electron transporting layer with a film thickness of 5 nm.

Next, on the first electron transporting layer, the above compound ET-b (a second electron transporting layer material) and Liq were co-deposited so as to form a second electron transporting layer with a film thickness of 20 nm. The concentration of Liq in the second electron transporting layer was 50.0% by mass.

Next, on the second electron transporting layer, LiF was vapor-deposited so as to form an LiF film with a film thickness of 1 nm.

Then, on the LiF film, metal Al was vapor-deposited to form a metal Al cathode with a film thickness of 80 nm.

As in the above, an organic EL device was produced.

A device configuration of Example 9 is schematically illustrated as follows.

ITO(130)/HT-$b$:HI-$a$=97:3(10)/HT-$b$(80)/EBL-$b$(5)/
BH-$b$:BD-$a$=96:4(25)/ET-1(5)/ET-$b$:Li$q$=50:50
(20)/LiF(1)/Al(80)

The organic EL device was evaluated for the 95% lifetime (LT95) thereof. The result is shown in Table 2.

Examples 10 to 11 and Comparative Examples 4 to 6

Organic EL devices of Examples 10 to 11 and Comparative Examples 4 to 6 were produced in the same manner as in Example 9 except that the compound ET-1 (first electron transporting layer material) in Example 9 was changed to the compounds and the comparative compounds shown in Table 2.

The organic EL devices were evaluated for the 95% lifetime (LT95) thereof. The results are shown in Table 2.

TABLE 2

|  | ET | LT95 (hr) |
| --- | --- | --- |
| Example 9 | ET-1 | 235 |
| Example 10 | ET-2 | 211 |
| Example 11 | ET-5 | 230 |
| Comparative Example 4 | ET-A | 150 |
| Comparative Example 5 | ET-B | 95 |
| Comparative Example 6 | ET-C | 61 |

Example 12

A glass substrate (25 mm×75 mm×1.1 mm) provided with an ITO transparent electrode (manufactured by GEO- MATEC Co., Ltd.) was ultrasonically cleaned in isopropyl alcohol for 5 min, and then was subjected to UV ozone cleaning for 30 min. The thickness of the ITO transparent electrode was 130 nm.

The cleaned glass substrate provided with the ITO transparent electrode was mounted on a substrate holder of a vacuum vapor deposition apparatus. First, the above Compound HI-b was vapor-deposited so as to cover the ITO transparent electrode to form a hole injecting layer with a film thickness of 5 nm.

Next, on the hole injecting layer, the above compound HT-c (a first hole transporting layer material) was vapor-deposited so as to form a first hole transporting layer with a film thickness of 80 nm.

Next, on the first hole transporting layer, the above compound EBL-a (a second hole transporting layer material) was vapor-deposited so as to form a second hole transporting layer with a film thickness of 10 nm.

Next, on the second hole transporting layer, the above compound BH-a (a host material) and BD-a (a dopant material) were co-deposited so as to form a light emitting layer with a film thickness of 25 nm. The concentration of Compound BD-a in the light emitting layer was 4.0% by mass.

Next, on the light emitting layer, the above compound ET-1 (a first electron transporting layer material) was vapor-deposited so as to form a first electron transporting layer with a film thickness of 10 nm.

Next, on the first electron transporting layer, the above compound ET-c (a second electron transporting layer material) and Li were co-deposited so as to form a second electron transporting layer with a film thickness of 15 nm. The concentration of Li in the second electron transporting layer was 4.0% by mass.

Then, on the second electron transporting layer, metal Al was vapor deposited to form a metal Al cathode with a film thickness of 80 nm.

As in the above, an organic EL device was produced.

A device configuration of Example 12 is schematically illustrated as follows.

ITO(130)/HI-b(5)/HT-c(80)/EBL-a(10)/BH-a:BD-a=96:4(25)/ET-1(10)/ET-c:Li=96:4(15)/Al(80)

The organic EL device was evaluated for the 90% lifetime (LT90) thereof. The result is shown in Table 3.

Comparative Example 7

An organic EL device of Comparative Example 7 was produced in the same manner as in Example 12 except that the compound ET-1 (first electron transporting layer material) in Example 5 was changed to the compound and the comparative compound shown in Table 2.

The organic EL devices were evaluated for the 90% lifetime (LT90) thereof. The results are shown in Table 3.

TABLE 3

| | ET | LT90 (hr) |
|---|---|---|
| Example 12 | ET-1 | 753 |
| Comparative Example 7 | ET-A | 401 |

As obvious from the results in Tables 1 to 3, the organic EL devices containing any of the compounds ET-1 to ET-8 of the formula (1A) of the present invention have a long lifetime. In particular, the organic EL devices containing any of the compounds ET-1, ET-3 to ET-6 and ET-8 corresponding to the formula (1) of the present invention have a further longer lifetime as compared with the organic EL devices containing the compound ET-2 or ET-7.

On the other hand, the organic EL devices containing any of the comparative compounds ET-A, ET-B and ET-C are insufficient in point of the lifetime thereof.

From comparison between Examples and Comparative Examples, it is known that the compounds having a mother nucleus common to the formulae (1A) and (1) to (17), that is, a mother nucleus in which the specific four ring carbon atoms of one benzene ring bond to the 9-position of each of the three carbazole skeletons and to the 4-position of one pyrimidine skeleton substituted with a benzene ring skeleton at the 2-position, and in which the 6-position of the pyrimidine skeleton is substituted with a specific structure, have a long lifetime.

Synthesis Example 1—Synthesis of Compound ET-1

(1-1) Synthesis of Intermediate A

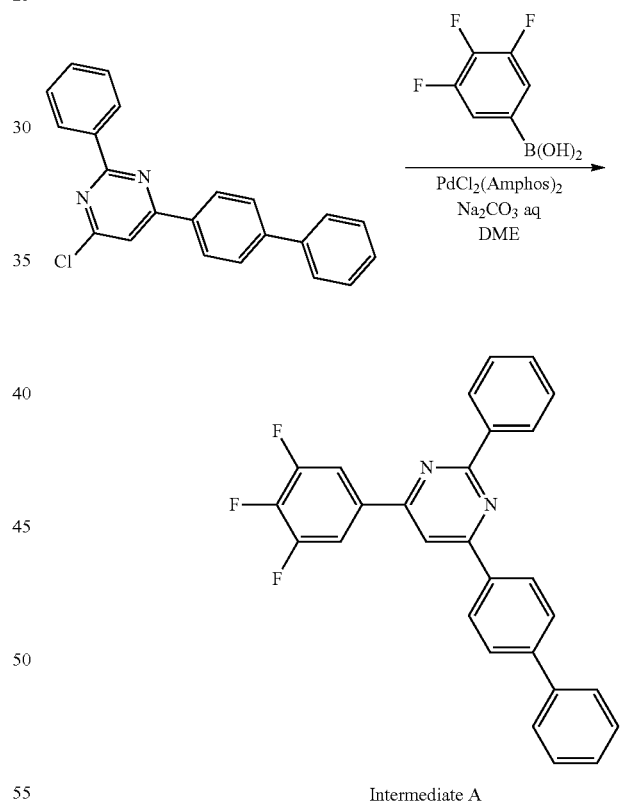

Intermediate A 7.5 g of 4-([1,1'-biphenyl]-4-yl)-6-chloro-2-phenylpyrimidine, 4.6 g of 3,4,5-trifluorophenylboronic acid, 0.45 g of PdCl$_2$(Amphos)$_2$, 220 mL of 1,2-dimethoxyethane (DME), and 33 mL of an aqueous 2 M sodium carbonate solution were put into a flask, purged with argon gas, and heated with stirring for 7 hours under reflux. After this was restored to room temperature, the precipitated solid was collected through filtration, and purified by silica gel column chromatography to give 9.2 g of the intermediate A (yield 96%) as a white solid.

(1-2) Synthesis of Compound ET-1

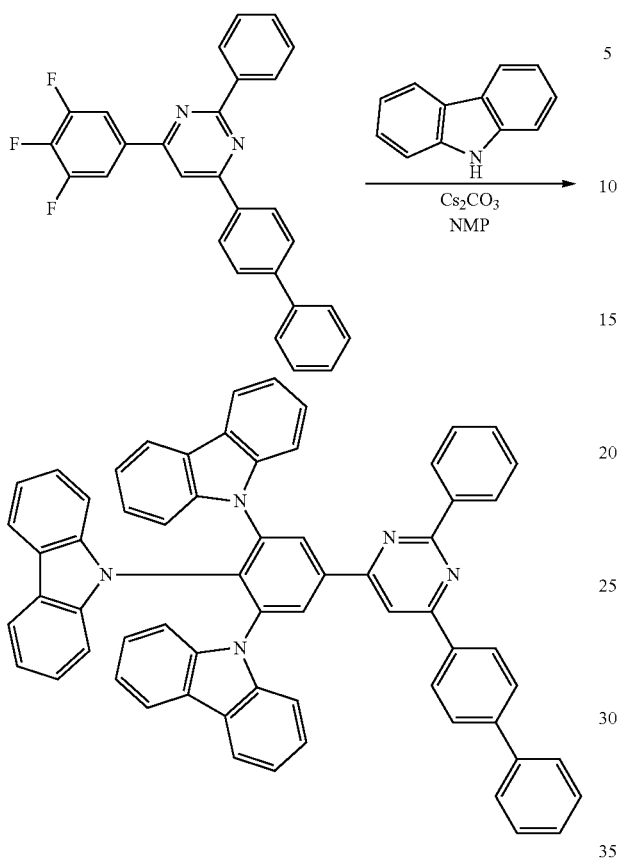

3.0 g of the intermediate A, 5.7 g of carbazole, 13.4 g of cerium carbonate and 35 mL of N-methylpyrrolidone (NMP) were put into a flask, purged with argon gas, and heated with stirring at 155° C. for 2 days. After this was restored to room temperature, methanol was added to the reaction liquid, and the precipitated solid was collected through filtration. The solid was washed with water and acetone, and purified by repeated recrystallization with toluene to give 4.7 g of the compound ET-1 (yield 78%) as a white solid. As a result of mass spectrometry, m/e=880, which identified the intended product.

Synthesis Example 2—Synthesis of Compound ET-2

(2-1) Synthesis of Intermediate B

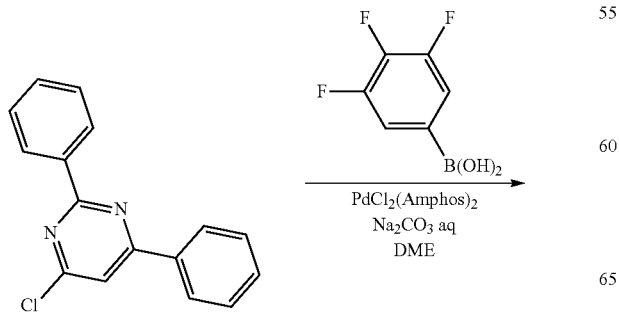

4.1 g of 4-chloro-2,6-diphenylpyrimidine, 3.0 g of 3,4,5-trifluorophenylboronic acid, 0.55 g of $PdCl_2(Amphos)_2$, 150 mL of 1,2-dimethoxyethane (DME), and 25 mL of an aqueous 2 M sodium carbonate solution were put into a flask, purged with argon gas, and heated with stirring for 7 hours under reflux. After this was restored to room temperature, the precipitated solid was collected through filtration, and purified by silica gel column chromatography to give 5.1 g of the intermediate B (yield 90%) as a white solid.

(2-2) Synthesis of Compound ET-2

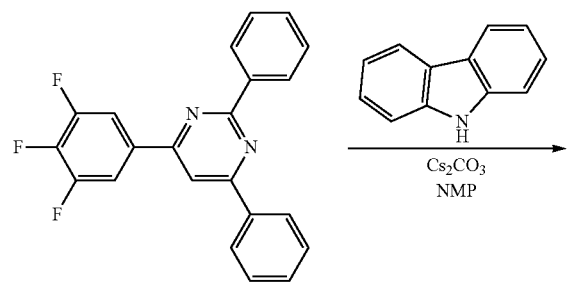

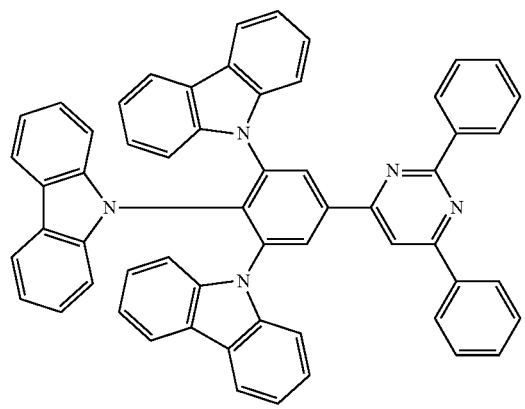

3 g of the intermediate B, 6.9 g of carbazole, 16.2 g of cerium carbonate and 80 mL of N-methylpyrrolidone (NMP) were put into a flask, purged with argon gas, and heated with stirring at 155° C. for 2 days. After this was restored to room temperature, methanol was added to the reaction liquid, and the precipitated solid was collected through filtration. The solid was washed with water and acetone, and then purified by repeated recrystallization with toluene to give 5.7 g of the compound ET-2 (yield 86%) as a white solid. As a result of mass spectrometry, m/e=803, which identified the intended product.

Synthesis Example 3—Synthesis of Compound ET-3

(3-1) Synthesis of Intermediate C

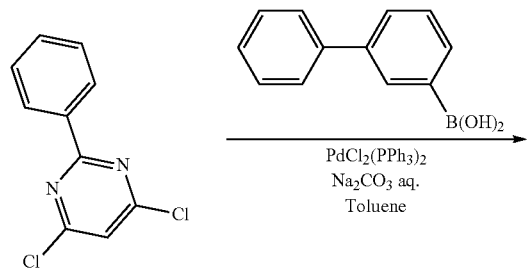

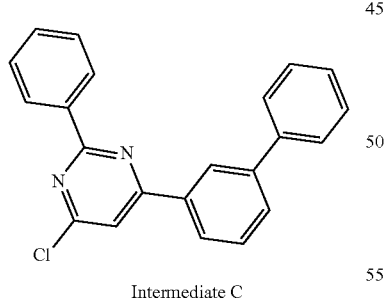

Intermediate C 5.0 g of 4,6-dichloro-2-phenylpyrimidine, 4.4 g of m-biphenylboronic acid, 0.16 g of PdCl$_2$(PPh$_3$)$_2$, 200 mL of toluene and 25 mL of an aqueous 2 M sodium carbonate solution were put into a flask, purged with argon gas, and heated with stirring for 7 hours under reflux. After this was restored to room temperature, the precipitated solid was collected through filtration, and purified by silica gel column chromatography to give 4.7 g of the intermediate C (yield 61%) as a white solid.

Subsequently, according to the same process as in Synthesis Example 1, the compound ET-3 was produced.

As a result of mass spectrometry, m/e=880, which identified the intended product.

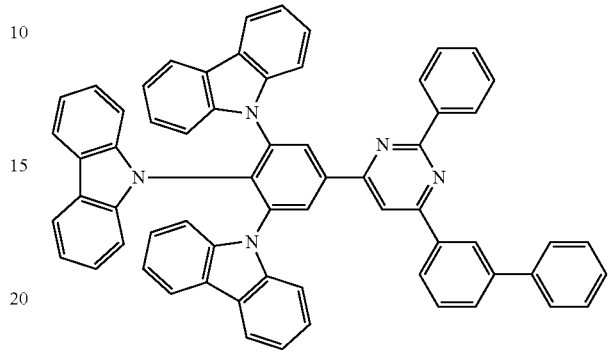

ET-3

Synthesis Example 4—Synthesis of Compound ET-4

(4-1) Synthesis of Intermediate D

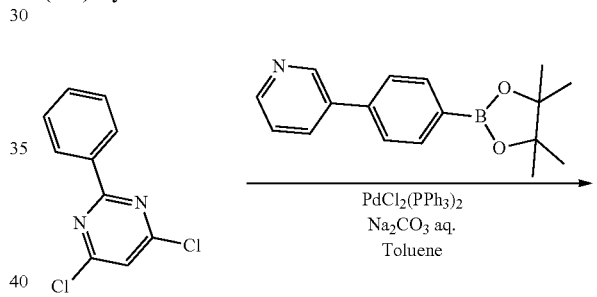

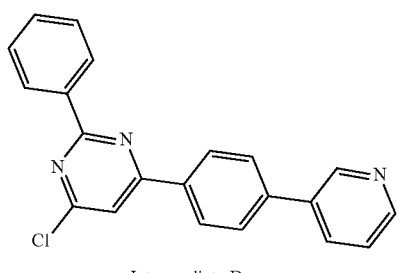

Intermediate D 5.0 g of 4,6-dichloro-2-phenylpyrimidine, 6.3 g of 2-(4-(3-pyridyl)phenyl)-4,4,5,5-tetramethyl-1,3,2-dioxaborolane, 0.16 g of PdCl$_2$(PPh$_3$)$_2$, 200 mL of toluene and 25 mL of an aqueous 2 M sodium carbonate solution were put into a flask, purged with argon gas, and heated with stirring for 7 hours under reflux. After this was restored to room temperature, the precipitated solid was collected through filtration, and purified by silica gel column chromatography to give 5.3 g of the intermediate D (yield 69%) as a white solid.

Subsequently, according to the same process as in Synthesis Example 1, the compound ET-4 was produced.

As a result of mass spectrometry, m/e=881, which identified the intended product.

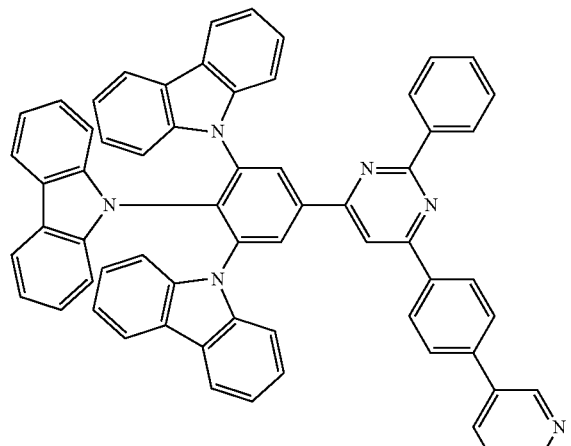

ET-4

Synthesis Example 5—Synthesis of Compound ET-5

(5-1) Synthesis of Intermediate E

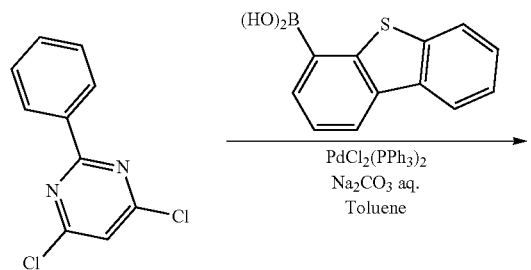

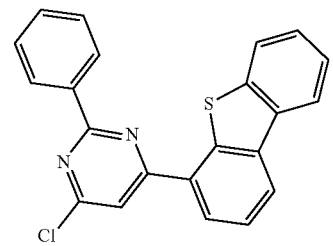

Intermediate E

According to the same process as (3-1) in Synthesis Example 3, the intermediate E was produced.

Subsequently, according to the same process as in Synthesis Example 1, the compound ET-5 was produced.

As a result of mass spectrometry, m/e=910, which identified the intended product.

ET-5

Synthesis Example 6—Synthesis of Compound ET-6

In (1-2) in Synthesis Example 1, carbazole-d8 was used in place of carbazole, and according to the same process as therein, the compound ET-6 was produced.

As a result of mass spectrometry, m/e=904, which identified the intended product.

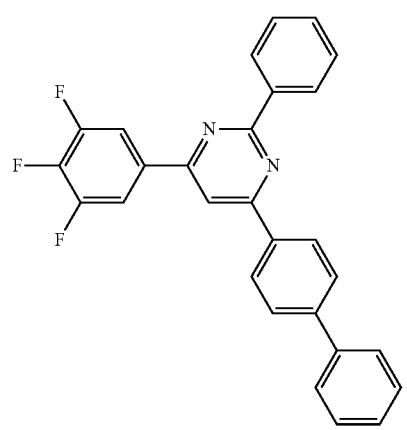
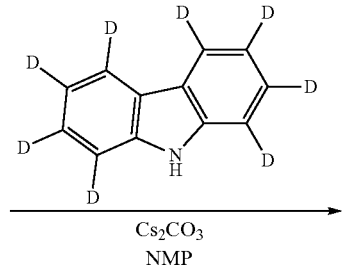

Cs₂CO₃
NMP

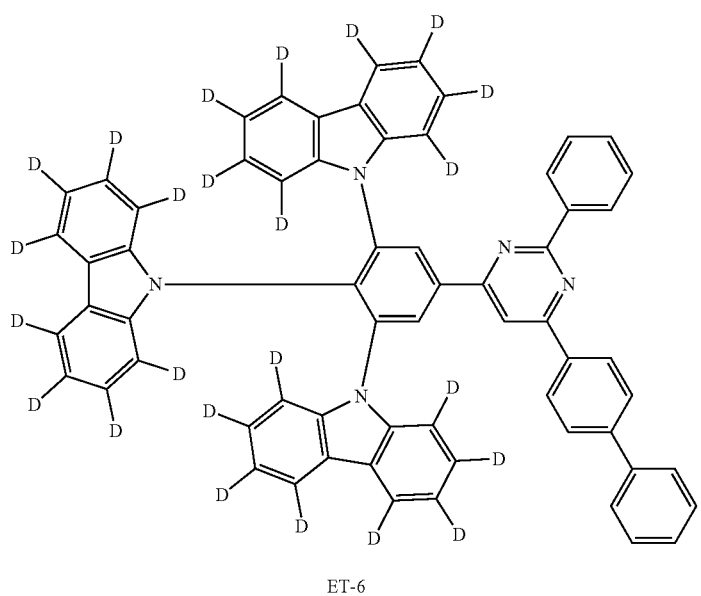

ET-6

Synthesis Example 7—Synthesis of Compound ET-7

(7-1) Synthesis of Intermediate F

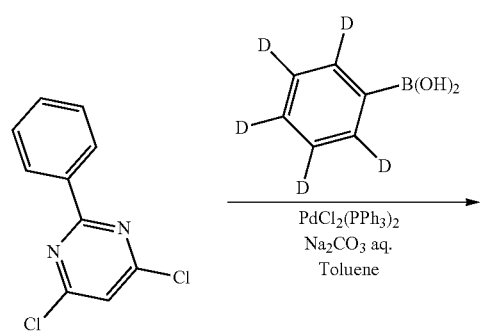

PdCl₂(PPh₃)₂
Na₂CO₃ aq.
Toluene

-continued

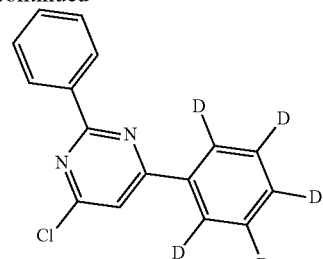

Intermediate F

According to the same process as (3-1) in Synthesis Example 3, the intermediate F was produced.

Subsequently, according to the same process as in Synthesis Example 1, the compound ET-7 was produced.

As a result of mass spectrometry, m/e=809, which identified the intended product.

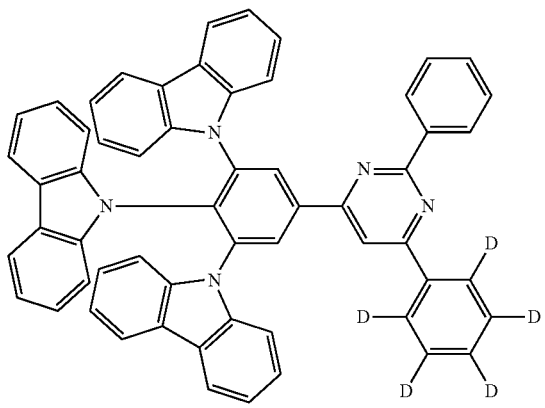

ET-7

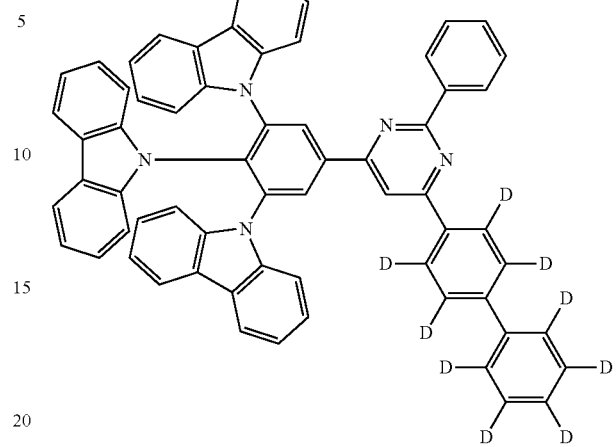

ET-8

Synthesis Example 8—Synthesis of Compound ET-8

(8-1) Synthesis of Intermediate G

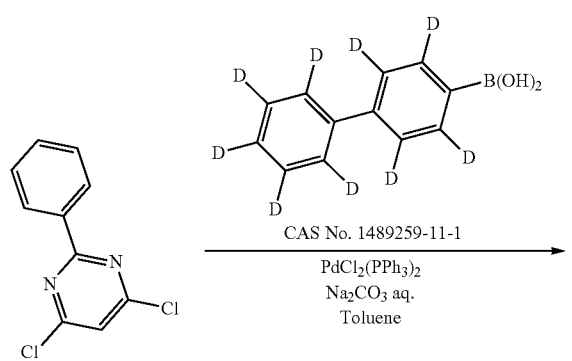

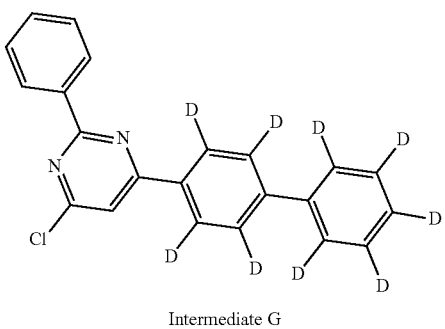

Intermediate G

According to the same process as (3-1) in Synthesis Example 3, the intermediate G was produced.

Subsequently, according to the same process as in Synthesis Example 1, the compound ET-8 was produced.

As a result of mass spectrometry, m/e=889, which identified the intended product.

REFERENCE SIGNS LIST 1, 11, 12 Organic EL Device
2 Substrate
3 Anode
4 Cathode
5 Light Emitting Layer
6 Hole Transporting Zone (hole transporting layer)
6a First Hole Transporting Layer
6b Second Hole Transporting Layer
7 Electron Transporting Zone (electron transporting layer)
7a First Electron Transporting Layer
7b Second Electron Transporting Layer
8 Hole Blocking Layer
10, 20, 30 Light Emitting Unit

The invention claimed is:

1. An organic electroluminescent device comprising:
a cathode, an anode, and organic layers disposed between the cathode and the anode, wherein:
the organic layers comprise a light-emitting layer, and a first layer disposed between the light-emitting layer and the cathode, and
the first layer comprises a compound of formula (1A):

(1A)

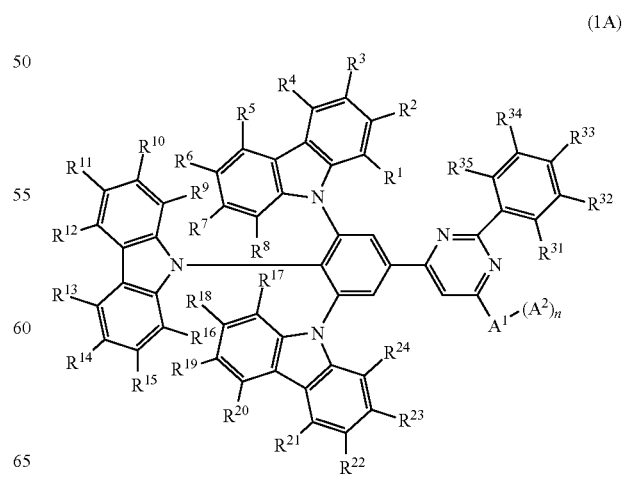

wherein,

R$^1$ to R$^{24}$ each independently represent a hydrogen atom, a substituted or unsubstituted aryl group having 6 to 30 ring carbon atoms, or a substituted or unsubstituted heteroaryl group having 5 to 30 ring atoms R$^{31}$ to R$^{35}$ each independently represent a hydrogen atom A$^1$ represents a substituted or unsubstituted, (n+1)-valent residue of an aromatic hydrocarbon having 6 to 30 ring carbon atoms, or a substituted or unsubstituted, (n+1)-valent residue of an aromatic heterocyclic compound having 5 to 30 ring atoms, wherein a hydrogen atom represents a protium isotope and/or a deuterium isotope, A$^2$ each independently represents a substituted or unsubstituted aryl group having 6 to 30 ring carbon atoms, or a substituted or unsubstituted heteroaryl group having 5 to 30 ring atoms, and n represents an integer of 1 to 3.

2. The organic electroluminescent device according to claim 1, wherein when A$^1$ is an (n+1)-valent residue of benzene.

3. The organic electroluminescent device according to claim 1, wherein:

the aromatic hydrocarbon having 6 to 30 ring carbon atoms of the substituted or unsubstituted, (n+1)-valent residue of the aromatic hydrocarbon having 6 to 30 ring carbon atoms represented by A$^1$ is a benzene, a biphenyl, a terphenyl, a naphthalene, an anthracene, a benzanthracene, a phenanthrene, a benzophenanthrene, a phenalene, a picene, a pentaphene, a pyrene, a chrysene, a benzochrysene, a fluorene, a fluoranthene, a perylene, or a triphenyl, and the aromatic heterocyclic compound having 5 to 30 ring atoms of the substituted or unsubstituted, (n+1)-valent residue of the aromatic heterocyclic compound having 5 to 30 ring atoms represented by A$^1$ is a pyrrole, a furan, a thiophene, a pyridine, a pyridazine, a pyrimidine, a pyrazine, a triazine, an imidazole, an oxazole, a thiazole, a pyrazole, an isoxazole, an isothiazole, an oxadiazole, a thiadiazole, a triazole, a tetrazole, an indole, an isoindole, a benzofuran, an isobenzofuran, a benzothiophene, an isobenzothiophene, an indolizine, a quinolidine, a quinoline, an isoquinoline, a cinnoline, a phthalazine, a quinazoline, a quinoxaline, a benzimidazole, a benzoxazole, a benzothiazole, an indazole, a benzisoxazole, a benzisothiazole, a dibenzofuran, a dibenzothiophene, a carbazole, a phenanthridine, an acridine, a phenanthroline, a phenazine, a phenothiazine, a phenoxazine, a xanthene or a benzonitrile.

4. The organic electroluminescent device according to claim 1, wherein:

the aromatic hydrocarbon having 6 to 30 ring carbon atoms of the substituted or unsubstituted, (n+1)-valent residue of the aromatic hydrocarbon having 6 to 30 ring carbon atoms represented by A$^1$ is a benzene, a biphenyl, a naphthalene or a phenanthrene, and the aromatic heterocyclic compound having 5 to 30 ring atoms of the substituted or unsubstituted, (n+1)-valent residue of the aromatic heterocyclic compound having 5 to 30 ring atoms represented by A$^1$ is a pyridine, a dibenzofuran, a dibenzothiophene, a carbazole or a benzonitrile.

5. The organic electroluminescent device according to claim 1, wherein:

the aryl group having 6 to 30 ring carbon atoms of the substituted or unsubstituted aryl group having 6 to 30 ring carbon atoms represented by A$^2$ is a monovalent residue of a benzene, a biphenyl, a terphenyl, a naphthalene, an anthracene, a benzanthracene, a phenanthrene, a benzophenanthrene, a phenalene, a picene, a pentaphene, a pyrene, a chrysene, a benzochrysene, a fluorene, a fluoranthene, a perylene, or a triphenyl, and the heteroaryl group having 5 to 30 ring atoms of the substituted or unsubstituted heteroaryl group having 5 to 30 ring atoms represented by A$^2$ is a monovalent residue of a pyrrole, a furan, a thiophene, a pyridine, a pyridazine, a pyrimidine, a pyrazine, a triazine, an imidazole, an oxazole, a thiazole, a pyrazole, an isoxazole, an isothiazole, an oxadiazole, a thiadiazole, a triazole, a tetrazole, an indole, an isoindole, a benzofuran, an isobenzofuran, a benzothiophene, an isobenzothiophene, an indolizine, a quinolidine, a quinoline, an isoquinoline, a cinnoline, a phthalazine, a quinazoline, a quinoxaline, a benzimidazole, a benzoxazole, a benzothiazole, an indazole, a benzisoxazole, a benzisothiazole, a dibenzofuran, a dibenzothiophene, a carbazole, a phenanthridine, an acridine, a phenanthroline, a phenazine, a phenothiazine, a phenoxazine, a xanthene or a benzonitrile.

6. The organic electroluminescent device according to claim 1, wherein:

the aryl group having 6 to 30 ring carbon atoms of the substituted or unsubstituted aryl group having 6 to 30 ring carbon atoms represented by A$^2$ is a monovalent residue of a benzene, a biphenyl, a naphthalene or a phenanthrene, and the heteroaryl group having 5 to 30 ring atoms of the substituted or unsubstituted heteroaryl group having 5 to 30 ring atoms represented by A$^2$ is monovalent residue of a pyridine, a dibenzofuran, a dibenzothiophene, a carbazole or a benzonitrile.

7. The organic electroluminescent device according to claim 1, wherein:

R$^1$ to R$^{24}$ each independently is a substituted or unsubstituted aryl group having 6 to 30 ring carbon atoms, and the arbitrary substituent to be meant by the wording "substituted or unsubstituted" by any of R$^1$ to R$^{24}$, A$^1$ and A$^2$ each is independently an unsubstituted aryl group having 6 to 30 ring carbon atoms, or an unsubstituted alkyl group having 1 to 50 carbon atoms.

8. The organic electroluminescent device according to claim 1, wherein:

R$^1$ to R$^{24}$ are hydrogen atoms,

A$^1$ is an unsubstituted (n+1)-valent residue of an aromatic hydrocarbon having 6 to 30 ring carbon atoms, or an unsubstituted (n+1)-valent residue of an aromatic heterocyclic compound having 5 to 30 ring atoms, and A$^2$ is an unsubstituted aryl group having 6 to 30 ring carbon atoms, or an unsubstituted heteroaryl group having 5 to 30 ring atoms.

9. An organic electroluminescent device, comprising:

a cathode, an anode, and organic layers disposed between the cathode and the anode, wherein:

the organic layers comprise a light-emitting layer, and a first layer disposed between the light-emitting layer and the cathode, and the first layer comprises a compound of formula (2):

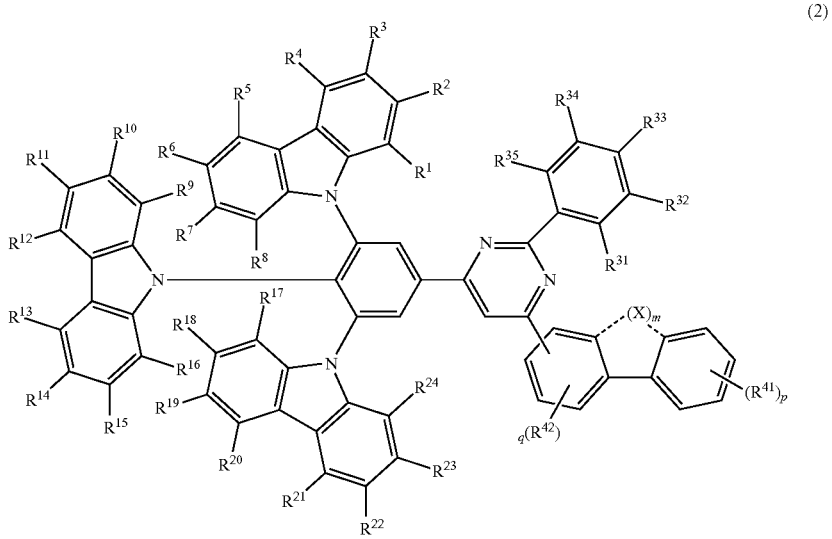

(2)

wherein:
R$^1$ to R$^{24}$ each independently represent a hydrogen atom, or a substituent, and the substituent is a substituted or unsubstituted aryl group having 6 to 30 ring carbon atoms, or a substituted or unsubstituted heteroaryl group having 5 to 30 ring atoms,
R31 to R35 each independently represent a hydrogen atom,
R$^{41}$ to R$^{42}$ each are independently same as R$^1$,
m represents 0 or 1,
when m is 0, X is absent, and the two benzene rings are not crosslinked,
when m is 1, X is O or S,
p represents an integer of 0 to 5,
q represents an integer of 0 to 4.

10. The organic electroluminescent device according to claim 1, wherein the compound represented by the formula (1A) is a compound of formula (3):

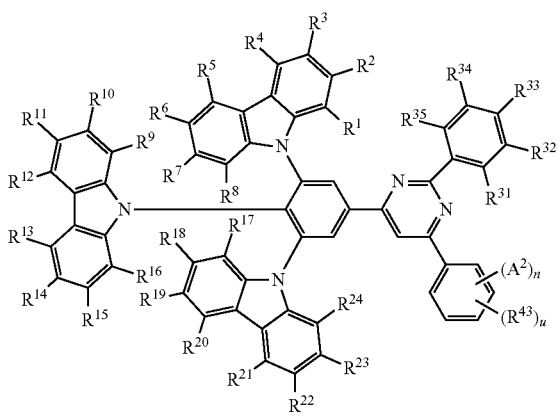

(3)

wherein:
A$^2$ is an unsubstituted aryl group having 6 to 30 ring carbon atoms, or an unsubstituted heteroaryl group having 5 to 30 ring atoms,
R$^{43}$ is the same as R$^1$, and
u represents an integer of 0 to (5-n).

11. The organic electroluminescent device according to claim 1, wherein at least one hydrogen atom in the compound represented by the formula (1A) is a deuterium atom.

12. The organic electroluminescent device according to claim 1, wherein R$^1$ to R$^{24}$ are all deuterium atoms.

13. The organic electroluminescent device according to claim 1, wherein:
n is 1,
the group represented by A$^1$ is unsubstituted, and
the hydrogen atoms that the group represented by A$^1$ has are all deuterium atoms.

14. The organic electroluminescent device according to claim 1, wherein:
n is 1,
the group represented by A$^1$ is unsubstituted,
the hydrogen atoms that the group represented by A$^1$ has are all deuterium atoms,
the group represented by A$^2$ is unsubstituted, and
the hydrogen atoms that the group represented by A$^2$ has are all deuterium atoms.

15. The organic electroluminescent device according to claim 1, wherein the first layer is adjacent to the light emitting layer.

16. A compound of formula (1):

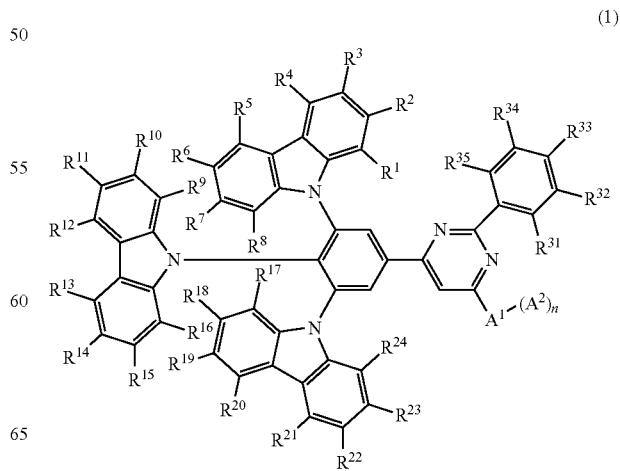

(1)

wherein:

R¹ to R²⁴ each independently represent a hydrogen atom, or a substituent, and the substituent is a substituted or unsubstituted aryl group having 6 to 30 ring carbon atoms, or a substituted or unsubstituted heteroaryl group having 5 to 30 ring atoms, R³¹ to R³⁵ each independently represent a hydrogen atom A¹ represents a substituted or unsubstituted, (n+1)-valent residue of an aromatic hydrocarbon having 6 to 30 ring carbon atoms, or a substituted or unsubstituted, (n+1)-valent residue of an aromatic heterocyclic compound having 5 to 30 ring atoms, wherein a hydrogen atom represents a protium isotope and/or a deuterium isotope, A² each independently represents a substituted or unsubstituted aryl group having 6 to 30 ring carbon atoms, or a substituted or unsubstituted heteroaryl group having 5 to 30 ring atoms, and n represents an integer of 1 to 3.

17. The compound according to claim 16, wherein:

the aromatic hydrocarbon having 6 to 30 ring carbon atoms of the substituted or unsubstituted, mono or di-valent residue of the aromatic hydrocarbon having 6 to 30 ring carbon atoms represented by A¹ is a benzene, a biphenyl, a terphenyl, a naphthalene, an anthracene, a benzanthracene, a phenanthrene, a benzophenanthrene, a phenalene, a picene, a pentaphene, a pyrene, a chrysene, a benzochrysene, a fluorene, a fluoranthene, a perylene, or a triphenyl, and the aromatic heterocyclic compound having 5 to 30 ring atoms of the substituted or unsubstituted, mono or di-valent residue of the aromatic heterocyclic compound having 5 to 30 ring atoms represented by A¹ is a pyrrole, a furan, a thiophene, a pyridine, a pyridazine, a pyrimidine, a pyrazine, a triazine, an imidazole, an oxazole, a thiazole, a pyrazole, an isoxazole, an isothiazole, an oxadiazole, a thiadiazole, a triazole, a tetrazole, an indole, an isoindole, a benzofuran, an isobenzofuran, a benzothiophene, an isobenzothiophene, an indolizine, a quinolidine, a quinoline, an isoquinoline, a cinnoline, a phthalazine, a quinazoline, a quinoxaline, a benzimidazole, a benzoxazole, a benzothiazole, an indazole, a benzisoxazole, a benzisothiazole, a dibenzofuran, a dibenzothiophene, a carbazole, a phenanthridine, an acridine, a phenanthroline, a phenazine, a phenothiazine, a phenoxazine, a xanthene or a benzonitrile.

18. The compound according to claim 16, wherein:

the aromatic hydrocarbon having 6 to 30 ring carbon atoms of the substituted or unsubstituted, mono or di-valent residue of the aromatic hydrocarbon having 6 to 30 ring carbon atoms represented by A¹ is a benzene, a biphenyl, a naphthalene or a phenanthrene, and the aromatic heterocyclic compound having 5 to 30 ring atoms of the substituted or unsubstituted, mono or di-valent residue of the aromatic heterocyclic compound having 5 to 30 ring atoms represented by A¹ is a pyridine, a dibenzofuran, a dibenzothiophene, a carbazole or a benzonitrile.

19. The compound according to claim 16, wherein:

the aryl group having 6 to 30 ring carbon atoms of the substituted or unsubstituted aryl group having 6 to 30 ring carbon atoms represented by A² is a monovalent residue of a benzene, a biphenyl, a terphenyl, a naphthalene, an anthracene, a benzanthracene, a phenanthrene, a benzophenanthrene, a phenalene, a picene, a pentaphene, a pyrene, a chrysene, a benzochrysene, a fluorene, a fluoranthene, a perylene, or a triphenyl, and the heteroaryl group having 5 to 30 ring atoms of the substituted or unsubstituted heteroaryl group having 5 to 30 ring atoms represented by A² is a monovalent residue of a pyrrole, a furan, a thiophene, a pyridine, a pyridazine, a pyrimidine, a pyrazine, a triazine, an imidazole, an oxazole, a thiazole, a pyrazole, an isoxazole, an isothiazole, an oxadiazole, a thiadiazole, a triazole, a tetrazole, an indole, an isoindole, a benzofuran, an isobenzofuran, a benzothiophene, an isobenzothiophene, an indolizine, a quinolidine, a quinoline, an isoquinoline, a cinnoline, a phthalazine, a quinazoline, a quinoxaline, a benzimidazole, a benzoxazole, a benzothiazole, an indazole, a benzisoxazole, a benzisothiazole, a dibenzofuran, a dibenzothiophene, a carbazole, a phenanthridine, an acridine, a phenanthroline, a phenazine, a phenothiazine, a phenoxazine, a xanthene or a benzonitrile.

20. The compound according to claim 16, wherein:

the aryl group having 6 to 30 ring carbon atoms of the substituted or unsubstituted aryl group having 6 to 30 ring carbon atoms represented by A² is a monovalent residue of a benzene, a biphenyl, a naphthalene or a phenanthrene, and the heteroaryl group having 5 to 30 ring atoms of the substituted or unsubstituted heteroaryl group having 5 to 30 ring atoms represented by A² is monovalent residue of a pyridine, a dibenzofuran, a dibenzothiophene, a carbazole or a benzonitrile.

21. The compound according to claim 16, wherein:

the substituent represented by R¹ to R²⁴ each independently is a substituted or unsubstituted aryl group having 6 to 30 ring carbon atoms, and the arbitrary substituent to be meant by the wording "substituted or unsubstituted" by any of R¹ to R²⁴, A¹ and A² each is independently an unsubstituted aryl group having 6 to 30 ring carbon atoms.

22. The compound according to claim 16, wherein:

R¹ to R²⁴ are hydrogen atoms,

A¹ is an unsubstituted (n+1)-valent residue of an aromatic hydrocarbon having 6 to 30 ring carbon atoms, or an unsubstituted (n+1)-valent residue of an aromatic heterocyclic compound having 5 to 30 ring atoms, and A² is an unsubstituted aryl group having 6 to 30 ring carbon atoms, or an unsubstituted heteroaryl group having 5 to 30 ring atoms.

23. A compound of formula (2):

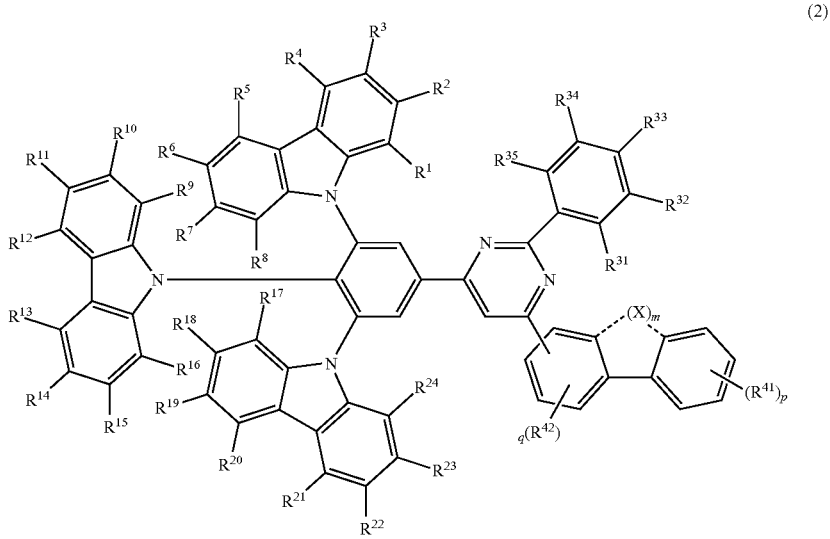

(2)

wherein:
$R^1$ to $R^{24}$ each independently represent a hydrogen atom, or a substituent, and the substituent is a substituted or unsubstituted aryl group having 6 to 30 ring carbon atoms, or a substituted or unsubstituted heteroaryl group having 5 to 30 ring atoms,
R31 to R35 each independently represent a hydrogen atom,
$R^{41}$ to $R^{42}$ each are independently same as $R^1$,
m represents 0 or 1,
when m is 0, X is absent, and the two benzene rings are not crosslinked,
when m is 1, X is O or S,
p represents an integer of 0 to 5,
q represents an integer of 0 to 4.

24. The compound according to claim 16, wherein the compound represented by the formula (1) is a compound of formula (3):

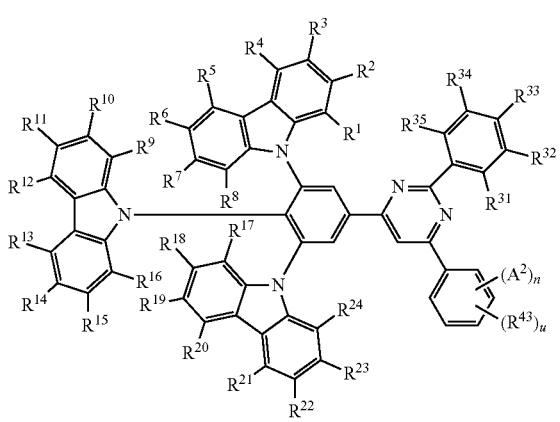

(3)

wherein:
$A^2$ is an unsubstituted aryl group having 6 to 30 ring carbon atoms, or an unsubstituted heteroaryl group having 5 to 30 ring atoms,
$R^{43}$ is the same as $R^1$, and
u represents an integer of 0 to (5-n).

25. The compound according to claim 16, wherein at least one hydrogen atom in the compound represented by the formula (1) is a deuterium atom.

26. The compound according to claim 16, wherein $R^1$ to $R^{24}$ are all deuterium atoms.

27. The compound according to claim 16, wherein:

n is 1, the group represented by $A^1$ is unsubstituted, the hydrogen atoms that the group represented by $A^1$ has are all deuterium atoms.

28. The compound according to claim 16, wherein:

n is 1, the group represented by $A^1$ is unsubstituted, the hydrogen atoms that the group represented by $A^1$ has are all deuterium atoms, the group represented by $A^2$ is unsubstituted, the hydrogen atoms that the group represented by $A^2$ has are all deuterium atoms.

29. A material for organic electroluminescent devices, comprising the compound of claim 16.

30. An organic electroluminescent device having a cathode, an anode, and organic layers disposed between the cathode and the anode, wherein the organic layers comprise a light-emitting layer, and wherein:

at least one layer of the organic layers comprises the compound of claim 16.

31. An electronic device comprising the organic electroluminescent device of claim 1.

32. A compound of formula ET-1, ET-3, ET-4, ET-5, ET-6, ET-7, or ET-8:
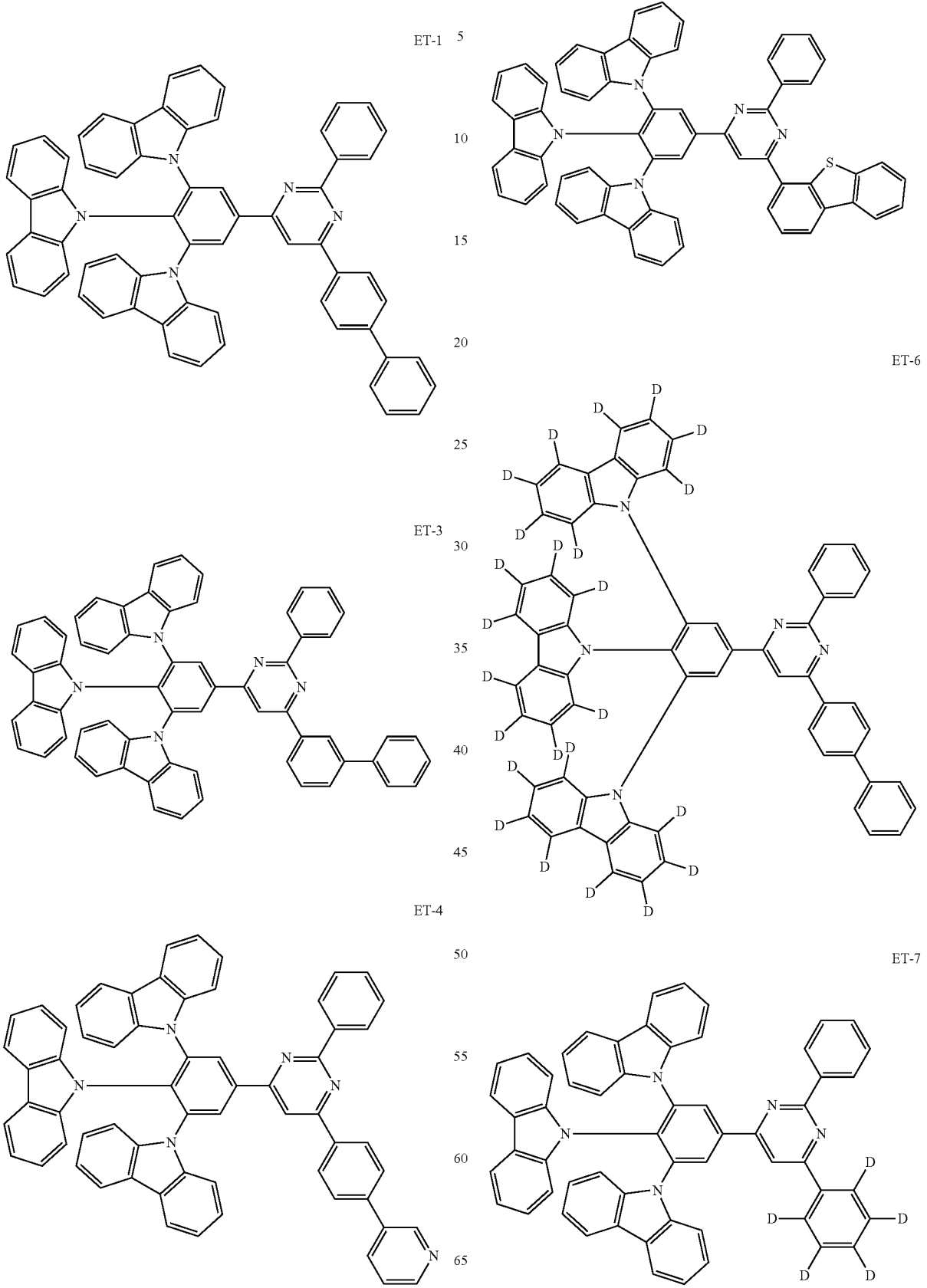

ET-8
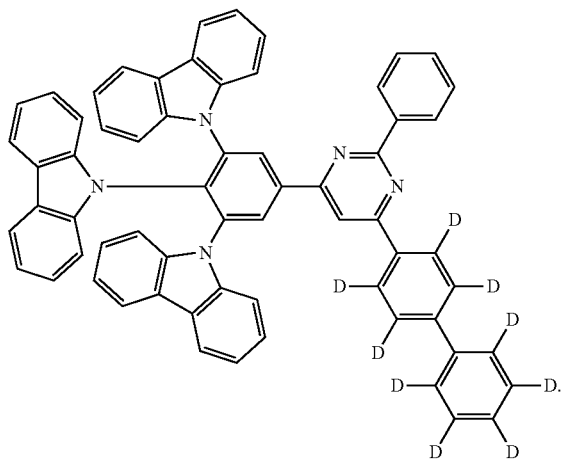
33. An organic electroluminescent device comprising:
a cathode, an anode, and organic layers disposed between the cathode and the anode, wherein:
the organic layers comprise a light-emitting layer, and a first layer disposed between the light-emitting layer and the cathode, and
the first layer comprises a compound of ET-1, ET-3, ET-4, ET-5, ET-6, ET-7, or ET-8:
ET-1
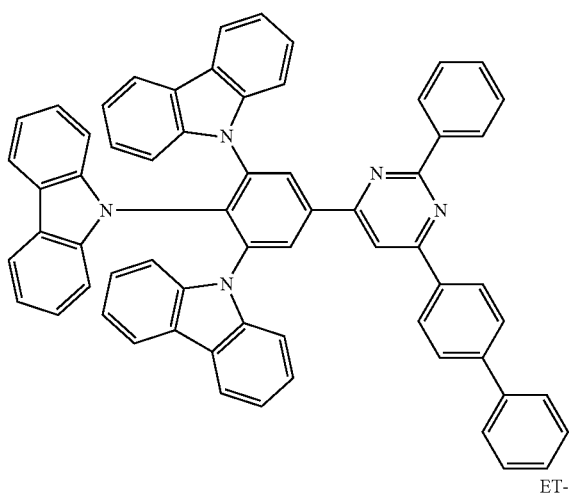
ET-3
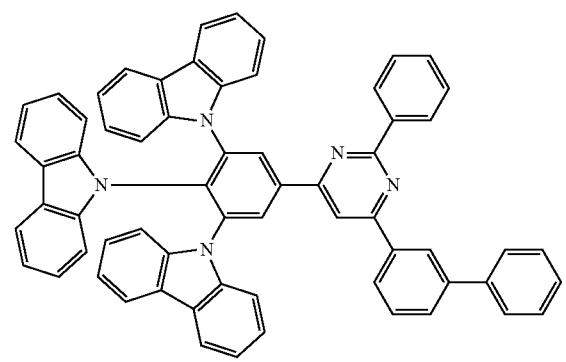
ET-4
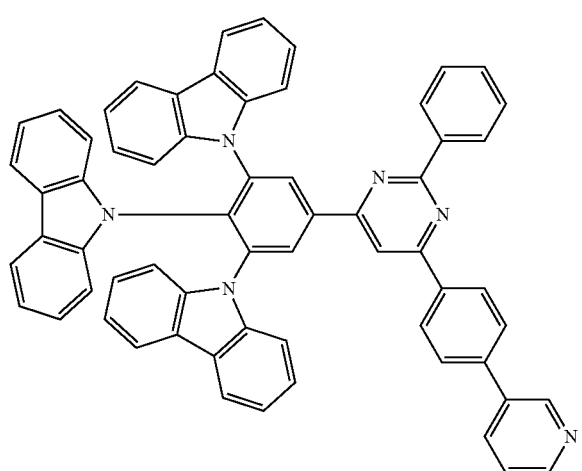
ET-5
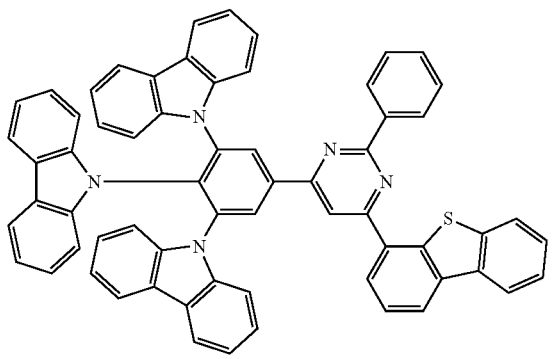
ET-6
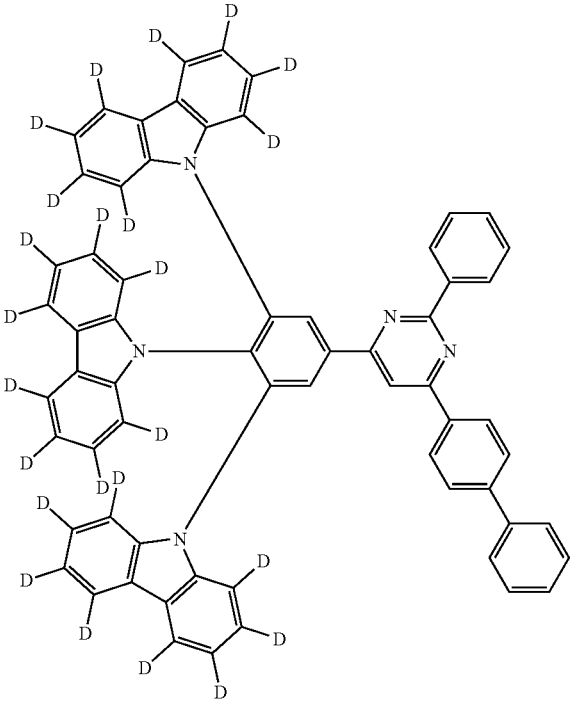

ET-7
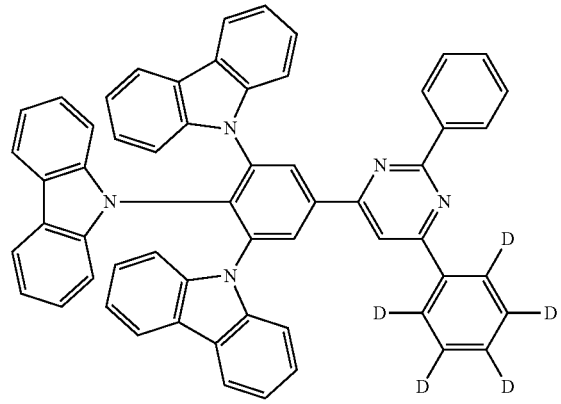
ET-8
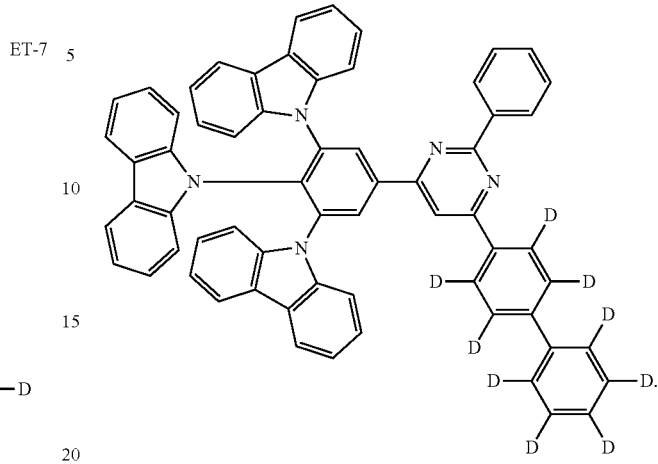
\* \* \* \* \*

UNITED STATES PATENT AND TRADEMARK OFFICE
CERTIFICATE OF CORRECTION

PATENT NO. : 11,903,308 B2  
APPLICATION NO. : 17/273563  
DATED : February 13, 2024  
INVENTOR(S) : Kei Yoshida et al.

It is certified that error appears in the above-identified patent and that said Letters Patent is hereby corrected as shown below:

In the Claims

Claim 1, Column 117, Line 5, "heteroaryl group having 5 to 30 ring atoms $R^{31}$ to $R^{35}$" should read -- heteroaryl group having 5 to 30 ring atoms, $R^{31}$ to $R^{35}$ --.

Claim 2, Column 117, Line 20, "wherein when $A^1$ is an (n+1)-valent residue of benzene" should read -- wherein $A^1$ is an (n+1)-valent residue of benzene --.

Claim 9, Column 119, Line 31, "R31 to R35 each independently represent a hydrogen atom," should read -- $R^{31}$ to $R^{35}$ each independently represent a hydrogen atom, --.

Claim 21, Column 122, Lines 47 and 48, "$R^1$ to $R^{24}$ each independently is" should read -- $R^1$ to $R^{24}$ is each independently --.

Claim 23, Column 123, Line 31, "R31 to R35 each independently represent a hydrogen atom," should read -- $R^{31}$ to $R^{35}$ each independently represent a hydrogen atom, --.

Signed and Sealed this  
Twenty-third Day of April, 2024

Katherine Kelly Vidal  
*Director of the United States Patent and Trademark Office*